US012404339B2

(12) United States Patent
Ober et al.

(10) Patent No.: US 12,404,339 B2
(45) **Date of Patent: *Sep. 2, 2025**

(54) METHOD OF DEPLETING TARGET ANTIGEN-SPECIFIC ANTIBODY FROM A PATIENT BY ADMINISTERING A FUSION PROTEIN (Seldeg) FOR SELECTIVELY DEPLETING ANTIGEN-SPECIFIC ANTIBODIES

(71) Applicant: THE TEXAS A&M UNIVERSITY SYSTEM, College Station, TX (US)

(72) Inventors: Elizabeth Sally Ward Ober, Southampton (GB); Venkata Siva Charan Devanaboyina, College Station, TX (US); Raimund Johannes Ober, Southampton (GB)

(73) Assignee: The Texas A&M University System, College Station, TX (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/930,545

(22) Filed: Sep. 8, 2022

(65) Prior Publication Data

US 2023/0087965 A1 Mar. 23, 2023

Related U.S. Application Data

(63) Continuation of application No. 16/465,975, filed as application No. PCT/US2017/064186 on Dec. 1, 2017, now Pat. No. 11,459,396.

(60) Provisional application No. 62/429,367, filed on Dec. 2, 2016.

(51) Int. Cl.

| | |
|---|---|
| *C07K 16/28* | (2006.01) |
| *A61K 38/00* | (2006.01) |
| *A61K 39/00* | (2006.01) |
| *C07K 14/71* | (2006.01) |
| *A61K 51/10* | (2006.01) |

(52) U.S. Cl.
CPC .......... *C07K 16/2881* (2013.01); *A61K 39/00* (2013.01); *A61K 39/0011* (2013.01); *C07K 14/71* (2013.01); *A61K 38/00* (2013.01); *A61K 51/1027* (2013.01); *C07K 2317/52* (2013.01); *C07K 2317/569* (2013.01); *C07K 2317/71* (2013.01); *C07K 2317/72* (2013.01); *C07K 2317/76* (2013.01); *C07K 2317/77* (2013.01); *C07K 2317/92* (2013.01); *C07K 2319/30* (2013.01)

(58) Field of Classification Search
CPC ............ C07K 16/2881; C07K 2317/52; C07K 2317/569; C07K 2317/71; C07K 2317/72; C07K 2317/76; C07K 2317/77; C07K 2317/92; C07K 2319/30; A61K 38/00

See application file for complete search history.

(56) References Cited

U.S. PATENT DOCUMENTS

| | | | |
|---|---|---|---|
| 2005/0249723 | A1 | 11/2005 | Lazar |
| 2006/0235208 | A1 | 10/2006 | Lazar et al. |
| 2016/0060358 | A1 | 3/2016 | Hay |
| 2017/0334962 | A1 | 11/2017 | Ober et al. |

FOREIGN PATENT DOCUMENTS

| | | | |
|---|---|---|---|
| WO | 0216414 | | 2/2002 |
| WO | 2002044329 | A2 | 6/2002 |
| WO | 2006130834 | A2 | 12/2006 |
| WO | 2012142515 | | 10/2012 |
| WO | 20120150319 | A1 | 11/2012 |
| WO | 20150100299 | A1 | 7/2015 |

OTHER PUBLICATIONS

Devanaboyina et al., Nature Communications, May 31, 2017, 6 pages plus 8 supplemental pages; DOI: 10.1038/ncomms15314).
Sun et al., Molecular Therapy vol. 29(3), Mar. 1, 2021, 2 pages plus 6 supplemental pages; (https://doi.org/10.1016/j.ymthe.2020.11.017).
Khare et al., (2021) 13(1), 6 pages (https://doi.org/10.1080/19420862.2021.1976705).
International Search Report and Written Opinion, PCT/US2017/064186, Mar. 15, 2018.
Battaini, et al., "Antibody response after vaccination with antigen-pulsed dendritic cells", International Journal of VBiological Markers, vol. 19, No. 3, pp. 213-220, (Jul.-Sep. 2004).

Challa et al., "Antigen dynamics govern the induction ofCD4+ T cell tolerance during autoimmunity", Journal of Autoimunity, vol. 72, pp. 84-94, published online: May 25, 2016.

Ha et al., "Immunoglobulin Fe Heterodimer Platform Technology: From Design to Applications in Therapeutic Antibodies and Proteins", Frontiers in Immunology, vol. 7, Art 394, pp. 1-6, publishes; Oct. 6, 2016.

Mann et al., "Transferrin conjugation confers mucosal molecular targeting to a model HIV-1 trimeric gp140 vaccine antigen", (2012), Journal of Controlled Release, vol. 158, pp. 240-249.
Neves et al., "Imaging cell death", (2014) Journal of Nuclear Medicine, vol. 55, No. 1, pp. 1-4.

(Continued)

*Primary Examiner* — Robert S Landsman
(74) *Attorney, Agent, or Firm* — Edell, Shapiro & Finnan, LLC

(57) ABSTRACT

The present disclosure includes a fusion protein, called a "Seldeg", including a targeting component that specifically binds to a cell surface receptor or other cell surface molecule at near-neutral pH, and an antigen component fused directly or indirectly to the targeting component. The antigen component is configured to specifically bind a target antigen-specific antibody. The present disclosure also includes a method of depleting a target antigen-specific antibody from a patient by administering to the patient a Seldeg having an antigen component configured to specifically bind the target antigen-specific antibody.

18 Claims, 19 Drawing Sheets

Specification includes a Sequence Listing.

(56) References Cited

OTHER PUBLICATIONS

Saito et al., "Vector-mediated delivery of 125I-laveled b-amyloid peptide Abl-40 through the blood-brain Barrier and binding to Alzheimer disease amyloid of the Abl-40/vector complex", Proc. Natl. Acad. Sci. USA, vol. 92, pp. 10227-10231, (Oct. 1995).
Wang et al., (2016), "Nanobody-derived nano biotechnology tool kits for diverse biomedical and biotechnology applications" International Journal of Nanomedicine, vol. 11, pp. 3287-3303, published Jul. 21, 2016.
Ward et al., (2015), "Targetingb FcRn for the modulation of antibody dynamics", Molecular Immunology, vol. 67, pp. 131-141.
Challa et al., "Autoantibody depletion ameliorates disease in murine experimental autoimmune encephalomyelitis" mAbs, Sep./Oct. 2013, pp. 655-659, vol. 5, Issue 5.

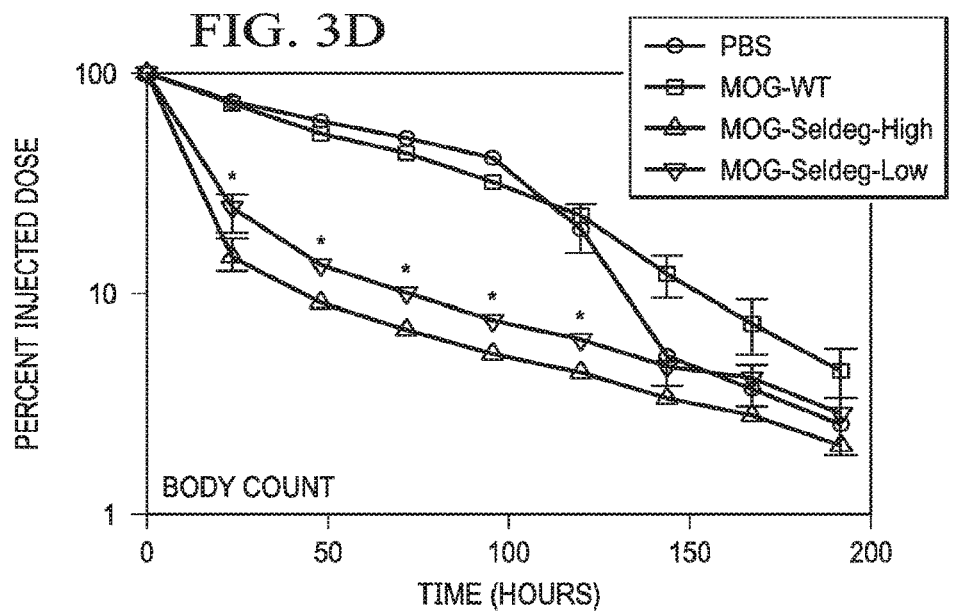
FIG. 3D
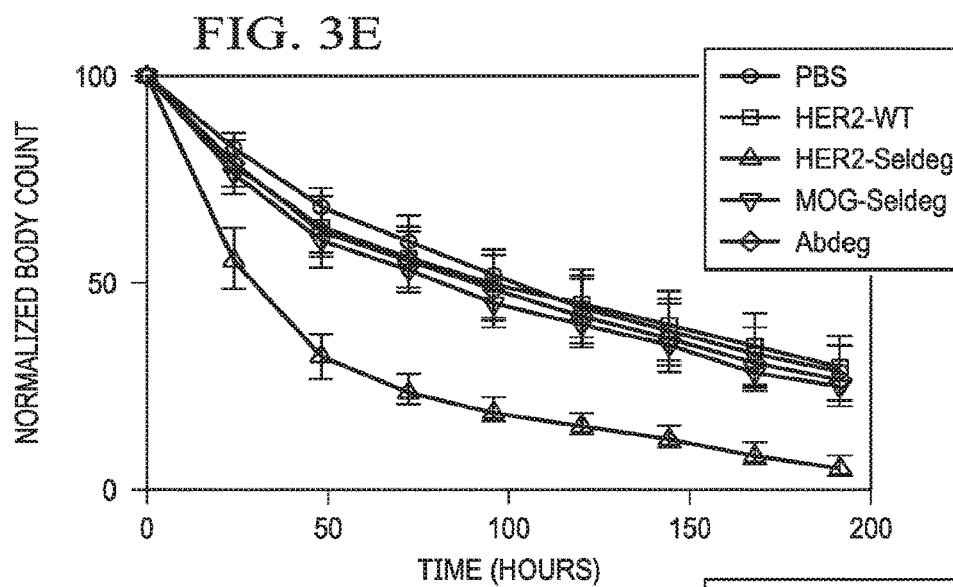
FIG. 3E
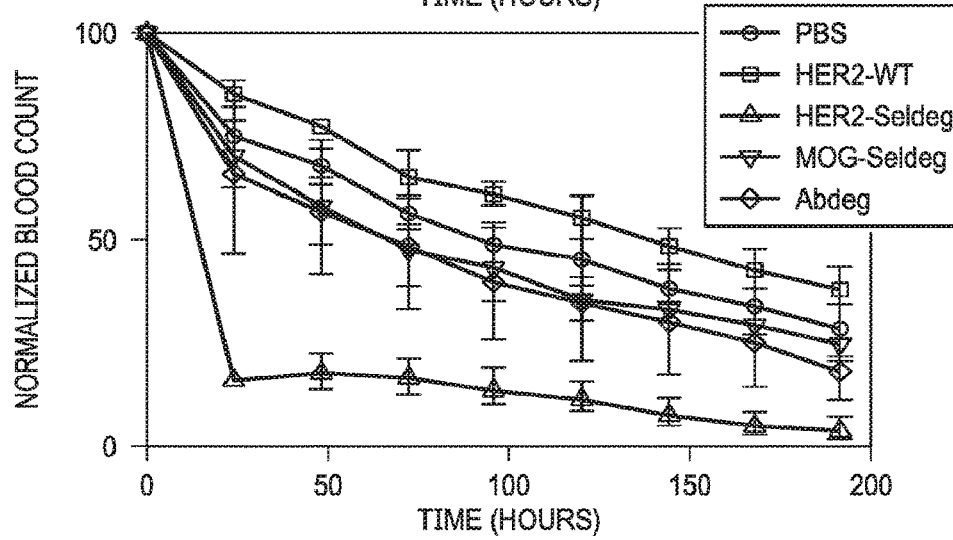

METHOD OF DEPLETING TARGET ANTIGEN-SPECIFIC ANTIBODY FROM A PATIENT BY ADMINISTERING A FUSION PROTEIN (Seldeg) FOR SELECTIVELY DEPLETING ANTIGEN-SPECIFIC ANTIBODIES

CROSS-REFERENCE TO RELATED APPLICATIONS

This application is a continuation of U.S. patent application Ser. No. 16/465,975, filed on May 31, 2019, now U.S. Pat. No. 11,459,396, issued on Oct. 4, 2022, which in turn is a National Stage Entry of International Application PCT/US2017/064186, with an international filing date of Dec. 1, 2017, which claims benefit to U.S. Provisional Patent Application No. 62/429,367, filed on Dec. 2, 2016, the contents of each of which are incorporated by reference herein in their entirety.

SEQUENCE LISTING

The instant application contains a Sequence Listing, which has been submitted electronically in ST.26 (XML) format and is hereby incorporated by reference in its entirety. Said Sequence List, created on Nov. 1, 2022, is named 16810002CON_SEQ_LIST_XML.1 and is 69 kilobytes in size.

TECHNICAL FIELD

This disclosure relates to engineered proteins, and more specifically, to fusion proteins that selectively deplete target antigen-specific antibodies from the body ("Seldegs").

BACKGROUND

Antibodies are Y-shaped proteins present in blood and other body fluids of the human body and the bodies of mammals. Antibodies are a critical component of the body's immune system. They function by recognizing a unique part of a foreign target, called the antigen. An antibody is able to selectively recognize and trigger an immune response to an antigen through its two antigen-binding sites. Each antigen-binding site is at the end of each upper tip of the antibody's Y-shape. The target antigen may bind one or both antigen-binding sites. The base of an antibody's Y-shape is called an Fc fragment. When an antibody binds to its target, the Fc region can bring about target clearance through antibody effector functions. Such responses can include cellular processes to destroy the antigen. In certain autoimmune diseases and other illnesses, pathogenic antibodies may be created that target self-antigens in the body, contributing to pathogenesis. An antibody may be in either of two physical forms, a soluble form that is secreted from the cell and is free in the blood plasma, or a membrane-bound form that is attached to the outer-membrane of a B cell. The secreted antibodies cause pathology in diseases involving autoreactive antibodies. They can also contribute to transplant rejection or the elimination of protein-based therapeutics.

Due to their ability to bind specifically to target molecules, antibodies can be used to treat diseases such as cancer and autoimmunity. They also have applications in the detection of tumors during whole body imaging using, for example, radiolabeled antibodies in positron emission tomography (PET). However, their relatively long in vivo persistence can lead to high background in non-tumor tissue, resulting in poor contrast for tumor imaging and undesirable off-target effects.

SUMMARY

The present disclosure includes fusion proteins, herein referred to as "Seldegs", that are configured to allow selective clearance of antigen-specific antibodies. A Seldeg includes a targeting component that is configured to specifically bind to a cell surface receptor or other cell surface molecule, and an antigen component that is configured to specifically bind to an antigen-specific antibody or a variant thereof.

The targeting component of the Seldeg includes a protein or a protein fragment that is configured to specifically bind to a cell surface receptor or other cell surface molecule. The antigen component of the Seldeg includes one molecule of an antigen or antigen fragment or antigen mimetic configured to specifically bind a target antigen-specific antibody. The antigen component is fused directly or indirectly to the targeting component.

The present disclosure also includes a method of depleting a target antigen-specific antibody from a patient by administering to the patient a Seldeg in an amount sufficient to remove at least 50% of the target antigen-specific antibody from the circulation or a target tissue in the patient.

The above Seldegs and methods may further include the following details, which may be combined with one another unless clearly mutually exclusive: i) the targeting component can bind to the cell surface receptor or cell surface molecule with a dissociation constant of less than 10 µM at near-neutral pH; ii) near-neutral pH may be greater than 6.8 and less than 7.5; iii) the Seldeg can comprise at least a first targeting component and a second targeting component, wherein the protein or protein fragment of the first targeting component is configured to bind to a different cell surface receptor or a different cell surface molecule than the protein or protein fragment of the second targeting component iv) the targeting component may include a heterodimer of two immunoglobulin Fc fragments in which one immunoglobulin Fc fragment of the heterodimer is fused to the antigen component and the other immunoglobulin Fc fragment may not be; v) the immunoglobulin Fc fragment may have substantially reduced binding or no detectable binding to Fc gamma receptors; vi) the immunoglobulin Fc fragments can be derived from an immunoglobulin class or isotype that does not bind to Fc gamma receptors or complement; vii) the immunoglobulin Fc fragments can be configured to bind to Fc gamma receptors and complement; viii) at least one of the immunoglobulin Fc fragments can be modified to have a higher binding affinity for FcRn at near-neutral pH than an unmodified immunoglobulin Fc fragment; ix) the antigen component may be fused to one immunoglobulin Fc fragment at an N-terminus or a C-terminus of a hinge-$CH_2$—$CH_3$ domain of the immunoglobulin Fc fragment; x) the immunoglobulin Fc fragments may be modified to have no binding affinity for Fc gamma receptors and/or complement (C1q), or lower binding affinity for Fc gamma receptors and/or complement (C1q) than unmodified immunoglobulin Fc fragments; xi) the targeting component may include one or more antibody variable regions or fragments thereof that are configured to specifically bind to the cell surface receptor or the cell surface molecule; xii) the antibody variable region or fragment thereof may include at least one nanobody; xiii) the nanobody may be a nanobody multimer in which one nanobody is fused to the antigen component and all other nanobodies in the nanobody multimer may not be; xiv) the targeting component may be configured to dissociate from the cell surface receptor or cell surface molecule following entry into an endosome of a complex comprising the Seldeg and the cell surface receptor or cell surface molecule; xv) the antigen component may be fused to an N-terminal location or a C-terminal location on the targeting component; xvi) the antigen component may be fused to a non-terminal location on the targeting component; xvii) the antigen component may be fused to the targeting component via a chemical reaction, through a linker, or during formation of a single combined antigen component-targeting component fusion protein; xviii) the targeting component can be one or more albumin molecules, albumin fragments or mutated albumin variants that are configured to specifically bind to a FcRn; xix) the targeting component can include one or more antibody variable domains or nanobodies that are configured to bind to a transferrin receptor; xx) the targeting component can include one or more protein molecules or protein domains configured to bind to a transferrin receptor; xxi) the targeting component can include one or more protein molecules or protein domains configured to bind to a phosphatidylserine; xxii) the targeting protein component can include one or more antibody variable domains or nanobodies configured to bind to a phosphatidylserine; xxiii) the one or more protein molecules or protein domains can be configured to bind the phosphatidylserine via a calcium-dependent mechanism; xxiv) the targeting component can include a C2A domain of synaptotagmin 1; xxv) the Seldeg can include at least a first antigen component and a second antigen component, wherein the one molecule of the antigen, antigen fragment or antigen mimetic of the first antigen component is different to the one molecule of the antigen molecule, antigen fragment or antigen mimetic of the second antigen component; xxvi) the Seldeg can include at least a first antigen component and a second antigen component, wherein the one molecule of the antigen, antigen fragment or antigen mimetic of the first antigen component is the same as the one molecule of the antigen molecule, antigen fragment or antigen mimetic of the second antigen component; xxvii) the method may include administering an amount sufficient of Seldeg to remove at least 50% of the target antigen-specific antibody from the circulation or the target tissue in the patient within five hours of administration; xxviii) the method may include administering a Seldeg having a targeting component that includes a protein or protein fragment configured to bind to the cell surface receptor or other cell surface molecule with a dissociation constant of less than 10 μM at near neutral pH; xxix) the amount sufficient of Seldeg administered may be an amount at least equimolar to the amount of target antigen-specific antibody to be depleted; xxx) the method may include administering the Seldeg in an amount sufficient to remove at least 90% of the target antigen-specific antibody from the circulation or target tissue in the patient within two hours of administration; xxxi) the Seldeg may be administered in an amount sufficient to remove at least 50% of the target antigen-specific antibody from the circulation or target tissue in the patient within one hour of administration; xxxii) the Seldeg may be re-administered whenever 50% of patients are expected to have regenerated a threshold amount of target antigen-specific antibody in the circulation or target tissue; xxxiii) the Seldeg may remove less than 10% of non-target antibodies in the circulation or in a tissue targeted by the target antigen-specific antibody; xxxiv) the Seldeg may remove an amount of non-targeted antibodies in the circulation or in the target tissue of the patient that does not cause a clinically adverse effect in the patient; xxxv) the Seldeg may remove less than 1% of non-target antibodies in the circulation or in a tissue targeted by the target antigen-specific antibody; xxxvi) the Seldeg may cause degradation of the target antigen-specific antibody by a cell expressing the cell surface receptor or cell surface molecule; xxxvii) the Seldeg may be administered to a patient with an autoimmune disease and the target antigen-specific antibody may specifically bind to an autoantigen; xxxviii) the Seldeg may be administered to a patient receiving a transplanted organ and the target antigen-specific antibody may specifically bind to an antigen on the transplanted organ; xxxvix) the Seldeg may be administered to increase contrast during tumor imaging and the target antigen-specific antibody may specifically bind to a tumor antigen; xl) the Seldeg may be administered to a patient who has received a biologic and the target antigen-specific antibody may be the biologic; xli) the Seldeg may be administered to a patient prior to the delivery of a therapeutic agent, if the patient has antibodies specific for the therapeutic agent, if the patient has antibodies specific for the therapeutic agent, and the Seldog is configured to target the antibodies specific for the therapeutic agent; xlii) the Seldeg may be administered to provide a PET image contrast agent; xliii) the target antigen-specific antibody may be an anti-MOG antibody; xliv) the target antigen-specific antibody may be an anti-HER2 antibody; xlv) the Seldeg may include proteins having amino acid sequences of at least one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, or SEQ ID NO:34, or a homolog thereof, xlvi) the Seldeg may include a heterodimer of proteins having amino acid sequences of i) SEQ ID NO: 2 plus SEQ ID NO: 6, ii) SEQ ID NO: 4 plus SEQ ID NO:6, iii) SEQ ID NO:8 plus SEQ ID NO:10, iv) SEQ ID NO:12 plus SEQ ID NO:14, v) SEQ ID NO:14 plus SEQ ID NO:16 plus SEQ ID NO:20, vi) SEQ ID NO: 22 plus SEQ ID NO: 24, vii) SEQ ID NO: 26 plus SEQ ID NO: 28, viii) SEQ ID NO: 30 plus SEQ ID NO: 6, ix) SEQ ID NO: 32 plus SEQ ID NO: 6, or x) SEQ ID NO: 34 plus SEQ ID NO: 6, or homologs thereof.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which:

FIG. 1 is a schematic diagram of selected cellular events that lead to the degradation of antigen-specific antibodies in the presence of Seldegs;

FIG. 2A is a schematic diagram of a Seldeg including an antigen fused to a N-terminal location of an Fc fragment;

FIG. 2B is a schematic diagram of a Seldeg including an antigen fused to a C-terminal location of an Fc fragment;

FIG. 2C is a schematic diagram of a Seldeg including an antigen fused to a non-terminal location of an Fc fragment;

FIG. 2D is a schematic diagram of a Seldeg including an antigen fused to a terminal location of a protein or protein fragment that binds to a cell surface receptor or cell surface molecule;

FIG. 2E is a schematic diagram of a Seldeg including an antigen fused to a non-terminal location of a protein or protein fragment that binds to a cell surface receptor or cell surface molecule;

FIG. 3D shows a graph reporting exemplary normalized body counts versus time, showing clearance of an antigen-specific antibody by an exemplary FcRn-targeting Seldeg;

FIG. 3E shows additional graphs reporting exemplary normalized blood and body count versus time, showing clearance of an antigen-specific antibody by an exemplary FcRn-targeting Seldeg;

Figure 4A:
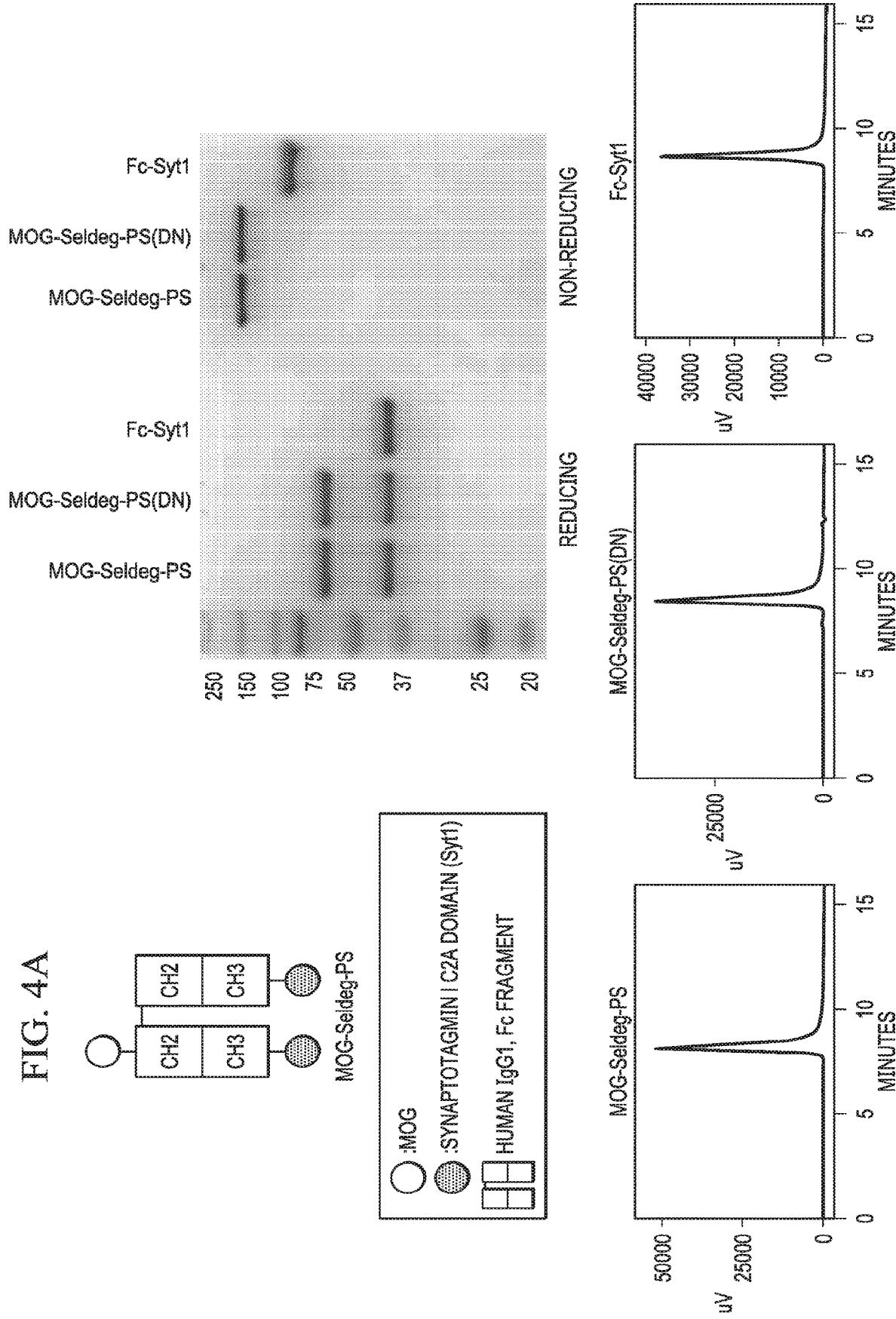
Figure 4B:
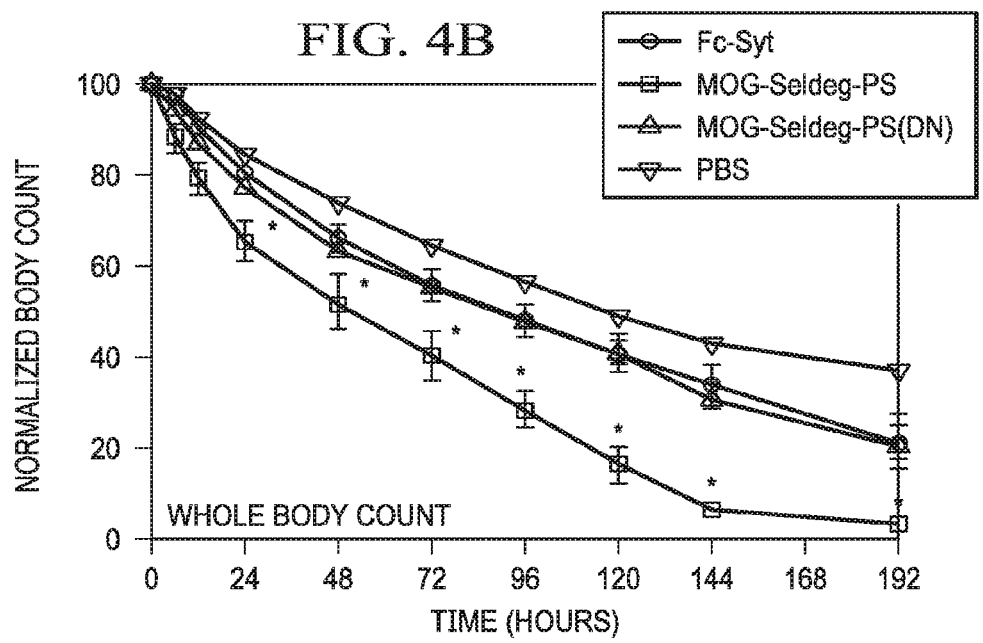
Figure 4B:
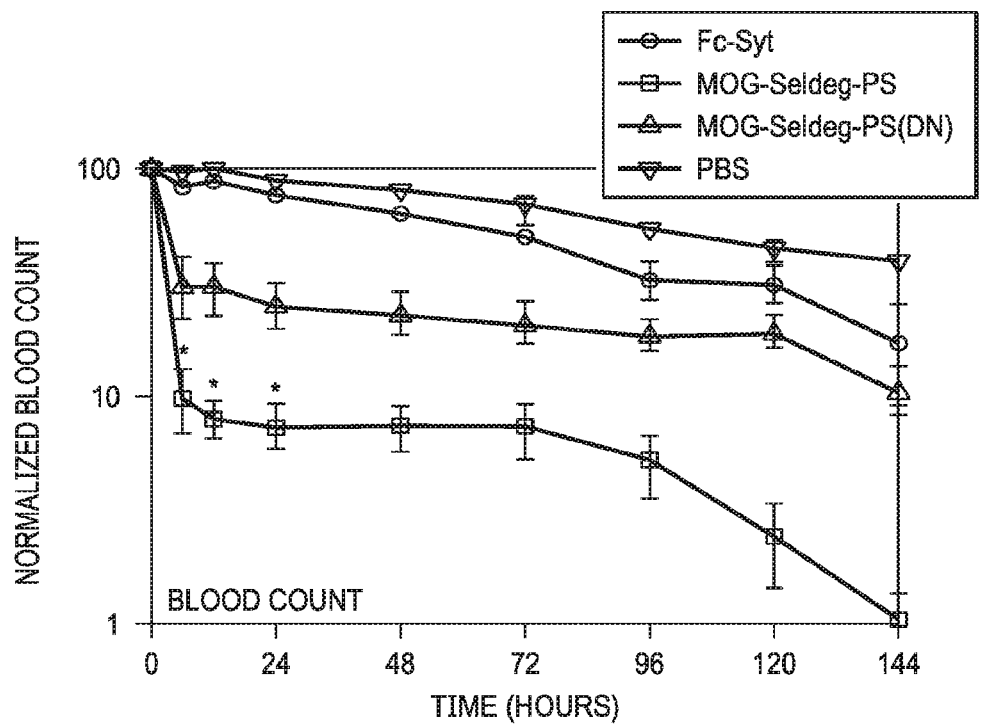
Figure 5A:
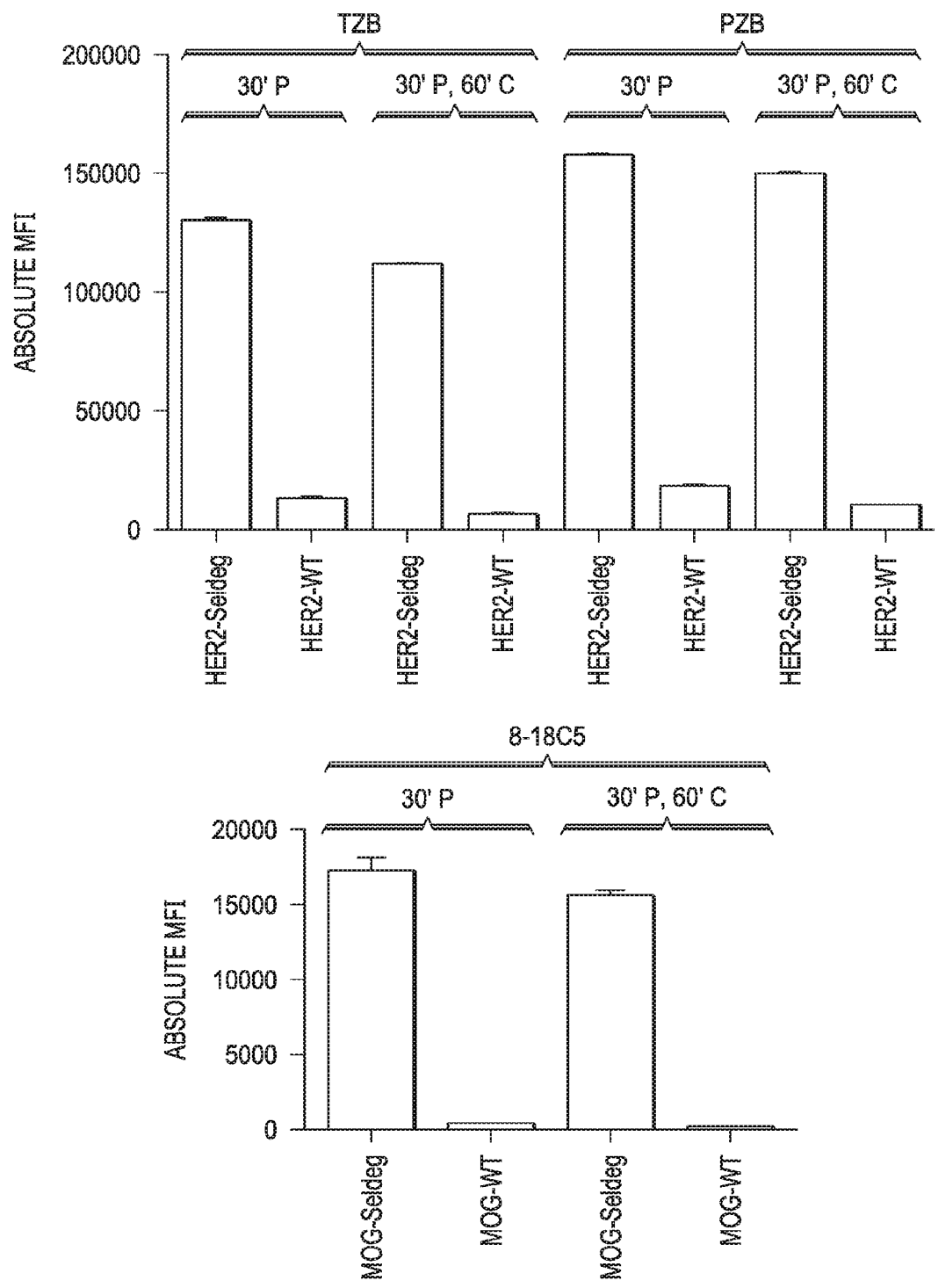
Figure 5B:
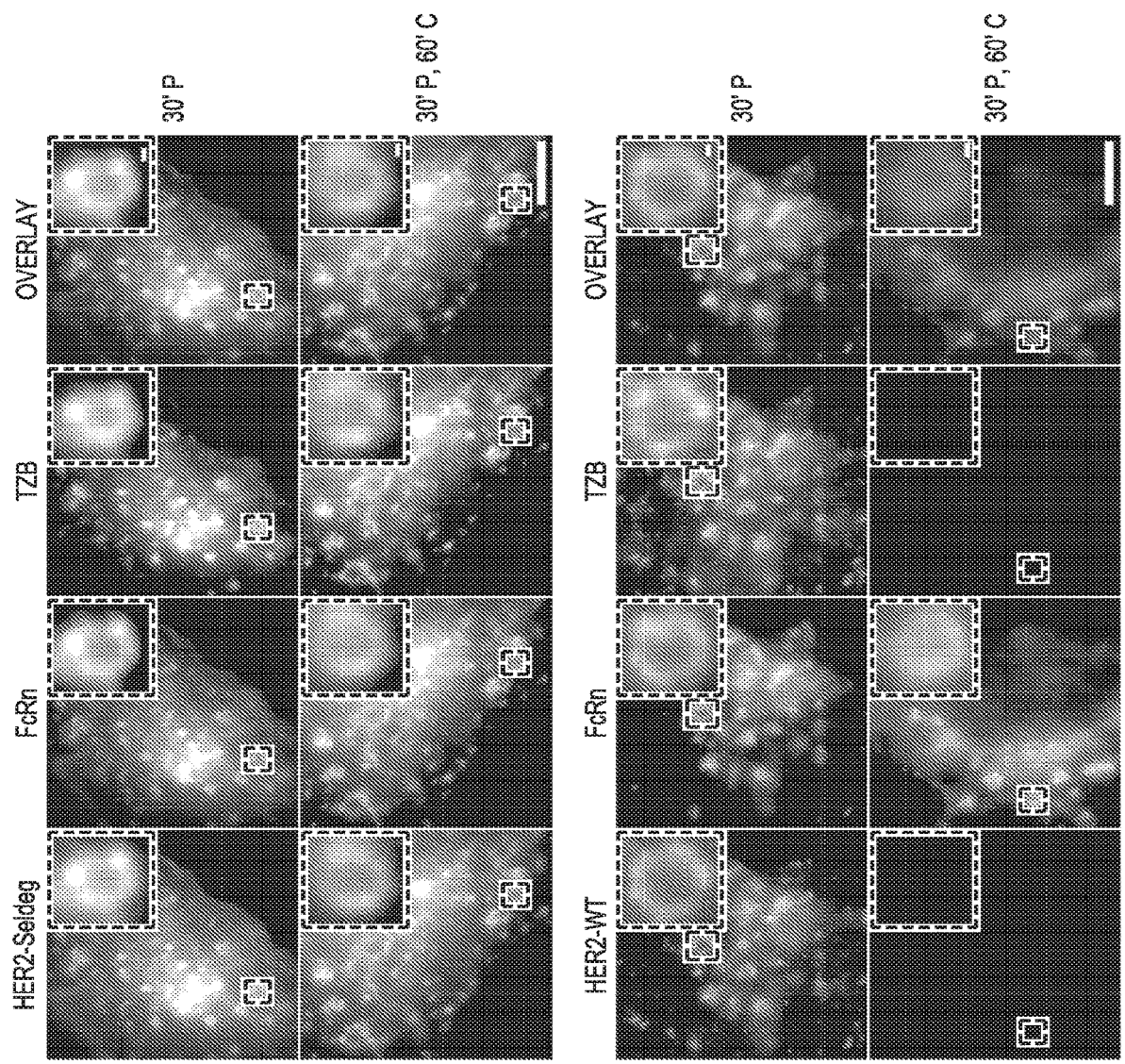
Figure 5C:
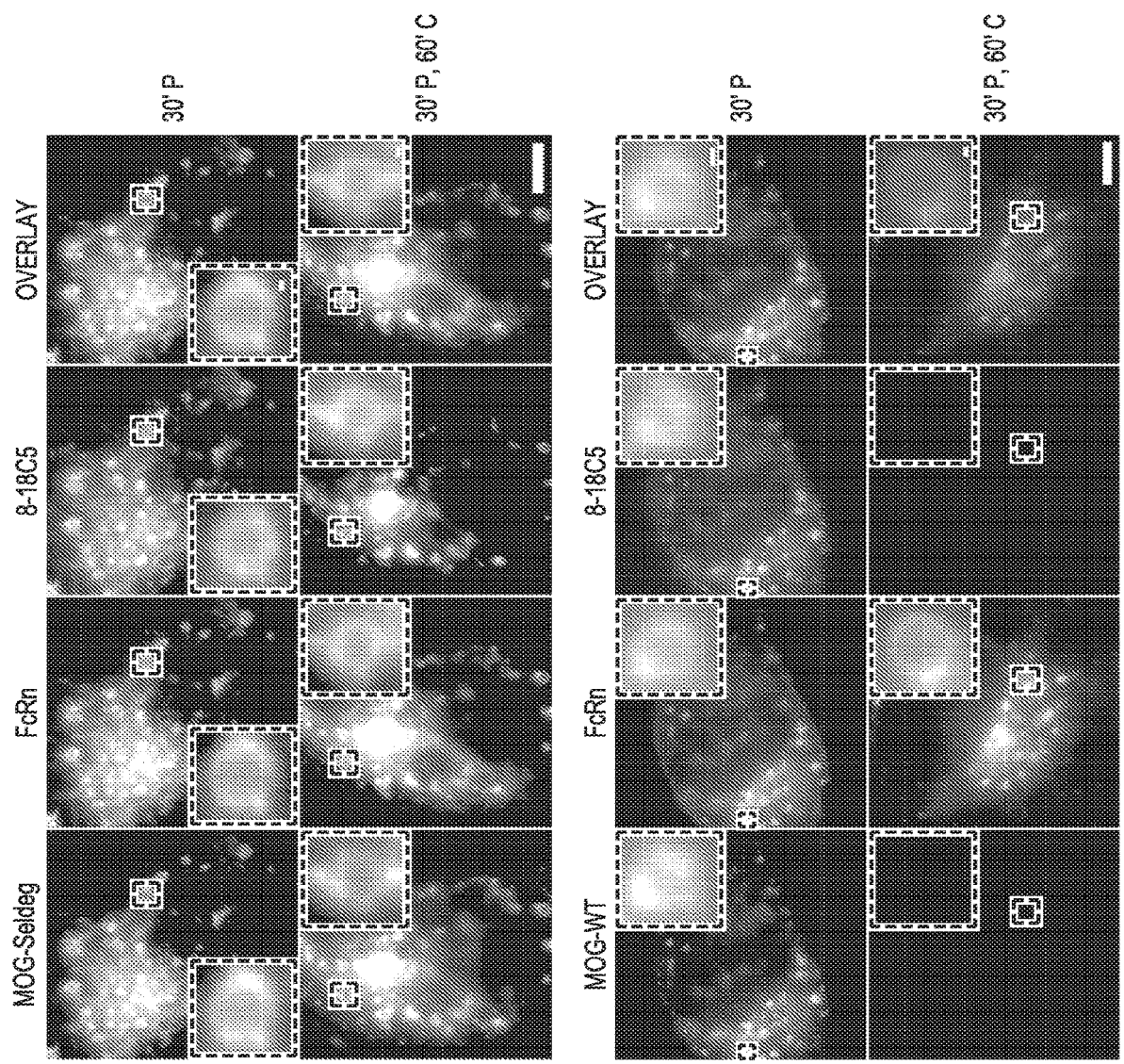
Figure 6A:
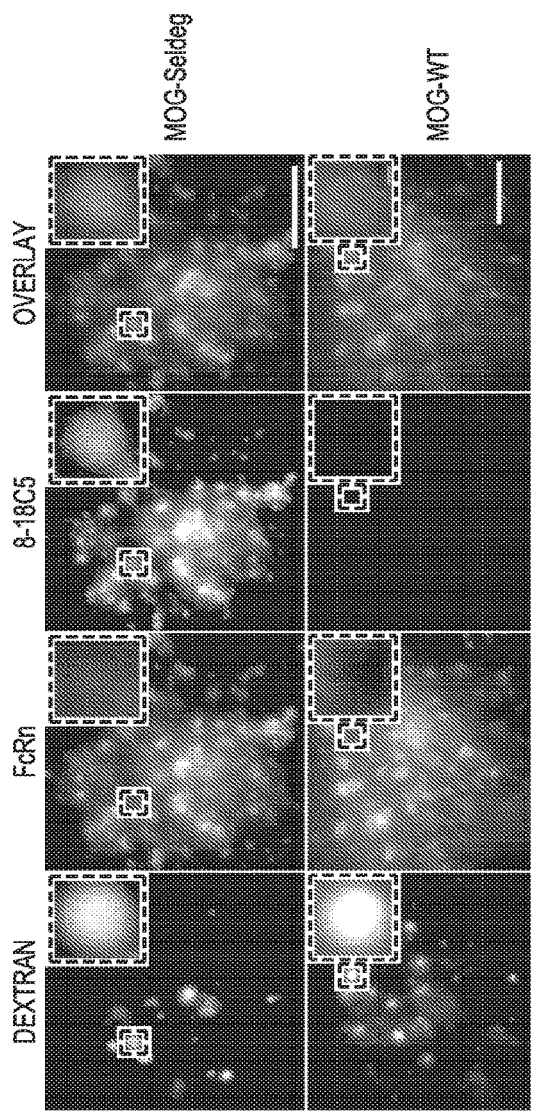
Figure 6B:
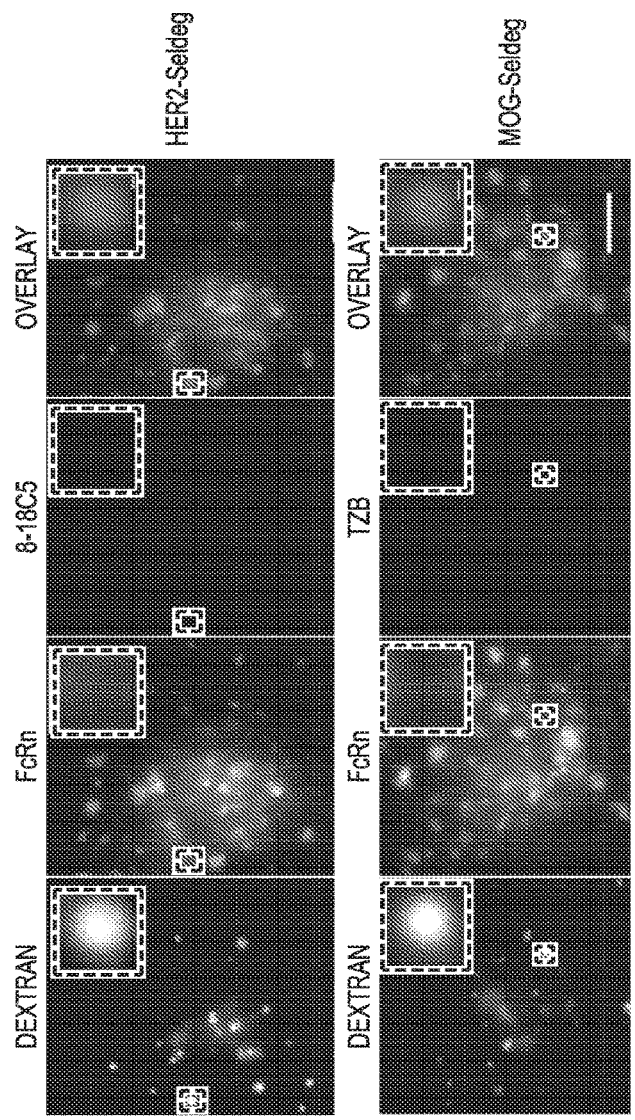
Figure 7:
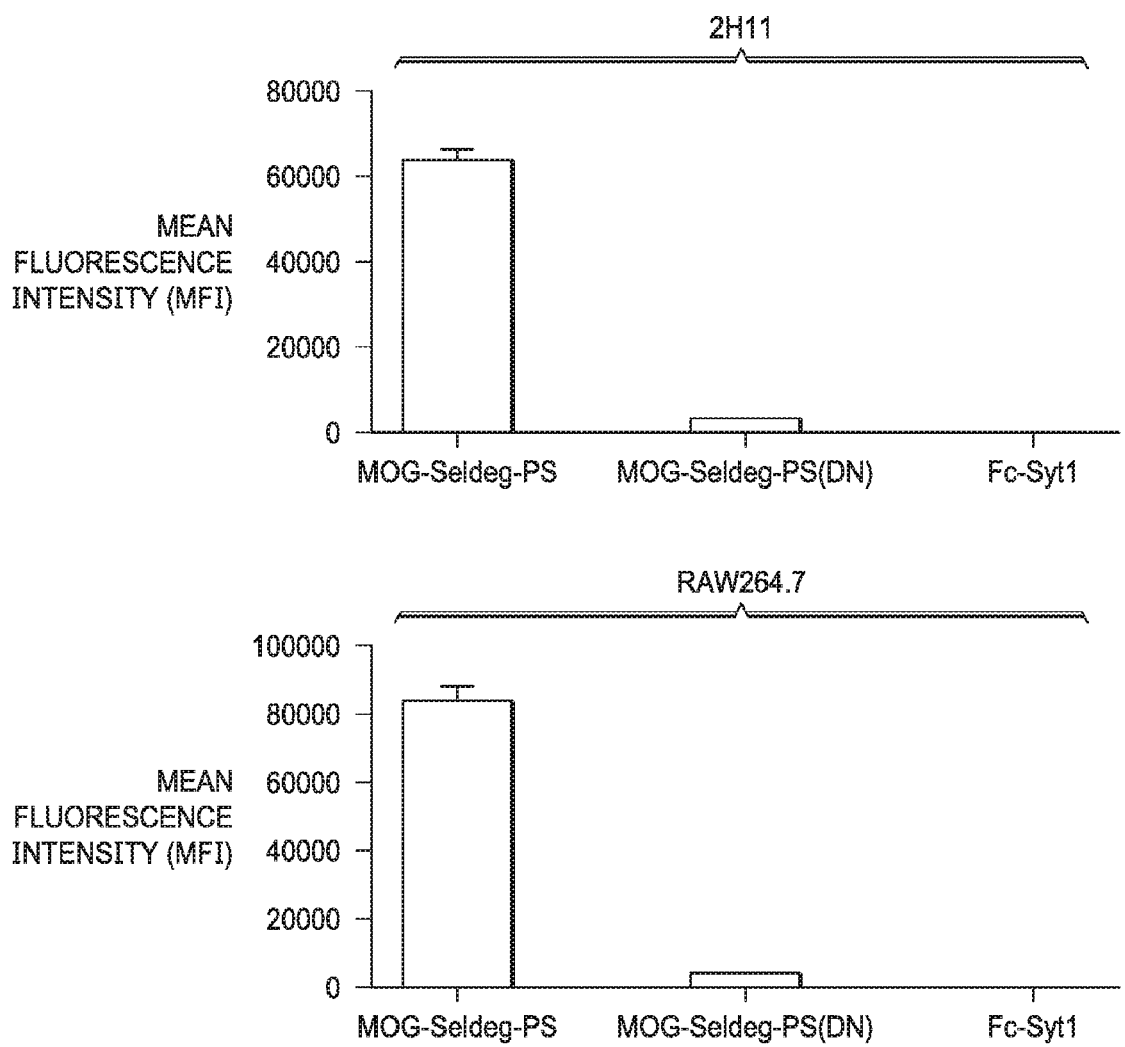
Figure 8:
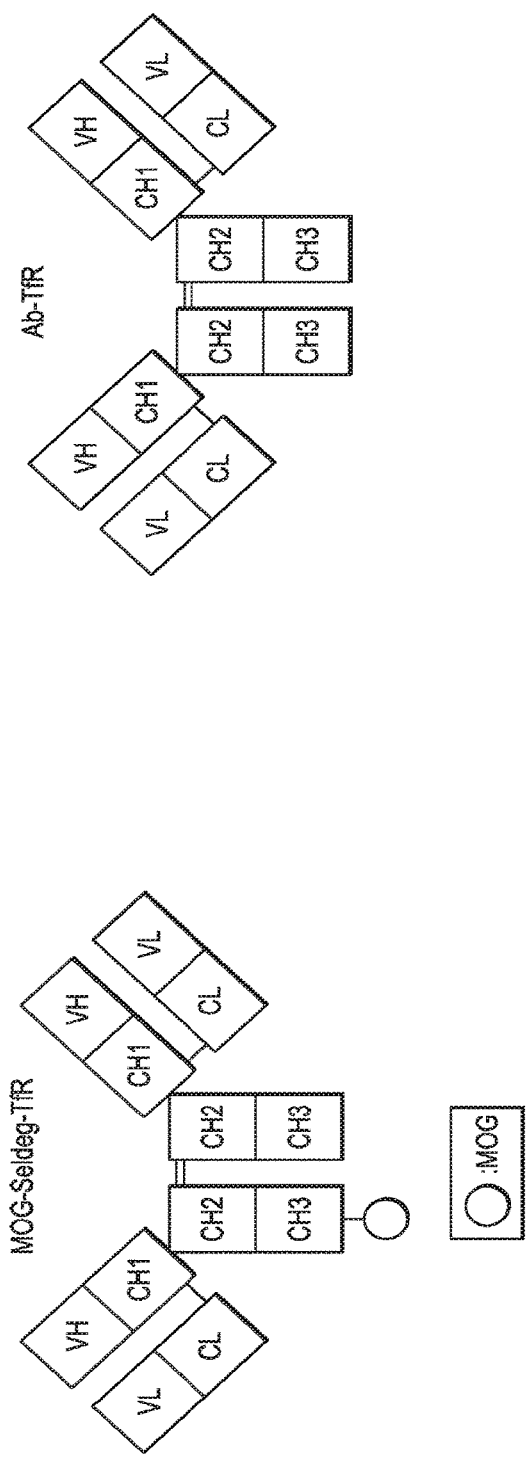
Figure 8:
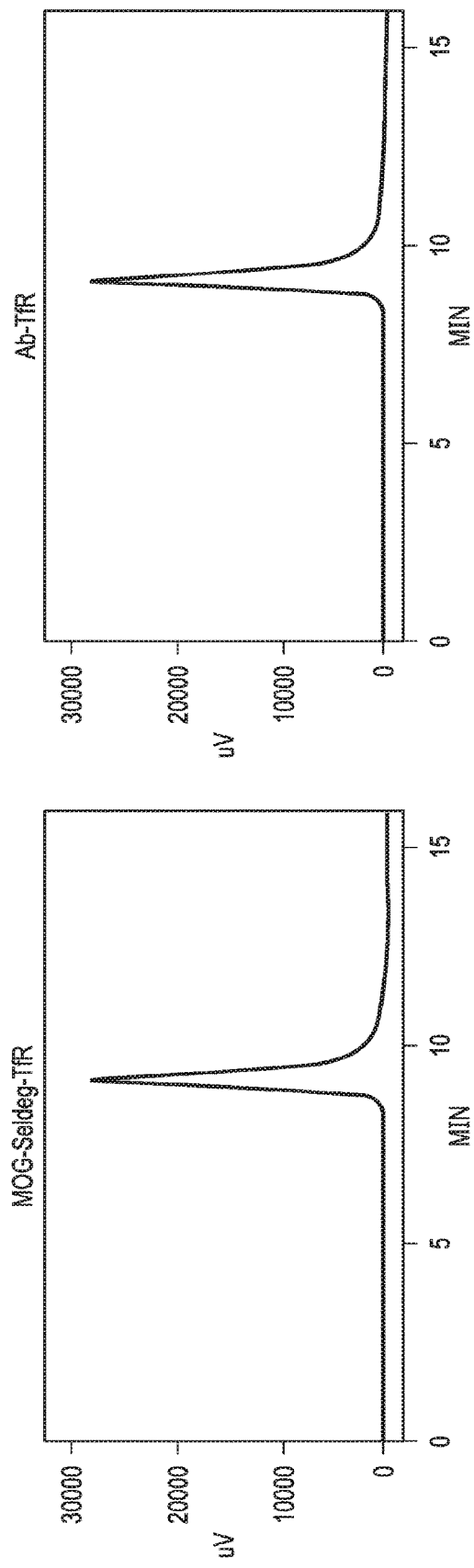
Figure 9:
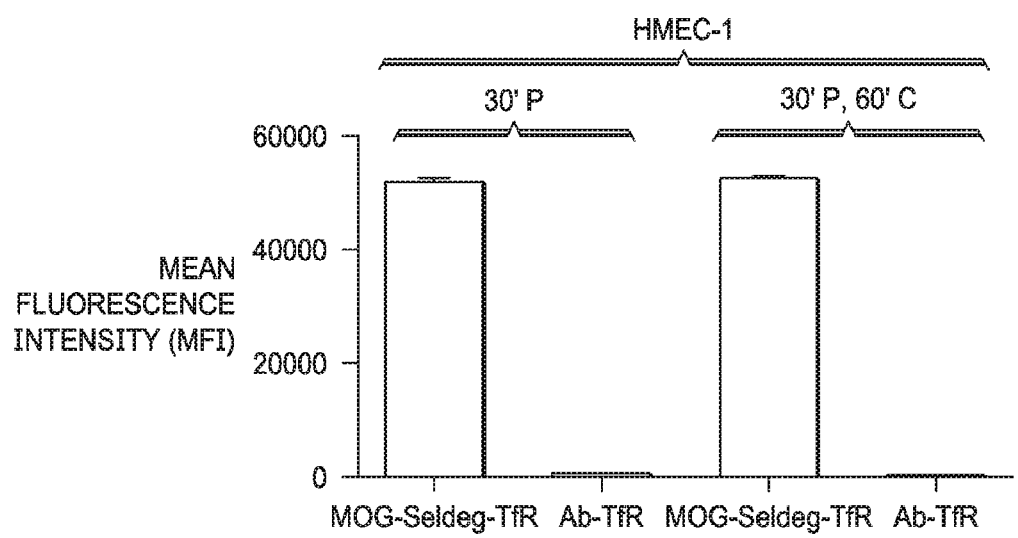
Figure 10A:
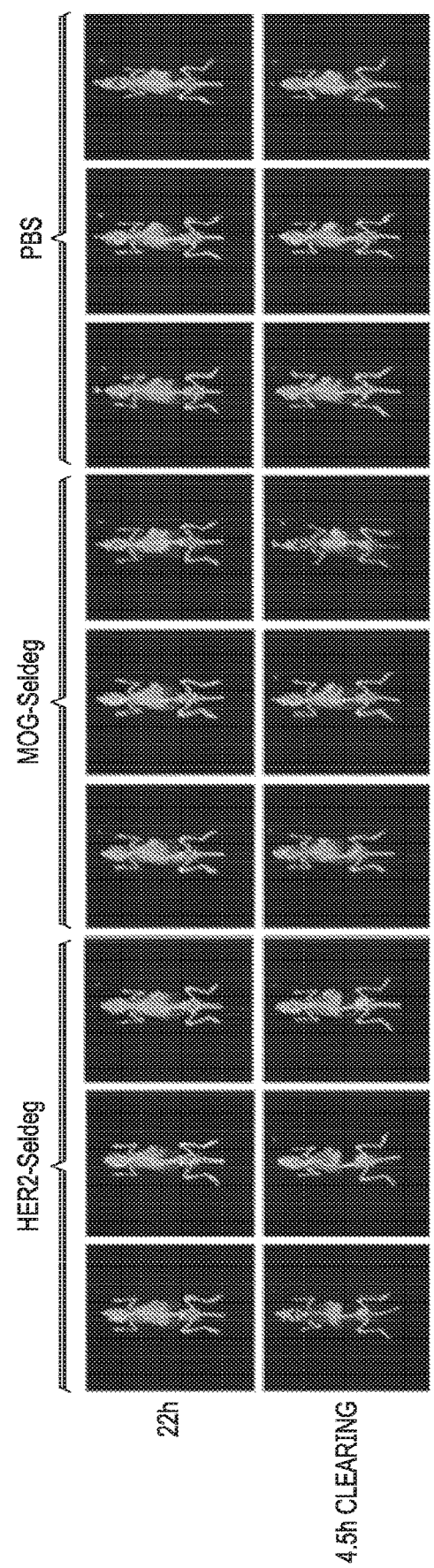

FIG. 4A shows in the upper left panel a schematic diagram of an exemplary Seldeg referred to as MOG-Seldeg-PS comprising an antigen fused to targeting protein (C2A domain of synaptotagmin 1, Syt1) that binds to phosphatidylserine (PS); in the upper right panel FIG. 4A shows exemplary SDS-PAGE gels (reducing and non-reducing conditions) of recombinant proteins of MOG-Seldeg-PS, MOG-Seldeg-PS(DN) with mutations that substantially reduce binding to PS, and Fc-Syt1 that has no antigen (MOG) attached; in the lower panel, FIG. 4A shows exemplary HPLC profiles of the recombinant proteins that are shown in the upper right FIG. 4A, MOG-Seldeg-PS, MOG-Seldeg-PS(DN) and Fc-Syt1;

FIG. 4B shows additional graphs reporting exemplary normalized blood and body count versus time, showing clearance of an antigen-specific antibody by an exemplary PS-targeting Seldeg;

FIG. 5A shows graphs reporting exemplary data showing the accumulation of antigen-specific antibodies in cells in the presence of exemplary FcRn-targeting Seldegs and control proteins;

FIG. 5B is an exemplary series of microscopic images of an exemplary FcRn-targeting Seldeg and control protein in the presence of target antigen-specific antibodies, with microscopic images of representative endosomes cropped, expanded, and presented in the top right-corner insets;

FIG. 5C is another series of exemplary microscopic images of an exemplary FcRn-targeting Seldeg and control protein in the presence of target antigen-specific antibodies, with microscopic images of representative endosomes cropped, expanded, and presented in the top right-corner insets;

FIG. 6A is another series of exemplary microscopic images of an exemplary FcRn-targeting Seldeg and control protein in the presence of target antigen-specific antibodies, with microscopic images of representative lysosomes cropped, expanded, and presented in the top right-corner insets;

FIG. 6B is another series of exemplary microscopic images of exemplary FcRn-targeting Seldegs in the presence of antigen-specific antibodies that do not recognize the antigen that is being targeted by the Seldeg, with microscopic images of representative lysosomes cropped, expanded, and presented in the top right-corner insets;

FIG. 7 shows graphs reporting exemplary data showing the accumulation of antigen-specific antibodies in cells in the presence of exemplary PS-targeting Seldegs and control proteins;

FIG. 8 is a schematic diagram of an exemplary Seldeg including an antigen fused to targeting protein (antibody) that binds to the transferrin receptor (TfR); HPLC profiles of the recombinant proteins are shown, including an analysis of the targeting protein (antibody) without antigen (MOG) attached;

FIG. 9 is a graph reporting exemplary data showing the accumulation of antigen-specific antibodies in cells in the presence of an exemplary TfR-targeting Seldeg and control protein;

FIG. 10A is an exemplary series of positron emission tomography (PET) analyses of tumors in mice following delivery of radiolabeled HER2-specific antibody and treatment with an exemplary FcRn-targeting Seldeg, control protein or vehicle control.

Figure 10B:
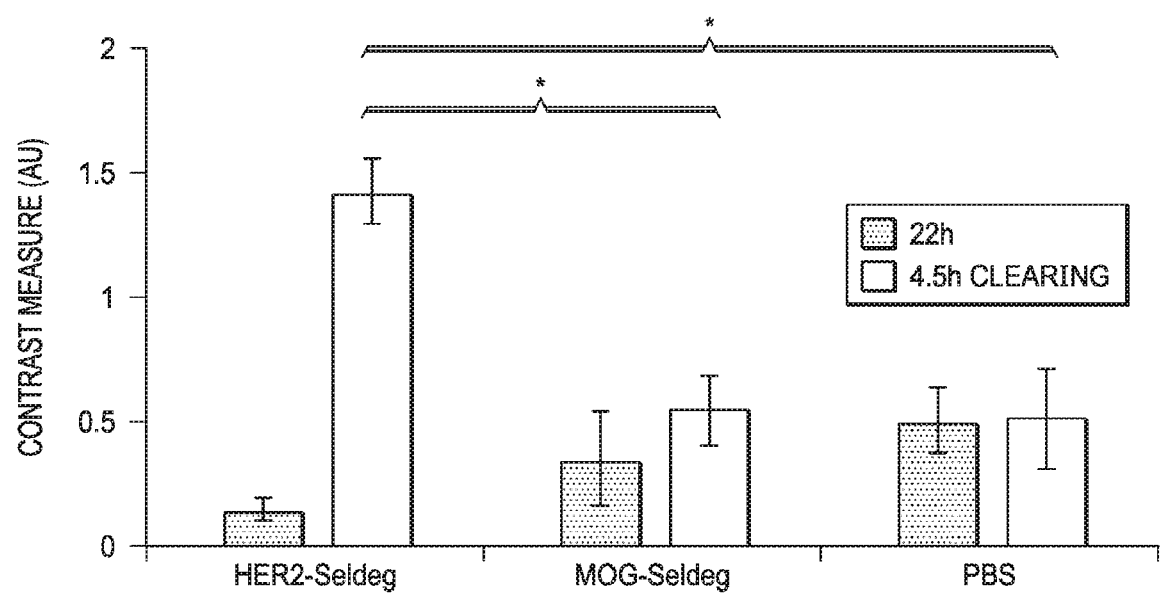

FIG. 10B shows a graph reporting contrast measures for tumor:thoracic regions of tumor-bearing mice following delivery of radiolabeled HER2-specific antibody and treatment with an exemplary FcRn-targeting Seldeg, control protein or vehicle control.

DETAILED DESCRIPTION

This disclosure relates to engineered proteins, and more specifically, to Seldegs, which are fusion proteins that are configured to selectively target antigen-specific antibodies for depletion from the body. Seldegs cause the selective degradation of the targeted antigen-specific antibodies by binding to the antigen-specific antibodies and directing them to late endosomes or lysosomes, which contain degradative enzymes. A Seldeg is a fusion protein or molecule that includes at least a targeting component and an antigen component. The targeting component includes a protein or protein fragment or other molecule that is configured to bind to a cell surface receptor or other cell surface molecule. The antigen component includes one molecule of an antigen, antigen fragment or antigen mimetic that is recognized by the targeted antigen-specific antibody.

Upon binding of the antigen-specific antibody to the antigen component, a complex is formed comprising the Seldeg and the antigen-specific antibody. The complex is also configured to bind to the cell surface receptor or other cell surface molecule, allowing cellular internalization of a complex that includes the Seldeg, the antigen-specific antibody, and the targeted cell surface receptor or other cell surface molecule (see FIG. 1). The targeted cell surface receptor or cell surface molecule may dissociate from the complex upon entry into the endosomes, due to acidic pH, low calcium concentrations and/or other conditions that distinguish the endosomal environment from the extracellular environment. Internalization into endosomes and lysosomal entry results in the selective degradation of the complex.

The term "antigen-specific antibody" as used herein refers to an antibody or antibody that binds to a particular antigen, antigen fragment or antigen mimetic.

The term "antigen fragment" as used herein refers to a part of the antigen that can be recognized by the antigen-specific antibody.

The term "antigen mimetic" as used herein refers to a protein, protein fragment, peptide or other molecule that has the same overall shape and properties as the part of the antigen that is recognized by an antigen-specific antibody.

The term "cell surface molecule" as used herein refers to a protein or other biological molecule (e.g. phospholipid, carbohydrate) that is exposed on the plasma membrane of a cell.

Seldegs may include an antigen fused to an Fc fragment of an IgG antibody (herein also referred to as "immunoglobulin Fc fragment"), an FcRn-specific nanobody-antigen fusion molecule, an FcRn-specific antibody that binds to FcRn through its variable region fused to an antigen, an albumin-antigen fusion protein, a PS-binding protein, a TfR-specific antibody or other protein, protein fragment or other molecule that is configured to bind to a cell surface receptor or other cell surface molecule identifiable by skilled persons upon reading of the present disclosure.

Examples of Seldegs described herein include targeting components that are configured to bind to cell surface molecules such as human FcRn, exposed phosphatidylserine (PS) or the transferrin receptor (TfR) with affinities (dissociation constants) of less than 10 μM at near neutral pH.

FcRn and TfR are proteins, and PS is a phospholipid, that may be found on the surface and within multiple different cell types within the body. This invention is not limited to targeting these receptors or cell surface molecules, and many other targets could be envisaged such as the low density lipoprotein receptor, high density lipoprotein receptor, asialoglycoprotein receptor, inhibitory Fc gamma receptors, T cell receptor, B cell receptor, G-protein coupled receptors, insulin receptor, glucagon receptors, galactose receptors, mannose receptors, VEGF receptors, mannose receptors among others identifiable by those skilled in the art. Other targets can be identified in, for example, the following publications or databases: Cell surface receptor protein atlas (Bausch-Fluck, D., Hofmann, A., Bock, T., Frei, A. P., Cerciello, F., Jacobs, A., Moest, H., Omasits, U., Gundry, R. L., Yoon, C., Schiess, R., Schmidt, A., Mirkowska, P., Härtlova, A., Van Eyk, J. E., Bourquin, J-P., Aebersold, R., Boheler, K. R., Zandstra, P., Wollscheid, B. (2015) A mass spectrometric-derived cell surface protein atlas. PLoS One 10: e0121314), and the Human protein atlas (https://www.proteinatlas.org/humanproteome/secretome).

The targeting component can bind the cell surface receptor or other cell surface molecule with an affinity (dissociation constant) of less than 10 μM at near-neutral pH.

Accordingly, the targeting component of a Seldeg can include any type of molecule that is configured to specifically bind to a cell surface receptor or other cell surface molecule. Such molecules can include proteins, protein fragments, polynucleotides such as ribonucleic acids or deoxyribonucleic acids, polypeptides, polysaccharides, lipids, amino acids, peptides, sugars and/or other small or large molecules and/or polymers identifiable by skilled persons upon reading of the present disclosure. For example, the targeting component of a Seldeg can include a polynucleotide that is a ligand for a cellular receptor.

The Seldeg can comprise at least a first targeting component and a second targeting component, wherein the protein or protein fragment of the first targeting component is configured to bind to a different cell surface receptor or a different cell surface molecule than the protein or protein fragment of the second targeting component.

As shown in FIG. 1, a Seldeg 20 may reversibly bind to cell surface receptor or other molecule 30 on the surface of a cell 10. A target antigen-specific antibody 40, present in extracellular space 50, may reversibly bind to Seldeg 20. This binding typically occurs at near-neutral pH, such as at a pH greater than 6.8 and less than 7.5, because that is the typical pH of extracellular space 50. Non-target antibodies 60 do not bind to Seldeg 20, or bind with such low affinities that any binding is non-specific. Cell surface receptor or molecule 30 with attached Seldeg 20 and target antigen-specific antibody 40 are internalized into the cell 10 through receptor-mediated uptake into endosome 70 via pathway A. The receptor or other molecule can be recycled back to the surface of the cell. Accordingly, on pathway B, receptor or molecule 30 with attached Seldeg 20 and target antigen-specific antibody 40 are cycled back to the surface of cell 10. Target antigen-specific antibody 40 may then be released and may reattach from Seldeg 20 to the same or another Seldeg, or it may remain attached. Similarly Seldeg 20 may then be released from receptor or molecule 30 and may reattach to the same or another cell surface receptor or molecule. For some Seldegs, the complex of Seldeg 20 and antibody 40 may dissociate from the receptor or other molecule 30 in the early or late endosome due to the acidic pH or low $Ca^{2+}$ concentrations in this compartment (pathway C). Accordingly, in pathway D, receptor or cell surface molecule may recycle back to the cell surface whereas the Seldeg 20 bound to antibody 40 enters the lysosomes and is degraded into fragments 80 in pathway E. For some Seldegs, at some point following internalization into cell 10, receptor or molecule 30 with attached Seldeg 20 and target antigen-specific antibody 40 enters the late endosomal/lysosomal in pathway F, in which at least target antigen-specific antibody 40 is degraded into fragments 80. This entry into lysosomes is expected to be increased if Seldeg 20 cross-links receptor or molecule 30 into dimers or higher order aggregates.

Through this mechanism of selective depletion, Seldegs target and selectively deplete antigen-specific antibodies from the body without adversely affecting the levels of antibodies of non-targeted specificities.

In particular, Seldegs as described herein can target and selectively deplete antigen-specific antibodies from the body without having an adverse clinical effect in the patient due to the depletion of antibodies of non-targeted specificities. Such adverse clinical effects include, for example, immunosuppression, and symptoms thereof, such as pinkeye, bronchitis, ear infections, sinus infections, cold, diarrhea, pneumonia, yeast infection, meningitis, skin infections, and other opportunistic infections, particularly opportunistic infection normally controlled through anti-body mediated immune responses; and blood disorders, such as low platelet counts or anemia, and hypogammaglobulinemia and symptoms thereof, such as abdominal pain, bloating, nausea, vomiting, diarrhea, or weight loss.

In general, Seldegs according to this disclosure are configured to specifically bind a cell surface receptor/molecule at near-neutral pH via a targeting component and also specifically bind to an antigen-specific antibody at near-neutral pH via an antigen component that is fused directly or indirectly to the targeting component. The term "specifically bind" as used herein refers to a detectable selective intermolecular interaction between the targeting component and the cell surface receptor/molecule, or between the antigen component and the antigen-specific antibody. For example, to specifically bind, the antigen needs to show a detectable interaction with the antibodies that are being targeted, whilst not showing a detectable interaction with other antibodies. Techniques for detecting specific binding are known within the art, such as ELISA, surface plasmon resonance analysis and other methods identifiable by skilled persons Accordingly, Seldegs allow at least a portion of the antigen-specific antibody in the circulation of a patient to be internalized into cells that express the targeted cell surface receptor or targeted other cell surface molecule and thereafter intracellularly degraded.

Seldegs according to this disclosure may avoid immune responses by containing one copy, otherwise referred herein as "one molecule", of each type of antigen, antigen fragment or antigen mimetic, per Seldeg, which in combination with the insertion of mutations to reduce or eliminate Fc gamma receptor binding and/or complement binding, is expected to decrease antibody cross-linking and the formation of potentially inflammatory immune complexes. In particular, at least 99% of Seldegs, at least 99.5% of Seldegs, or at least 99.9% of Seldegs may contain only one copy of antigen, antigen fragment, or antigen mimetic per Seldeg at near-neutral pH. Other Seldegs according to the present disclosure can contain more than one molecule of an antigen, antigen fragment, or antigen mimetic. The bivalent nature of the antibodies that are bound by Seldegs may result in complexes of two Seldeg molecules per antibody, which through target receptor dimerization is expected to increase the efficiency of lysosomal delivery of Seldeg-antibody complexes.

Seldegs can include at least a first antigen component and a second antigen component, wherein the one molecule of the antigen, antigen fragment or antigen mimetic of the first antigen component is different to the one molecule of the antigen molecule, antigen fragment or antigen mimetic of the second antigen component. Accordingly, Seldegs comprising at least a first antigen component and a second antigen component allow clearance of antigen-specific antibodies of more than one specificity.

Seldegs can include at least a first antigen component and a second antigen component, wherein the one molecule of the antigen, antigen fragment or antigen mimetic of the first antigen component is the same as the one molecule of the antigen molecule, antigen fragment or antigen mimetic of the second antigen component.

Accordingly, Seldegs can include, for example, one or more antigen components fused to a C-terminus and/or an N-terminus of a targeting component, wherein the one molecule of the antigen mimetic antigen components of the respective antigen components of the respective antigen components can be the same or different.

In addition, Seldegs may contain human or humanized proteins or protein fragments to avoid or decrease the possibility of an immune reaction to the Seldeg when administered to a human. The antigen, antigen fragment, or antigen mimetic of the antigen component is preferably a human protein or protein fragment for administration of the Seldeg to a human. The targeting component is also preferably a human protein or protein fragment, such as a human antibody fragment or human albumin or albumin fragment, or a humanized antibody or humanized antibody fragment for administration of the Seldeg to a human. If a Seldeg is developed for use in a non-human animal, then proteins or protein fragments derived from or engineered to be immunologically compatible with that animal may be used instead.

FIG. 2A is a schematic representation of the activity of a Seldeg 20*a* including antigen 100 fused to a targeting component having the Fc fragment of IgG 110. As understood by persons skilled in the art, the Fc fragment of an IgG is all of the lower base of the antibody's Y-shape, which is the sulfhydryl-bridged hinge region and the CH2 and CH3 domains. Seldegs can have an Fc fragment that does not have the hinge region, or the hinge region does not have sulfydryl bridges. Fc fragment 110 allows Seldeg 20*a* to bind an FcRn molecule on an FcRn-expressing cell. In the example shown in FIG. 2A, antigen 100 may be fused to Fc fragment 110*a* at the N-terminus of the hinge-$CH_2$—$CH_3$ 120. When antigen 100 is fused to Fc fragment 110*a* and the resulting antigen-Fc fragment dimerizes with another Fc fragment 110*b* lacking an antigen, using the knobs-into-holes strategy (for example, as described in Moore, G. L., Bautista, C., Pong, E., Nguyen, D. H., Jacinto, J., Eivazi, A., Muchhal, U. S., Karki, S., Chu, S. Y., Lazar, G. A., 2011). A novel bispecific antibody format enables simultaneous bivalent and monovalent co-engagement of distinct target antigens. MAbs 3, 546-557), a heterodimeric Seldeg molecule 20*a* as shown is produced. Seldeg 20*a* has an Fc fragment with a monomeric display of antigen 100, which avoids the formation of multimeric immune complexes that can cause inflammation and other adverse effects. Although Seldegs containing only antigen 100 fused to Fc fragment 110*a* may be produced and used in some circumstances, due to the tendency of Fc fragment to dimerize, a dimer will typically be produced. In order to avoid Fc fragment dimers in which both Fc fragments 110*a* have a fused antigen 100, which can lead to the formation of multimeric immune complexes, Seldegs are designed with knobs-into-holes mutations and/or electrostatic steering mutations (for example, as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010) Enhancing antibody Fc heterodimer formation through electrostatic steering effects: applications to bispecific molecules and monovalent IgG. J Biol Chem 285, 19637-19646) to promote heterodimer formation, so there is only one Fc with one antigen fused. Other approaches can also be used to generate heterodimers, such as the insertion of a $(G_4S)_{13}$ linker peptide between the C-terminus of the antigen-Fc fusion and N-terminus of a second Fc fragment (for example, as described in Zhou, L., Wang, H-Y., Tong, S., Okamoto, C. T., Shen, W-C., Zaro, J. L. (2016) Single chain Fc-dimer-human growth hormone fusion protein for improved drug delivery. Biomaterials, 117, 24-31]. DNA and protein sequences of several examples of Seldegs comprising knobs-into-holes mutations, electrostatic steering mutations, and/or arginine mutations or other mutations that reduce Fc gamma receptor and complement binding are described in Example 10.

Additional examples of knobs-into-holes mutations include Y349T/T394F: S364H/F405A and Y349T/F405F: S364H/T394F (for example as described in Moore, G. L., Bautista, C., Pong, E., Nguyen, D. H., Jacinto, J., Eivazi, A., Muchhal, U. S., Karki, S., Chu, S. Y., Lazar, G. A. (2011) A novel bispecific antibody format enables simultaneous bivalent and monovalent co-engagement of distinct target antigens. MAbs 3, 546-557) and T366W:T366S:L368A/Y407V (for example as described in Atwell, S., Ridgway, J. B. B., Wells, J. A., Carter, P (1997) Stable heterodimers from remodeling the domain interface of a homodimer using a phage display library. J. Mol. Biol., 270, 26-35) among others identifiable by persons skilled in the art. The residue numbering of these exemplary knobs into holes mutations refers to the EU antibody numbering system, as would be understood by persons skilled in the art.

Additional examples of electrostatic steering mutations include E356K/D399K:K392D/K409D and K409D/K370D: D357K/D399K (for example as described in Gunasekaran, K., Pentony, M., Shen, M., Garrett, L., Forte, C., Woodward, A., Ng, S. B., Born, T., Retter, M., Manchulenko, K., Sweet, H., Foltz, I. N., Wittekind, M., Yan, W. (2010). Enhancing antibody Fc heterodimer formation through electrostatic steering effects: applications to bispecific molecules and monovalent IgG. J Biol Chem 285, 19637-19646.) among others identifiable by persons skilled in the art. The residue numbering of these exemplary electrostatic steering mutations refers to the EU antibody numbering system, as would be understood by persons skilled in the art.

Additional examples of arginine mutations or other mutations to reduce binding to Fc gamma receptors and complement (C1q) include G236R/L328R (for example as described in Horton, H. M., Bernett, M. J., Pong, E., Peipp, M., Karki, S., Chu, S. Y., Richards, J. O., Vostiar, I., Joyce, P. F., Repp, R., Desjarlais, J. R., Zhukosky, E. (2010) Potent in vitro and in vivo activity of an Fc-engineered anti-CD19 monoclonal antibody against lymphoma and leukemia. Cancer Res., 68, 8049-8057; Moore, G. L., Bautista, C., Pong, E., Nguyen, D. H., Jacinto, J., Eivazi, A., Muchhal, U. S., Karki, S., Chu, S. Y., Lazar, G. A. (2011). A novel bispecific antibody format enables simultaneous bivalent and monovalent co-engagement of distinct target antigens. MAbs 3, 546-557), N297A or N297Q (for example as described in Tao, M-H., Morrison, S. L. (1989) Studies of aglycosylated chimeric mouse-human IgG: role of carbohydrate in the structure and effector functions mediated bu the human IgG constant region. J. Immunol., 143, 2595-2601; Lux, A., Yu, X., Scanlan, C. N., Nimmerjahn, F. (2013) Impact of immune complex size and glycosylation on IgG binding to human FcγRs. J. Immunol., 190, 4315-4323), D265A (for example as described in Lux, A., Yu, X., Scanlan, C. N., Nimmerjahn, F. (2013) Impact of immune complex size and glycosylation on IgG binding to human FcγRs. J. Immunol., 190, 4315-4323; Clynes, R. A., Towers, T. L., Presta, L. G., Ravetch, J. V. (2000) Inhibitory Fc receptors modulate in vivo cytotoxicity against tumor targets. Nat. Med. 6, 443-446), L234A/L235A (for example as described in Wines, B. D., Powell, M. S., Parren, P. W. H. I., Barnes, N., Hogarth, P. M. (2000) The IgG Fc contains distinct Fc receptor (FcR) binding sites: the leukocyte receptors FcγRI and FcγRIIa bind to a region in the Fc distinct from that recognized by neonatal FcR and protein A. J. Immunol., 164, 5313-5318), and L234A/L235A/P329G (for example as described in Schlothauer, T., Herter, S., Koller, C. F., Grau-Richards, S., Steinhart, V., Spick, C., Kubbies, M., Klein, C., Umana, P., Mossner, E. (2016) Novel human IgG1 and IgG4 Fc-engineered antibodies with completely abolished effector functions. PEDS, 29, 457-466), among others identifiable by persons skilled in the art. The residue numbering of these exemplary arginine mutations or other mutations to reduce binding to Fc gamma receptors and complement (C1q) refers to the EU antibody numbering system, as would be understood by persons skilled in the art.

Other mutations to ablate FcγR and/or complement binding that target residues at, or in proximity to, the location of the FcγR and complement binding sites can be used. These sites on the Fc region of IgG have been localized (for example, as described in Jefferis, R., Lund, J. (2002) Interaction sites on human IgG-Fc for FcγR: current models. Immunol. Letts., 82, 57-65; Duncan, A. R., Winter, G. (1988) The binding site for C1q on IgG. Nature, 332, 738-740; Idusogie, E. E., Presta, L. G., Gazzano-Santoro, H., Totpal, K., Wong, P. Y., Ultsch, M., Meng, G., Mulkerrin, M. G. (2000) Mapping of the C1q binding site on rituxan, a chimeric human antibody with a human IgG1 Fc. J. Immunol., 164, 4178-4184; Hogarth, P. M., Anania, J., Wines, B. D. (2014) The FcγR of humans and non-human primates and their interaction with IgG: implications for induction of inflammation, resistance to infection and the use of therapeutic monoclonal antibodies. Curr. Top. Microbiol. Immunol., 382, 321-352).

Seldegs may include Fc fragments derived from immunoglobulin classes or isotypes that do not bind, or have very weak binding, to Fc gamma receptors or complement such as human IgG2 or human IgG4.

For some applications such as diagnostic imaging, Seldegs may include Fc fragments with binding sites for Fc gamma receptors and/or complement to increase inflammatory responses against the antigen that is present in the Seldeg.

Fc fragment 110 may be modified to substantially increase its binding affinity for FcRn at near-neutral pH as compared to unmodified Fc fragments. For example, the dissociation constant between Fc fragment 110 and FcRn at a pH greater than 6.8 and less than 7.5 may be less than 10 µM as determined by surface plasmon resonance or other biophysical method. However, Fc fragment 110 may have a similar or increased affinity for FcRn as compared to an unmodified Fc fragment at acidic endosomal pH (about 6.0), or it may be modified to have a much lower or negligible binding affinity for FcRn at endosomal pH as compared to an unmodified Fc fragment. This increase in binding affinity at near neutral pH allows each Seldeg to cause its bound target antigen-specific antibody to be efficiently internalized and trafficked into late endosomes or lysosomes in FcRn-expressing cells. Enhanced binding affinity of the Fc fragment for FcRn may be achieved by insertion of mutations. Naturally-occurring IgGs have a substantially higher binding affinity for FcRn at acidic pH levels as opposed to near-neutral pH. This property is essential for the recycling and transport of IgG within FcRn-expressing cells. In contrast, an increase in binding affinity for FcRn at pH 7.4, for example, results in receptor-mediated internalization into cells and lysosomal delivery.

Fc fragment 110 may also be modified to eliminate or substantially reduce the binding affinity for Fc gamma receptors and complement (C1q). This modification prevents inflammatory responses caused by the formation of multimeric immune complexes. For example, as described in Example 10, the Fc regions can be mutated (G236R/L328R; EU numbering) (for example as described in Moore, G. L., Bautista, C., Pong, E., Nguyen, D. H., Jacinto, J., Eivazi, A., Muchhal, U. S., Karki, S., Chu, S. Y., Lazar, G. A. (2011). A novel bispecific antibody format enables simultaneous bivalent and monovalent co-engagement of distinct target antigens. MAbs 3, 546-557) (EU numbering), herein also referred to as "arginine mutations", so that they do not bind Fc gamma receptors. In Example 10, these mutations correspond to residues 22 and 114 of Fc-Syt1 (see SEQ ID NO:10), and residues 114 and 236 of MOG-Seldeg-PS (see SEQ ID NO: 8). Other examples of mutations that substantially reduce or ablate binding to Fc gamma receptors and complement include N297A or N297Q) (EU numbering; for example as described in Tao, M-H., Morrison, S. L. (1989) Studies of aglycosylated chimeric mouse-human IgG: role of carbohydrate in the structure and effector functions mediated by the human IgG constant region. J. Immunol., 143, 2595-2601; Lux, A., Yu, X., Scanlan, C. N., Nimmerjahn, F. (2013) Impact of immune complex size and glycosylation on IgG binding to human FcγRs. J. Immunol., 190, 4315-4323), D265A (for example as described in Lux, A., Yu, X., Scanlan, C. N., Nimmerjahn, F. (2013) Impact of immune complex size and glycosylation on IgG binding to human FcγRs. J. Immunol., 190, 4315-4323; Clynes, R. A., Towers, T. L., Presta, L. G., Ravetch, J. V. (2000) Inhibitory Fc receptors modulate in vivo cytotoxicity against tumor targets. Nat. Med. 6, 443-446), L234A/L235A (for example as described in Wines, B. D., Powell, M. S., Parren, P. W. H. I., Barnes, N., Hogarth, P. M. (2000) The IgG Fc contains distinct Fc receptor (FcR) binding sites: the leukocyte receptors FcγRI and FcγRIIa bind to a region in the Fc distinct from that recognized by neonatal FcR and protein A. J. Immunol., 164, 5313-5318), L234A/L235A/P329G (for example as described in Schlothauer, T., Herter, S., Koller, C. F., Grau-Richards, S., Steinhart, V., Spick, C., Kubbies, M., Klein, C., Umana, P., Mossner, E. (2016) Novel human IgG1 and IgG4 Fc-engineered antibodies with completely abolished effector functions. PEDS, 29, 457-466), (EU numbering) among others identifiable by persons skilled in the art. A reduction in binding affinity for Fc gamma receptors of at least 10-fold is preferred.

Figure 1:
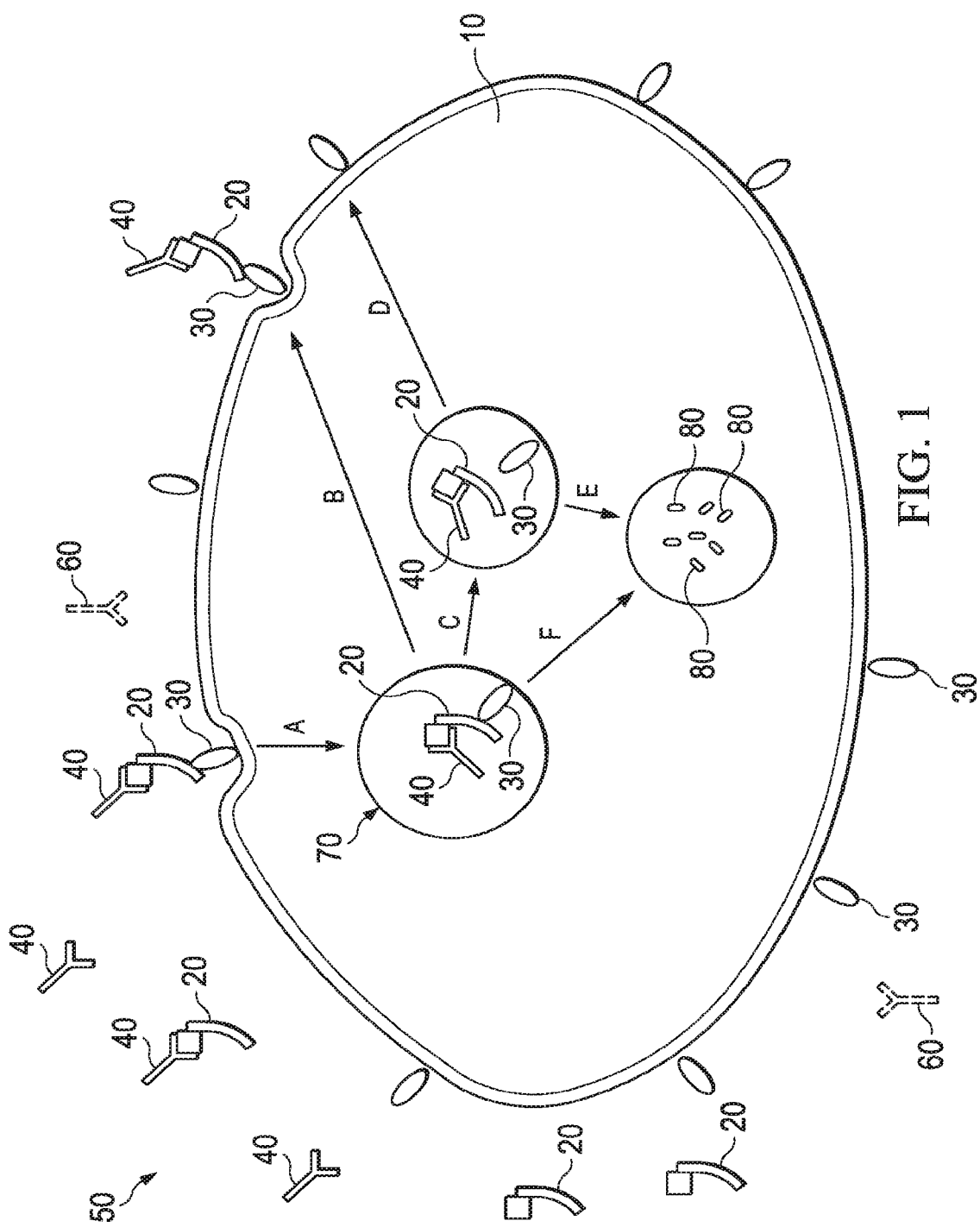
Figure 2A:
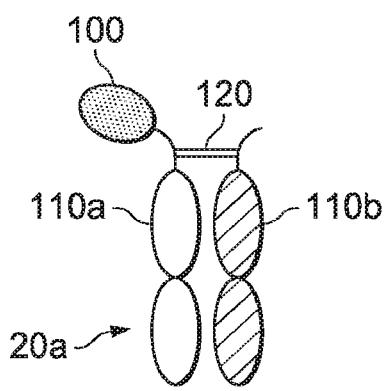
FIG. 2F is a schematic diagram of a Seldeg including an antigen fused to a N-terminal location of an Fc fragment and protein or protein fragments that bind to a cell surface protein or cell surface receptor to the fused C-termini of the Fc fragment.
FIG. 2G is a schematic diagram of a Seldeg including an antigen fused to a C-terminal location of an Fc fragment and protein or protein fragments that bind to a cell surface protein or cell surface receptor fused to the N-termini of the Fc fragment.
FIG. 2H is a schematic diagram of a Seldeg including an antigen fused to a C-terminal location of an antibody that binds to a cell surface protein or cell surface receptor.
FIG. 2I is a schematic diagram of a Seldeg including an antigen fused to a C-terminal location of an Fc fragment and scFv fragments that bind to a cell surface protein or cell surface receptor fused to the N-termini of the Fc fragment.
FIG. 2J is a schematic diagram of a Seldeg including an antigen fused to a N-terminal location of an Fc fragment and scFv fragments that bind to a cell surface protein or cell surface receptor fused to the C-termini of the Fc fragment.
FIG. 2K is a schematic diagram of a Seldeg including two different antigens fused to the N-terminal locations of an Fc fragment.
FIG. 2L is a schematic diagram of a Seldeg comprising two different antigens fused to the N-terminal locations of an Fc fragment and protein or protein fragments that bind to a cell surface protein or cell surface receptor fused to the C-termini of the Fc fragment.
FIG. 2M is a schematic diagram of a Seldeg comprising two antigen molecules fused to the N-terminal locations of an Fc fragment.
FIG. 2N is a schematic diagram of a Seldeg comprising two antigen molecules fused to the N-terminal locations of an Fc fragment and protein or protein fragments that bind to a cell surface protein or cell surface receptor fused to the C-termini of the Fc fragment.
Figure 2B:
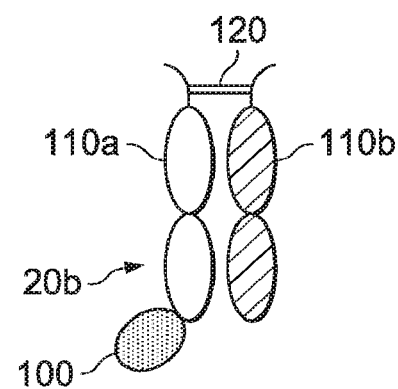
Figure 2C:
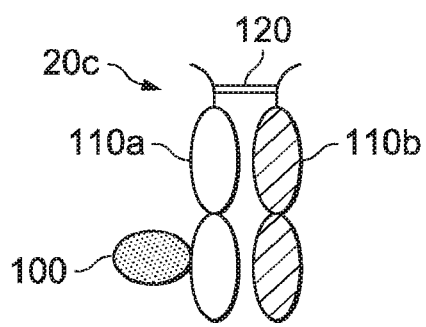

As shown in FIG. 2B, in Seldeg 20b antigen 100 may be attached to Fc fragment 110a at another terminal location, or as shown in FIG. 2C, in Seldeg 20c, antigen 100 may be attached at a non-terminal location. Any location that does not prevent specific FcRn binding is suitable. Such locations include amino acid residues that are sufficiently distant from the FcRn interaction site (encompassing residues 252-256, 309-311, 433-436 at the CH2-CH3 domain interface; EU numbering so as not to either directly or sterically block FcRn binding, as would be identifiable by skilled persons.

Antigen 100 may be fused to Fc fragment 110 in any suitable manner, including attachment via a chemical reaction, attachment through a linker, or during formation of a single combined antigen-Fc fragment protein. Examples of chemical coupling that could be used are: amine-to-amine (NHS esters), sulfhydryl-to-sulfydryl (maleimide), amine-to-sulfhydryl (NHS ester/maleimide), sulfhydryl-to-carbohydrate (maleimide/hydrazide), or attachment to via an unnatural amino acid with the desired chemical reactivity. This unnatural amino acid can be inserted during recombinant production of the Fc fragment and/or antigen. Polyethyleneglycol (PEG) spacers can also be inserted between the chemically conjugated proteins, protein fragments or other molecules. Possible linkers include repeats of glyine-serine linker peptides, or other more rigid linker peptides, that are encoded in the recombinant expression plasmid for the antigen-Fc fusion. Linkage chemistry, sites of linkage and choice of peptide can be guided by molecular modeling, and can be designed to minimize loss of binding activity of the antigen or the protein/protein fragment targeting the cell surface molecule, as would be understood by skilled persons.

FIG. 2D is a schematic representation of Seldeg 20*d* in which antigen 100 is attached to antibody variable region 130. Antibody variable region 130 specifically binds to a cell surface receptor or cell surface molecule. Antibody variable region 130 may be an entire variable region or a fragment thereof, so long as it can specifically bind to a cell surface receptor or cell surface molecule. Antibody variable region 130 may include portions of a non-variable region of an antibody that is configured to bind to a cell surface receptor or cell surface molecule. For example, antibody variable region 130 may be a single-domain antibody (sdAb) or camelid-derived VHH domain (also commonly referred to as a nanobody). Such variable regions have the overall fold of an immunoglobulin domain, comprising two anti-parallel β-sheets, and can also include domains from other members of the immunoglobulin superfamily such as T cell receptor variable domains, constant region domains of antibodies or domains of the coreceptor, CD4, among others identifiable by persons skilled in the art. Antibody variable region 130 may be present as a monomer as shown in FIG. 2D, or as a multimer. For example, if antibody variable region 130 is present as a nanobody, it may be engineered with a linker peptide such as GSSGGSGGGGS (SEQ ID NO:35) between the C-terminus of the first nanobody and the N-terminus of the second nanobody to form a dimer, resulting in increased binding avidity for target receptor/molecule. If antibody variable region 130 is a nanobody or another protein that is engineered to form multimers, variants without antigen 100 may be included during Seldeg formation so that multimers contain only one copy of antigen 100, just as described above for Seldegs containing Fc fragments. Antibody variable regions can also include heterodimers of heavy chain variable (VH) domains linked by peptide linkers to light chain variable (VL) domains to form scFv fragments. The linker sequences that are used to link VH and VL domains are well known to those with skill in the art and include the GGGGSGGGGSGGGGS [$(G_4S)_3$](SEQ ID NO:36) sequence that connects the C-terminus of the VH domain to the N-terminus of the VL domain. In some embodiments, the C-terminus of the VL domain can be connected to the N-terminus of the VH domain with similar linker sequences. ScFvs that bind to a cell surface receptor or other cell surface molecule can be isolated from libraries of scFvs using phage display, yeast display or other antibody display approaches. The targeting protein component of a Seldeg could also include Fab fragments of an antibody that can be isolated from libraries of Fab fragments using phage display, yeast display etc. For nanobodies, scFvs and Fab fragments, affinities for binding to a cell surface receptor or cell surface molecule can be increased by randomly mutating residues in the complementarity determining regions (CDRs), or by using error-prone polymerase chain reaction, to generate libraries of mutated nanobodies or variable domains. Exemplary CDR residues that would be targeted are those in CDR3 of the light chain variable domain (residues 89-97; Kabat numbering) and CDR3 of the heavy chain variable domain (residues 95-102; Kabat numbering). These libraries can be displayed on phage or yeast and higher affinity variants selected using approaches known to those with skill in the art.

Figure 2D:
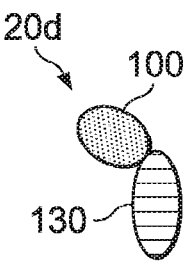

Although FIG. 2D illustrates antigen 100 at a terminal location of antibody variable region 130, it may instead be located at a non-terminal location. Antigen 100 may be fused to antibody variable region 110 in any suitable manner, including attachment via a chemical reaction, attachment through a linker, or during formation of a single combined antigen-antibody variable region fusion protein.

Figure 2E:
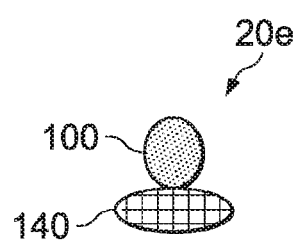

A Seldeg may also contain an antigen component fused to targeting component that includes a protein other than an antibody or antibody fragment, providing that this protein is configured to bind to a cell surface receptor or other cell surface molecule. For example, as shown in FIG. 2E, Seldeg 20e includes antigen 100 fused to albumin or an albumin fragment 140 able to bind FcRn. The albumin or albumin fragment may be mutated or modified so that it binds with increased affinity to FcRn. For example, mutations can be inserted into the FcRn binding domain (DIII) of (human serum) albumin using error prone PCR followed by display of libraries of mutated albumin variants on yeast or phage, and selection of higher affinity variants. Alternatively, higher affinity variants can be generated by mutating residues at or near the albumin:FcRn interface and either selecting or screening for albumin variants with increased binding affinity. Although FIG. 2E illustrates antigen 100 at a non-terminal location of albumin or albumin fragment 140, it may instead be located at a terminal location. Antigen 100 may be fused to albumin or albumin fragment 140 in any suitable manner, including attachment via a chemical reaction, attachment through a linker, or during formation of a single combined antigen-FcRn-binding protein.

Figure 2F:
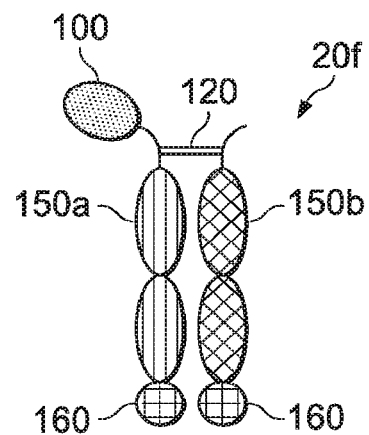
Figure 2G:
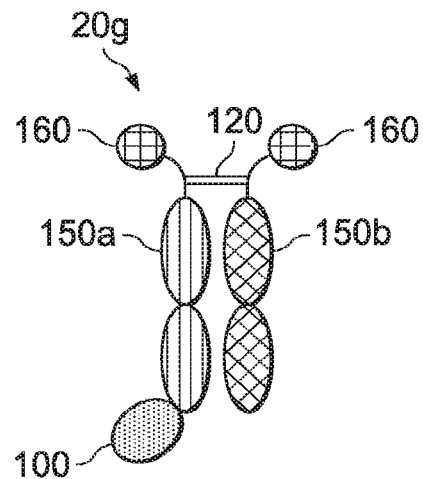

FIG. 2F is a schematic representation of exemplary Seldeg 20f including antigen 100 attached to the N-terminus of an Fc fragment 150. In the example shown in FIG. 2F, protein or protein fragments 160 that bind to a cell surface receptor or cell surface molecule are attached to the C-terminus of Fc fragment 150a. For example, the protein or protein fragment may be the C2A domain of synaptotagmin that binds to phosphatidylserine (PS). Fc fragment 150 can be engineered to bind to FcRn with increased affinity and may be mutated so that it binds to Fc gamma receptors and complement with very low or no detectable binding affinity. In order to avoid Fc fragment homodimers having two Fc fragments 150a with fused antigen 100, which can lead to the formation of multimeric immune complexes, Seldegs as shown in FIG. 2F are designed with knobs-into-holes mutations and/or electrostatic steering mutations to promote heterodimer formation, so there is only one Fc with one Fc-antigen. In FIG. 2F, both Fc fragments 150a and 150b have proteins or protein fragments that bind to the cell surface protein or other cell surface molecule fused to them; alternatively, only one such protein or protein fragment may be present. In the exemplary Seldeg shown in FIG. 2G, both the antigen 100 and protein or protein fragments 160 that bind to a cell surface receptor or cell surface molecule are fused to the C- and N-termini of the Fc fragments 150a and 150b, respectively, to generate Seldeg 20g.

Figure 2H:
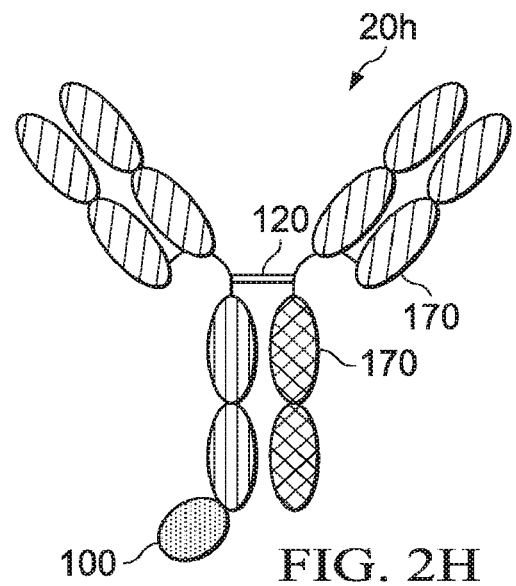

FIG. 2H is a schematic representation of exemplary Seldeg 20h including antigen 100 attached to the C-terminus of an antibody 170 that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2H are designed with knobs-into-holes mutations and/or electrostatic steering mutations to promote heterodimer formation, so there is only one antibody heavy chain per antibody molecule with attached antigen 100. Both Fab fragments of the antibody may bind to the same cell surface protein or other cell surface molecule; alternatively, they could bind to two or more different cell surface proteins or molecules.

Figure 2I:
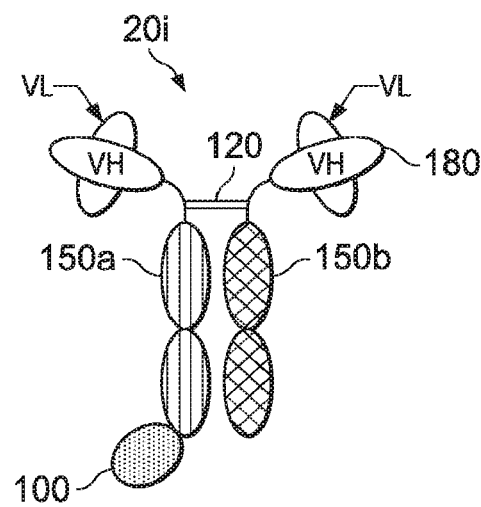

FIG. 2I is a schematic representation of exemplary Seldeg 20i comprising antigen 100 attached to the C-terminus of a scFv (180)-Fc fusion that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2I are designed with knobs-into-holes mutations and/or electrostatic steering mutations to promote heterodimer formation, so there is only one antibody heavy chain-scFv fusion per molecule with attached antigen 100. Both scFv fragments of the antibody may bind to the same cell surface protein or other cell surface molecule; alternatively, they could bind to two or more different cell surface proteins or molecules.

Figure 2J:
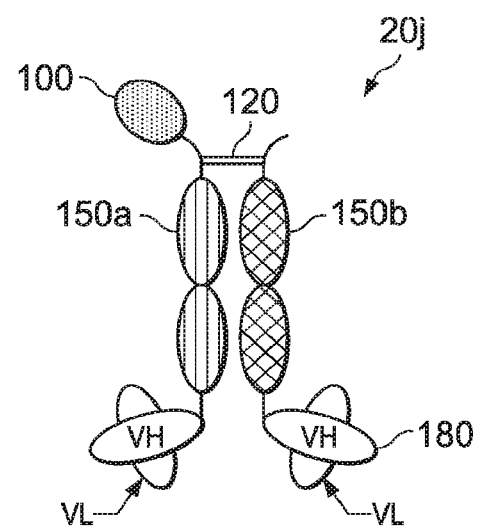

FIG. 2J is a schematic representation of exemplary Seldeg 20j comprising antigen 100 attached to the N-terminus of an Fc-scFv (180) fusion that binds to a cell surface protein or cell surface molecule. The Fc fragment (Fc) in the antibody can be engineered to bind to FcRn with increased affinity and may be mutated so that it binds to Fc gamma receptors and complement with very low or no detectable binding affinity. In order to avoid antibody homodimers in which both Fc fragments have a fused antigen 100, which can lead to the formation of multimeric immune complexes, Seldegs as shown in FIG. 2I are designed with knobs-into-holes mutations and/or electrostatic steering mutations to promote heterodimer formation, so there is only one antibody heavy chain-scFv fusion per molecule with attached antigen 100. Both scFv fragments of the antibody may bind to the same cell surface protein or other cell surface molecule; alternatively, they could bind to two or more different cell surface proteins or molecules.

Figure 2K:
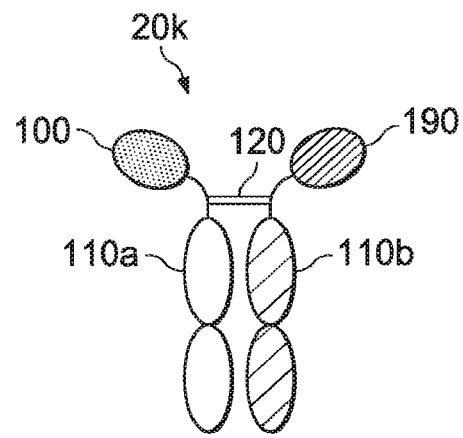

As shown in FIG. 2K, in exemplary Seldeg 20k two antigen components (100, 190) may be attached to a targeting component, for example Fc fragment 110a and Fc fragment 110b at an N-terminal or other location to generate a Seldeg that can clear antigen-specific antibodies of different specificities. Seldegs as shown in FIG. 2K are designed with knobs-into-holes mutations and/or electrostatic steering mutations to promote heterodimer formation, so there is an antigen molecule of each type (100, 190) in each Seldeg molecule.

Figure 2L:
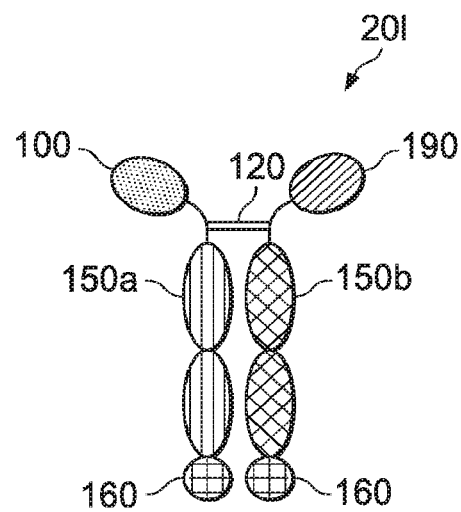

FIG. 2L is a schematic representation of exemplary Seldeg 201 comprising antigen 100 and antigen 190 attached to the N-termini of an Fc fragment 150. In the exemplary embodiment shown in FIG. 2L, protein or protein fragments 160 that bind to a cell surface receptor or cell surface molecule are attached to the C-termini of Fc fragment 150a and 150*b*. Seldegs as shown in FIG. 2L are designed with knobs-into-holes mutations and/or electrostatic steering mutations to promote heterodimer formation, so there is an antigen molecule of each type (100, 190) in each Seldeg molecule. In FIG. 2L, both Fc fragments 150*a* and 150*b* have proteins or protein fragments that bind to the cell surface protein or other cell surface molecule fused to them, but in other embodiments, only one such protein or protein fragment may be present.

Figure 2M:
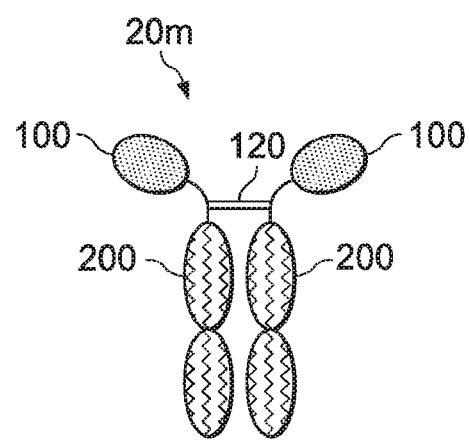

As shown in FIG. 2M, in exemplary Seldeg 20*m* two molecules of the same antigen (100) may be attached to Fc fragment 200 at N-terminal or other locations to generate exemplary Seldeg 20*m*. This exemplary Seldeg is a homodimer that contains mutations to enhance binding to FcRn, and does not contain knobs-into-holes and/or electrostatic steering mutations.

Figure 2N:
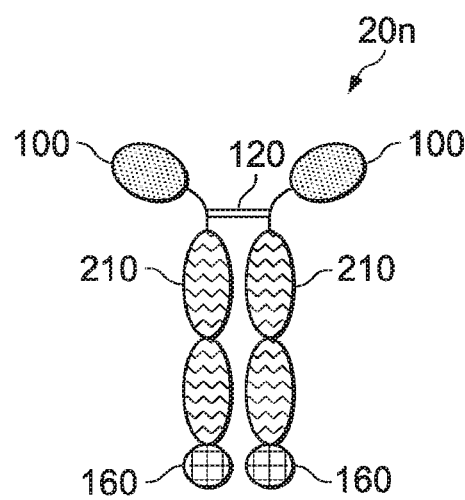

FIG. 2N is a schematic representation of exemplary Seldeg 20*n* comprising two molecules of the same antigen (100) attached to the N-termini of an Fc fragment 210. In the exemplary embodiment shown in FIG. 2N, protein or protein fragments 160 that bind to a cell surface receptor or cell surface molecule are attached to the C-terminus of Fc fragment 210. This exemplary Seldeg is a homodimer and does not contain knobs-into-holes and/or electrostatic steering mutations. In FIG. 2N, the homodimeric Fc fragment 200 has proteins or protein fragments that bind to the cell surface protein or other cell surface molecule fused to both polypeptide chains, but in other embodiments, only one such protein or protein fragment may be present.

For Seldegs that target FcRn, similar principles may be applied to other proteins able to bind FcRn. In addition, the FcRn-targeting Seldeg or methods of forming it may be affected by properties of the FcRn-binding protein. Although albumin tends to not form dimers or other multimers, other FcRn-binding proteins may, in which case the final Seldeg may be formed in a manner to those containing antibody fragments so that each Seldeg contains only one copy of the antigen. In the examples shown in FIGS. 2A, 2B, 2C, 2F, 2G, 2H, 2I, 2J, 2K, 2L, the Seldeg has two antibody Fc fragments that are engineered with knobs-into-holes mutations and/or electrostatic steering mutations to drive the formation of heterodimers comprising one antigen linked to one Fc fragment and one Fc fragment with no antigen attached. The Fc fragment can be further engineered to bind to FcRn with increased affinity at near neutral pH (FIGS. 2A, 2B, 2C, 2K, 2M) or connected to one or more proteins, scFv fragments, Fab fragments or other molecules that target one or more cell surface receptors or molecules (FIGS. 2F, 2G, 2H, 2I, 2J, 2L, 2N). The Fc fragments in the examples shown in FIGS. 2F, 2G, 2H, 2I, 2J, 2L, 2N can also be engineered to bind with higher affinity to FcRn so that they target both FcRn and one or more cell surface receptors or molecules.

Albumin binds more strongly to FcRn at acidic pH than at neutral pH. However, albumin may also be modified to alter its binding affinities at near-neutral or endosomal pH to encourage degradation of the target antigen-specific antibody and recycling of the Seldeg. Similarly, antibody variable region FcRn-binding proteins may be affected by pH in a manner specific to that protein, but they may still be modified to alter its binding affinities at near-neutral or endosomal pH to encourage degradation of the target antigen-specific antibody. These FcRn-binding proteins can be isolated from libraries of immunoglobulin variable domains, scFv (VH:VL heterodimers in which VH and VL domains are connected to each other by linker peptides such as GGGGSGGGGSGGGGS)(SEQ ID NO:36) or Fab fragments using phage display, yeast display or other technologies known to those with skill-in-the-art. These libraries can either be derived from naturally occurring antibody variable genes, or can be generated using approaches that result in 'semi-synthetic' libraries wherein complementarity determining regions (CDRs) are produced using randomized oligonucleotide sequences. Further increases to their affinities can be achieved by, for example, inserting random mutations in the CDRs using error-prone PCR followed by selection using phage display or yeast display. Exemplary CDR residues that would be targeted are those in CDR3 of the light chain variable domain (residues 89-97; Kabat numbering) and CDR3 of the heavy chain variable domain (residues 95-102; Kabat numbering). Similar methods can be used to isolate antibody-based proteins or scaffold-based proteins that bind to other cell surface receptors/molecules.

Seldegs may include any targeting component that is configured to specifically bind to a receptor or other molecule on the cell surface (FIG. 2D, 2E, 2F, 2G, 2H, 2I, 2J, 2L, or 2N). The targeting component is fused directly or indirectly (e.g., via a linker) to an antigen component having one molecule of each type of antigen, antigen fragment or antigen mimetic to reduce antibody-mediated crosslinking. The term "type of antigen" as used herein refers to an antigen that binds to a specific antibody. Accordingly, a Seldeg can include more than one antigen type, wherein each Seldeg has only one molecule of each antigen type. If the targeting protein contains an immunoglobulin-derived Fc fragment, the Fc region can be mutated so that it does not bind, or binds at substantially reduced levels, to Fc gamma receptors and complement. Several different possible configurations of Seldegs are shown in FIG. 2A-N; these are shown as examples and are not limiting, since multiple other configurations can also be envisaged by those with skill-in-the-art.

Seldegs may include Fc fragments that bind to Fc gamma receptors and complement. The presence of the Fc gamma and complement binding sites may be desired in the context of particular application areas, when an immune response against the antigen in the Seldeg is desirable (for example, in tumor imaging). In such applications, Seldegs that are configured to bind to Fc gamma receptors and complement may be preferred. For example, Seldegs that include Fc fragments lacking engineered mutations to have decreased binding affinity or no binding affinity for Fc gamma receptors and/or complement (C1q) described herein, such as arginine mutations, may be configured to elicit such an immune response. Seldegs that include Fc fragments with mutations known to those with skill in the art to increase binding 20 to Fc gamma receptors and or complement (C1q) may also be configured to elicit such an immune response. Such Seldegs may also be configured to comprise more than one antigen molecule of the same type per Seldeg (FIG. 2K. 2L, 2M, or 2N) to enhance immune complex formation.

For example, Seldegs can have variations in numbers of targeting domains or antibody fragments (e.g. Fab fragments or scFv fragments) that range from 1-3 targeting domains or antibody fragments (FIG. 2). These targeting domains or antibody fragments can be linked to immunoglobulin Fc fragments, whereas in others, the targeting domains or antibody fragments may be linked to each other; the antigen and antibody fragments can be fused to Fc fragments or each other in different orientations (FIG. 2); Seldegs can include linker sequences that vary in length and composition between the fusion proteins, domains or fragments can be used e.g. IEGRMD (SEQ ID NO:37), GGGGS (SEQ ID NO:38) or 2-3 repeats of this linker; antigen mimetics such as small molecules or peptides can be used; the Fc fragment in Seldegs may be mutated so that it has substantially reduced binding affinity for Fc gamma receptors, complement, and increased affinity for binding to FcRn; The Fc fragments of a Seldeg may have mutations such as knobs-into-holes and/or electrostatic steering mutations so that heterodimers of antigen-linked and non-antigen-linked Fc fragments or containing two different antigens are formed.

Seldegs can include the following antigens that include proteins, glycoproteins and nucleic acids associated with autoimmune disease, including autoimmune encephalitides: myelin oligodendrocyte glycoprotein (MOG), myelin basic protein, proteolipid protein, myelin-associated glycoprotein, myelin-associated oligodendrocyte basic protein, transaldolase, acetylcholine receptor, muscle specific kinase, low density lipoprotein receptor related protein 4, insulin, islet antigen 2, glutamic acid decarboxylase 65, zinc transporter 8, citrullinated antigens, carbamylated antigens, collagen, cartilage gp39, gp130-RAPS, 65 kDa heat shock protein, fibrillarin, small nuclear protein (snoRNP), aquaporin 4, thyroid stimulating factor receptor, nuclear antigens, DNA, histones, glycoprotein gp70, ribosomes, pyruvate dehydrogenase dehydrolioamide acetyltransferase, hair follicle antigens, human tropomyosin isoform 5, N-Methyl-D-aspartate (NMDA) receptor, α-amino-3-hydroxy-5-methyl-4-isoxazolepropionic acid (AMPA) receptor, $GABA_A$ and $GABA_B$ receptors, glycine receptor, dipeptidyl-peptidase-like protein 6 (DPPX), glutamate receptor (GluR5), voltage gated potassium channel, Hu, Thyroid peroxidase, thyroglobulin, thyroid stimulating hormone (TSH) receptor, thyroid hormones T3 and T4, desmoglein 1 and 3, among others identifiable by skilled persons. The following antigens are examples of antigens that are associated with tumors and can be incorporated into Seldegs to clear tumor-specific antibodies during diagnostic imaging: HER2, prostate specific membrane antigen (PSMA), prostate stem cell associated antigen (PSCA), c-Met, EpCAM, carcinoembryonic antigen (CEA). Other antigens include therapeutics for which patients have specific antibodies, or transplantation antigens that are recognized by antibodies in transplant recipients. In addition, it is possible to generate molecular mimics (synthetic, protein fragments etc.) of antigens, and these can also be used to generate Seldegs. The above antigens are examples and are not limiting to additional types of possible antigens identifiable by persons skilled in the art upon reading of the present disclosure.

In several examples described herein, the Seldeg can be a heterodimer of fusion proteins comprising the amino acid sequences of SEQ ID NO: 2 plus SEQ ID NO: 6, SEQ ID NO: 4 plus SEQ ID NO: 6, SEQ ID NO: 8 plus SEQ ID NO: 10, SEQ ID NO:12 plus SEQ ID NO: 14, SEQ ID NO:16 plus SEQ ID NO: 18 plus the antibody light chain SEQ ID NO: 20, SEQ ID NO: 22 plus SEQ ID NO: 24 plus the antibody light chain SEQ ID NO: 20, SEQ ID NO: 26 plus SEQ ID NO: 28, SEQ ID NO: 30 plus SEQ ID NO: 6, SEQ ID NO: 32 plus SEQ ID NO: 6, or SEQ ID NO: 34 plus SEQ ID NO: 6, or homologs thereof.

The Seldeg can be a fusion protein comprising an amino acid sequence having at least 50% identity with SEQ ID NO: 2, SEQ ID NO: 4, SEQ ID NO: 6, SEQ ID NO:8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34.

As used herein, "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that similarity between sequences is typically measured by a process that includes the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may include additions or deletions (gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can be, for example, a sequence identifiable in a database such as GenBank and UniProt and others identifiable to those skilled in the art.

As understood by those skilled in the art, determination of percent identity between any two sequences can be accomplished using a mathematical algorithm. Computer implementations of suitable mathematical algorithms can be utilized for comparison of sequences to determine sequence identity. Such implementations include, but are not limited to: CLUSTAL, ALIGN, GAP, BESTFIT, BLAST, FASTA, among others identifiable by skilled persons.

For example, Seldegs according to the present disclosure can have an amino acid sequence having at least 50% sequence identity, preferably at least 80%, more preferably at least 90%, most preferably at least 95% sequence identity compared to SEQ ID NO: 2, SEQ ID NO: 4, SEQ ID NO:6, or SEQ ID NO:8, or SEQ ID NO:10, or SEQ ID NO:12, or SEQ ID NO:14, or SEQ ID NO:16, or SEQ ID NO:18, SEQ ID NO:20, SEQ ID NO: 22, SEQ ID NO: 24, SEQ ID NO: 26, SEQ ID NO: 28, SEQ ID NO: 30, SEQ ID NO: 32, or SEQ ID NO: 34.

The antigen-specific antibodies that are targeted by Seldegs can be autoantibodies that are present in a patient, antibodies that bind to therapeutics, antibodies that recognize transplant and modified (e.g. radiolabeled) antibodies or fragments/engineered forms that are used in diagnostic imaging, among others identifiable by persons skilled in the art.

As shown in the examples below, Seldegs are able to selectively deplete target antigen-specific antibodies with specificity for their fused antigen, for example, the target antigen-specific antibodies HER2-specific trastuzumab or pertuzumab ("TZB" or "PZB") and MOG-specific antibody ("8-18C5"). As shown in the examples below, Seldegs are able to selectively deplete the target antigen-specific antibodies without negatively affecting the total IgG levels or eliciting an adverse immune reaction. These findings stand in contrast to other approaches, in which treatment results in depletion of total IgGs, through the use of FcRn inhibitors or antibodies that destroy B-cells. Such approaches adversely affect antibodies of non-targeted specificities or B-cell function because they lack the selectivity provided by Seldegs.

Based on this unique selectivity, the Seldeg platform has many applications because Seldegs may be created with many other targeting proteins and antigens. Examples of such applications include treatment of autoimmune disorders, treatment of antibody-mediated rejection prior to or during transplantation, increasing contrast during whole body imaging of tumors (e.g., the tumor antigens PSMA, EpCAM, and CEA may be used as antigens for developing additional Seldegs), depleting the bodily concentration of a particular biologic after administration, for instance, if an adverse reaction is observed, removal of antibodies to clear antibodies that recognize a therapeutic prior to delivery of the therapeutic.

Seldegs may be administered in any way able to deliver them to cells expressing the receptor or other molecule on the cell surface that is being targeted, such as via injection, particularly intravenous, subcutaneous or intramuscular injection, or injection into a tissue targeted by the antigen-specific antibody that is to be depleted. Seldegs can also be expressed in cells that have been genetically engineered to contain expression constructs encoding Seldegs. In particular, cells can be genetically engineered by introducing expression constructs that encode Seldeg proteins that include proteins or peptides that allow secretion of Seldegs from the engineered cells in situ. For example, patient derived cells could be transfected with expression constructs encoding Seldegs and the transfected cells delivered back into the patient, using similar approaches to those described for chimeric antigen receptor (CAR) T cell therapy. The expression constructs would comprise an expression vector known to those skilled in the art and may, for example, contain genes encoding MOG Seldeg (SEQ ID NO: 1 and 5), with secretion leader peptides such as those derived from immunoglobulin genes linked to the 5' end of the coding sequence for the mature MOG Seldeg (SEQ ID NO: 1) and Fc (SEQ ID NO: 5).

Seldegs may be administered in an amount that does not block every targeted receptor/cell surface molecule, allowing normal function of the cell surface receptor/molecule. The dose of Seldeg used may be similar to the amount of antibody being targeted for clearance, which will depend, for example, on the specifics of the antibody-mediated disease, or whether Seldegs are being used to improve contrast in diagnostic imaging. The amount of Seldeg used is expected to be less than the total number of receptor types being targeted, so that the normal function of the targeted receptor is not adversely affected. In addition, Seldegs can be designed so that they do not compete with the natural ligand of the cell surface receptor or cell surface molecule for binding, for example, by using nanobodies (VHH) that bind to FcRn at a site that does not overlap with the IgG binding site (for example as described in Andersen, J. T., Gonzalez-Pajuelo, M., Foss, S., Landsverk, O. J. B., Pinto, D., Szyroki, A., de Haard, H. J., Saunders, M., Vanlandshoot, P., Sandlie, I. (2012) Selection of nanobodies that target human neonatal receptor. Sci. Rep., 3, 1118). In addition, Seldegs may remove less than 10%, less than 5%, less than 1%, or less than 0.1% of non-targeted antibodies in the circulation or in a tissue targeted by the antigen-specific antibody that is to be depleted. Retention of non-targeted antibodies during and after Seldeg treatment may be important in normal immune function and the avoidance of infections, among other effects as described herein.

Seldegs may be administered daily, weekly, or whenever 50% of patients are expected to have regenerated a threshold amount of targeted antigen-specific antibody in the circulation or in a tissue recognized by the targeted antigen-specific antibody. The levels of targeted antigen-specific antibody can be determined by using enzyme-linked immunosorbent assays (ELISAs) to analyze serum samples. Alternatively, other methods that are well known to those with skill in the art can be used.

In transplant patients at risk for antibody-mediated rejection, the Seldegs may be administered before or after transplantation. An emergency dose of Seldegs may be administered if the target antigen-specific antibody reaches a threshold amount of target antigen-specific antibody in the circulation or in a tissue recognized by the target antigen-specific antibody. The levels of targeted antigen-specific antibody can be determined by using enzyme-linked immunosorbent assays (ELISAs) to analyze serum samples. Alternatively, other methods that are well known to those with skill in the art can be used.

In patients that have antibodies specific for a therapeutic, such as a protein-based therapeutic, the Seldegs may be administered before the delivery of the therapeutic to deplete such antibodies. This is expected to overcome problems associated with rapid antibody-mediated clearance of therapeutics if they have elicited an immune response during prior delivery, or if preexisting antibodies specific for the therapeutic are present in the patient. Preexisting or induced antibodies specific for the protein-based therapeutic can be detected using a number of different methods (for example such as those described in Xue, L., Clements-Egan, A., Amaravadi, L., Birchler, M., Gorovits, B., Liang, M., Myler, H., Purushothama, S., Manning, M. S., Sung, C. (2017) Recommendations for the assessment and management of preexisting drug-reactive antibodies during biotherapeutic development. AAPS, 19, 1576-1586).

In diagnostic/theranostic imaging, it is expected that delivery of the radiolabeled imaging antibody will be followed by a period to allow tumor localization. Subsequently, Seldegs can be used to clear radiolabeled antibody from off-target sites (e.g. circulation) to result in improved contrast. For example, this approach can include the following steps: first, a patient is injected with radiolabeled (or other label) antibody that binds to a tumor antigen. Second, following a period (e.g. 16-24 hours) to allow the radiolabeled antibody to bind to the tumor, the Seldeg is injected in an amount that is equivalent in molar amounts to the injected dose of imaging agent. Following a clearance period (e.g. 8-24 hours), the patient is imaged using positron emission tomography or other whole body imaging modality.

The Seldeg may be administered in an amount sufficient to deplete at least 50%, at least 80% or at least 90% of the concentration of the target antigen-specific antibody in the circulation or in a tissue recognized by the target antigen-specific antibody within one hour, two hours, five hours, 24 hours or 48 hours or longer of administration. The persistence of the Seldeg in the body will be a determinant of how long it has activity in depleting antigen-specific antibody. Seldegs can be designed to have different in vivo half-lives by the behavior of the cell surface receptor or cell surface molecule that they target. The affinity of the Seldeg for this cell surface receptor or cell surface molecule can also be modified using mutagenesis and approaches known to those with skill in the art, to result in Seldegs that have different persistence in the circulation and/or tissues. In particular, the Seldeg may be administered in an amount at least approximately equimolar with the amount of antigen-specific antibody to be depleted. The Seldeg can be administered in an amount that is, for example, in an approximately 1:1, 2:1, 3:1, 4:1, 5:1, 6:1, 7:1, 8:1, 9:1, 10:1 or higher molar ratio to the target antigen specific antibody. In particular, for example, wherein a Seldeg targets an antibody that is administered to a patient (e.g. anti MOG, or anti HER2 antibodies, and the like) a Seldeg can be administered in a dose that is for example, in an approximately 1:1, 2:1, 3:1, 4:1, 5:1, 6:1, 7:1, 8:1, 9:1, 10:1 or higher molar ration to the target antigen specific antibody.

EXAMPLES

The following examples are provided to further illustrate specific embodiments of the disclosure. They are not intended to disclose or describe each and every aspect of the disclosure in complete detail and should be not be so interpreted. Unless otherwise specified, designations of cells lines and compositions are used consistently throughout these examples.

Example 1—Expression and Purification of Seldegs that Bind to FcRn

Figure 3A:
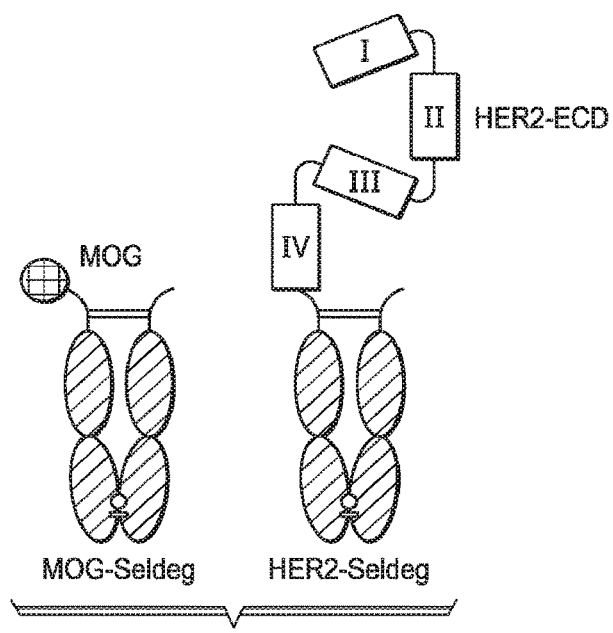
FIG. 3A is a schematic diagram of two exemplary FcRn-targeting Seldegs, a human epidermal growth factor receptor 2 Seldeg ("HER2-Seldeg") and a myelin oligodendrocyte glycoprotein Seldeg ("MOG-Seldeg")

Seldegs that target FcRn on cells contain a recombinant antigen as a monomer linked to a dimeric, human IgG1-derived Fc fragment (FIG. 3A) with mutations to eliminate interactions with human FcγRs and to enhance the binding affinity of the Seldeg Fc fragment to FcRn at near-neutral pH. Heterodimer formation of these two Seldegs is achieved by inserting 'knobs-into-holes' mutations in the CH3 domains.

Expression constructs to generate the exemplary HER2-Seldeg (SEQ ID NOS: 3, 4, 5 and 6) were made as follows: to express the polypeptide chain with HER2 fused to an engineered Fc fragment (SEQ ID NO: 3), the gene encoding the HER2 leader peptide and extracellular domain (ECD consisting of 630 residues) was isolated from a HER2-overexpressing breast cancer cell line (BT-474) employing standard molecular biology techniques. This gene was fused via a IEGRMD linker peptide to the N-terminus of the hinge region of a gene encoding the human IgG1-derived Fc fragment using splicing by overlap extension. Mutations to ablate binding to FcγRs ($G_{236}R/L328R$; EU numbering), enhance binding to FcRn (MST-HN; M252Y/S254T/T256E/H433K/N434F; EU numbering) and generate 'knobs-into-holes' (Y349T/T394F; EU numbering) were inserted into the Fc fragment gene using standard methods. Cysteine (C220; EU numbering) in the hinge region that bridges with cysteine in the light chain constant region was also mutated to serine. Fc fragment genes with FcRn-enhancing mutations, mutations to ablate FcγR binding and without fused antigen were generated with complementary knobs-into-holes mutations (S364H/F405A; EU numbering) (SEQ ID NO: 5). Recombinant proteins were expressed in HEK-293F (Life Technologies) cells following transient transfection with the Gibco Expi293™ expression system kit (Life Technologies). The HER2-Seldeg was purified from culture supernatants using an anion exchange column (SOURCE-15Q, GE Healthcare) at pH 8.0 and a linear salt gradient (0-0.5 M NaCl). Alternatively, HER2-Seldeg can be purified using protein A-Sepharose and standard methods. Following elution from the column (ion exchange or protein A-Sepharose) HER2-Seldeg was dialyzed against phosphate buffered saline (PBS). HER2-Seldeg was further purified using size exclusion chromatography (SEC) (GE Healthcare) in PBS (Lonza) prior to use in experiments. Expression plasmids for other Seldegs were made using analogous methods, and recombinant proteins expressed in transfected HEK-293F cells. Seldegs without FcRn-enhancing mutations (e.g. MOG-Seldeg-PS; MOG-Seldeg-TfRSEQ ID NOS: 7, 8, 9, 10, 11, 12, 13 and 14, 15, 16, 17, 18, 19, and 20) were purified using protein G-Sepharose.

Seldegs targeting antibodies specific for two antigens were generated: (1) the HER2-Seldeg; and (2) the MOG-Seldeg. The antigen HER2 is a well-defined target for therapy and also for diagnostic imaging of HER2-overexpressing tumors with HER2-specific antibodies, such as tastuzumab (TZB) or pertuzumab (PZB). The antigen MOG is recognized by autoreactive antibodies in both animal models of multiple sclerosis (MS) and MS in humans.

Figure 3B:
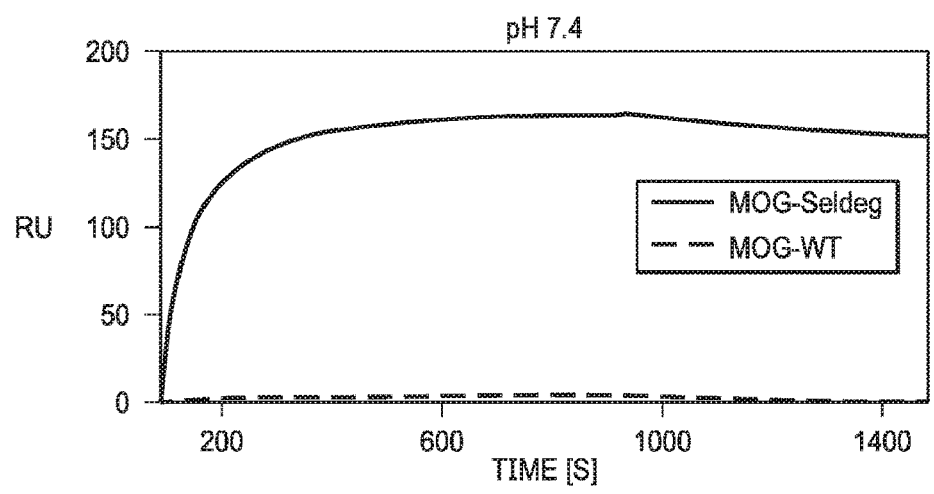
FIG. 3B shows the increased binding of an exemplary FcRn-targeting Seldeg to FcRn at pH 6.0 and 7.4.
Figure 3B:
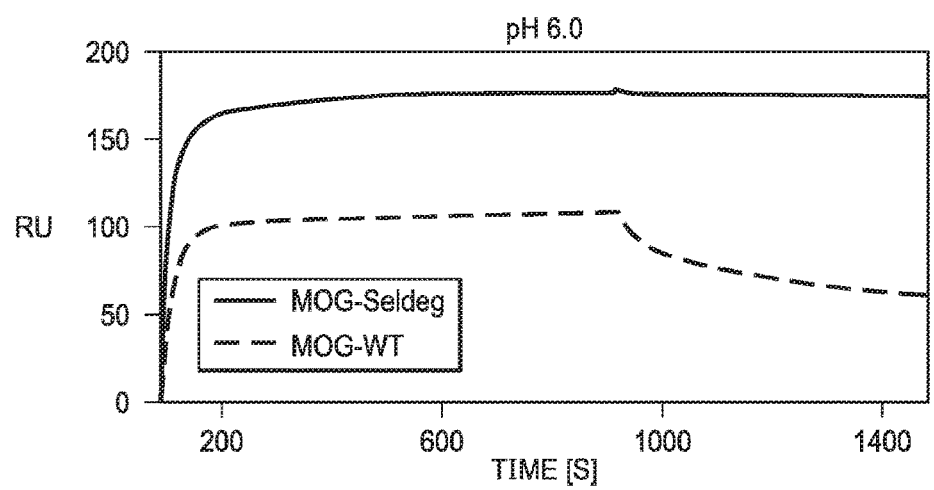

The HER2-Seldeg and MOG-Seldeg maintain a significantly higher binding affinity for FcRn at neutral pH and at an acidic pH, in contrast to recombinant fusion proteins comprising HER2 or MOG fused to Fc fragments to generate analogous constructs ("HER2-WT" and "MOG-WT", respectively) to the HER2-Seldeg and MOG-Seldeg, except they lack the FcRn-enhancing MST-HN mutations (M252Y, S254T, T256E, H433K, N434F; EU numbering) that increase binding affinity at near-neutral pH (FIG. 3B). Surface plasmon resonance experiments to analyze the interactions of the recombinant proteins with FcRn were carried out using a BIAcore T200 (GE Healthcare). Binding of Seldeg/WT to recombinant mouse FcRn was analyzed by injecting 100 nM MOG/HER2-Seldeg or MOG/HER2-WT over immobilized FcRn (coupled at ~600 RU on a CM5 sensor chip) in PBS (pH 6.0 or 7.4) plus 0.01% v/v Tween-20 at a flow rate of 10 μl/minute. Flow cells were regenerated following each injection and dissociation phase using 0.15 M NaCl, 0.1 M sodium bicarbonate, pH 8.5. Data were zero-adjusted and background-subtracted (background obtained by injection over a flow cell coupled with buffer only during coupling reaction).

Mutations to increase FcRn such as MST-HN were identified using the following approach: residues in proximity to amino acids (e.g. 253, 435) that are known to be essential for FcRn binding were randomly mutated in an Fc fragment gene and the libraries of mutated Fc fragments displayed on phage. Fc fragments with increased binding affinity for FcRn were selected using phage display technology (Ghetie, V., Popov, S., Borvak, J., Radu, C., Matesoi, D., Medesan, C., Ober, R. J., Ward, E. S. (1997) Increasing the serum persistence of an IgG fragment by random mutagenesis, Nature Biotech., 15, 637-640; Dall'Acqua, W. F., Woods, R. M., Ward, E. S., Palaszynski, S. R., Patel, N. K., Brrewah, Y. A., Wu, H., Kiener, P. A., Langermann, S. (2001) Increasing the affinity of a human IgG1 for the neonatal receptor: biological consequences, J. Immunol., 169, 5171-5180). Alternatively, these residues can be mutated to every other possible amino acid and Fc fragments with higher affinity for FcRn identified using methods such as ELISA or surface plasmon resonance binding analyses.

Figure 3C:
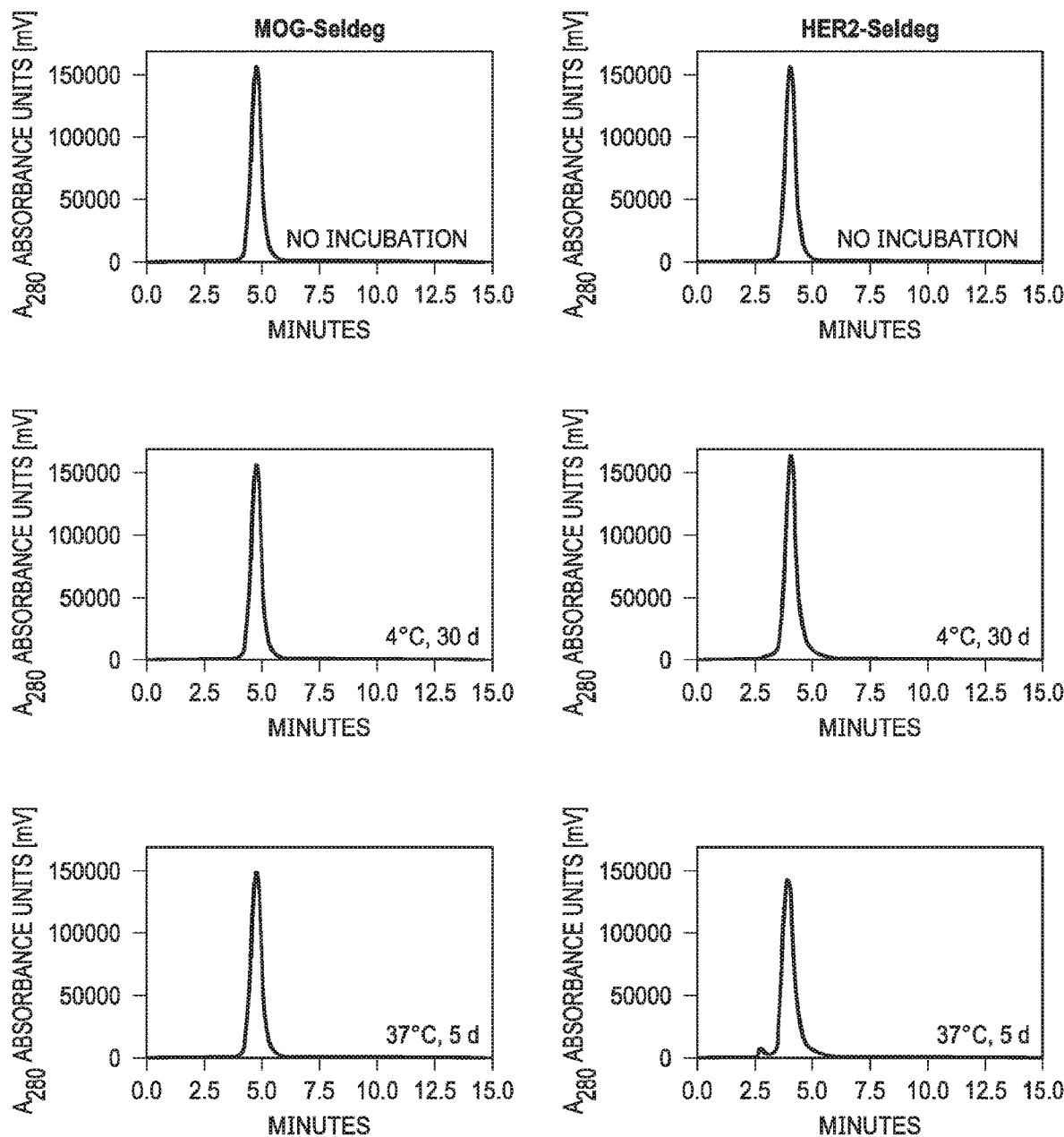
FIG. 3C shows HPLC analyses of two exemplary FcRn-targeting Seldegs following incubation at 4° C. (30 days) and 37° C. (5 days) to evaluate their storage stability.

Size exclusion analyses indicate that the recombinant proteins comprising the Seldegs do not form aggregates following incubation in phosphate buffered saline when incubated for up to 30 days at 4° C. or 5 days at 37° C. (FIG. 3C).

Example 2—Ability of Seldegs that Target FcRn to Deplete Target Antigen-Specific Antibodies in Mice that Transgenically Express Human FcγRs (huFcγR Mice)

To determine the ability of Seldegs to deplete target antigen-specific antibodies, mice that transgenically express human FcγRs (huFcγR mice; Smith, P., DiLillo, D. J., Bournazos, S., Li, F., Ravetch, J. V. (2012). Mouse model recapitulating human Fc receptor structural and functional diversity. Proc. Natl. Acad. Sci. USA 109, 6181-6186) were injected with 15 μg of radiolabeled ($^{125}$I-labeled) MOG-specific antibody 8-18C5. 24-hours after the huFcγR mice were injected with 8-18C5, 125 μg or 31 μg of MOG-Seldeg or a control was administered via injection. In FIG. 3D, "MOG-Seldeg-High" corresponds to the 125 μg dose and "MOG-Seldeg-Low" corresponds to the 31 μg dose. The controls are phosphate-buffered saline ("PBS") and unmodified MOG-Fc fusion protein ("MOG-WT"). MOG-WT is an analogous construct to the MOG-Seldeg, except it lacks the FcRn-enhancing MST-HN mutations that increase binding affinity at near-neutral pH.

To generate the data of FIG. 3D whole body counts of radiolabeled 8-18C5 were taken at the indicated times. Counts per minute ("CPM") obtained 24 hours after 8-18C5 administration, immediately prior to Seldeg or control delivery, are taken as 100% for each mouse and CPM of whole body obtained thereafter are normalized to this time point. The error bars indicate standard deviations and statistically significant differences were determined using two-way ANOVA with Tukey's multiple comparisons, with $p<0.05$ and n=6 mice/group.

Doses of 125 μg and 31 μg of MOG-Seldeg are approximately 2 to 8-fold lower (on a molar basis) than a dose of 500 μg, a MST-HN Abdeg, which has been shown to globally eliminate IgG levels in mice. Such lower doses of MOG-Seldeg were used to minimize effects on IgGs that were not specific for the fused antigen through competition with the Seldeg for FcRn binding. The doses of 125 μg or 31 μg represent an approximate 16 and 4-fold molar excess, respectively, over the 8-18C5 target antigen-specific antibody.

FIG. 3D provides a graph of normalized body counts of radiolabeled 8-18C5 (the target antigen-specific antibody) versus time. Administration of MOG-Seldeg resulted in a rapid, dose-dependent decrease in 8-18C5 in normalized whole body counts (FIG. 3D), which demonstrates the ability of MOG-Seldeg to selectively deplete 8-18C5 from the body. In contrast, the injection of control MOG-WT, lacking the FcRn-enhancing MST-HN mutations, had no effect on 8-18C5 antibody depletion. This demonstrates the importance of the MST-HN mutations to confer a high binding affinity for FcRn at pH 6.0-7.4.

Example 3—Specificity of Seldegs that Target FcRn and their Ability to Induce a Significant Decrease in Target Antigen-Specific Antibodies Levels, Both in Blood and Throughout the Body To analyze the specificity of Seldegs and their effect on antibodies with different antigen recognition properties, the behavior of the HER2-specific antibody trastuzumab (TZB) was investigated in the presence of both HER2-Seldeg and MOG-Seldeg (FIG. 3E). To generate the data of FIG. 3E, huFcγR mice were intravenously injected with 15 μg of radiolabeled ($^{125}$I-labeled) TZB and subsequently with a 4-fold molar excess of HER2-Seldeg, or, as a control for antigen specificity, MOG-Seldeg. Additional controls are phosphate-buffered saline ("PBS"), Abdeg and a recombinant fusion protein comprising HER2 fused to an Fc fragment to generate an analogous construct ("HER2-WT") to the HER2-Seldeg, except it lacks the FcRn-enhancing MST-HN mutations that increase binding affinity at near-neutral pH. In contrast to a Seldeg, an "Abdeg" is a human IgG1-derived antibody with the MST-HN mutations that non-selectively depletes antibodies. Such proteins are called Abdegs because they are antibodies that generally cause IgG degradation.

To generate the data of FIG. 3E, the mice were bled and blood and whole body counts were taken at the indicated times. Counts per minute ("CPM") obtained 24-hours after TZB administration, immediately prior to Seldeg or control delivery, are taken as 100% for each mouse and CPM of blood and whole body obtained thereafter are normalized to this time point. The error bars indicate standard deviations and statistically significant differences were determined using two-way ANOVA with Tukey's multiple comparisons, with $p<0.05$ and n=6 mice/group.

FIG. 3E provides graphs of normalized blood and body counts of radiolabeled TZB (the target antigen-specific antibody) versus time. Administration of HER2-Seldeg caused a significant decrease in normalized body counts of TZB, both in blood and whole body counts, which demonstrates the ability of HER2-Seldeg to selectively deplete TZB from the body. In contrast, the control proteins demonstrated similar behavior to that observed for the PBS control (FIG. 3E).

Example 4—Ability of Seldegs that Target FcRn to Rapidly Deplete Target Antigen-Specific Antibodies Mice were intravenously administered with radiolabeled ($^{125}$I) TZB (15 μg) and 24 hours later HER2-Seldeg (51 μg; four-fold molar excess over TZB) was delivered intravenously. Additional controls are phosphate-buffered saline ("PBS") and Abdeg (60 μg).
To generate the data of FIG. 3F, the mice were bled and blood and whole body counts were taken at the indicated times. Counts per minute ("CPM") obtained 24-hours after TZB administration, immediately prior to Seldeg or control delivery, are taken as 100% for each mouse and CPM of blood and whole body obtained thereafter are normalized to this time point. The error bars indicate standard deviations and statistically significant differences were determined using two-way ANOVA with Tukey's multiple comparisons, with p<0.05 and n=5-6 mice/group.

Figure 3F:
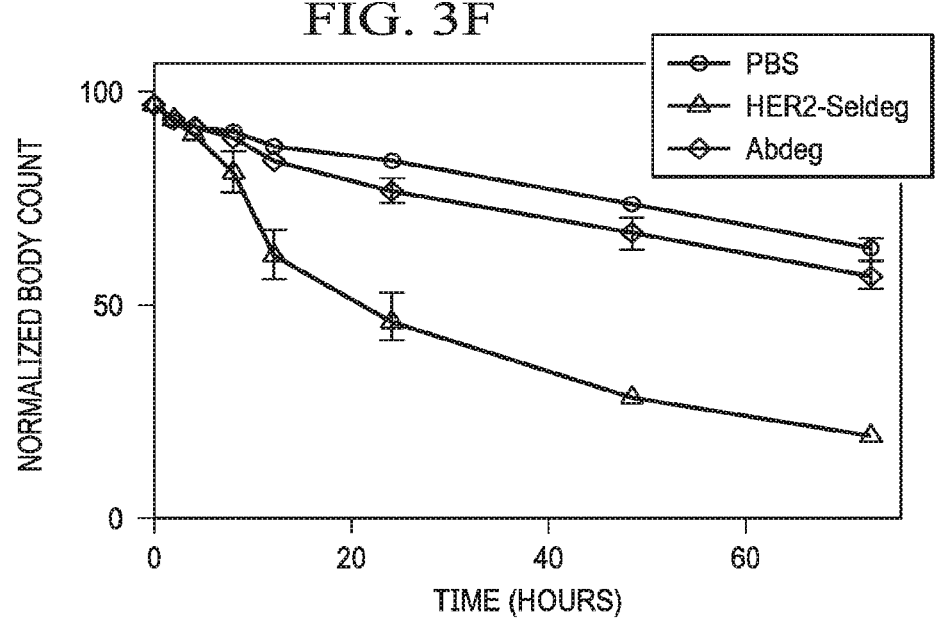
FIG. 3F shows additional graphs reporting exemplary normalized blood and body count versus time, showing clearance of an antigen-specific antibody by an exemplary FcRn-targeting Seldeg.
Figure 3F:
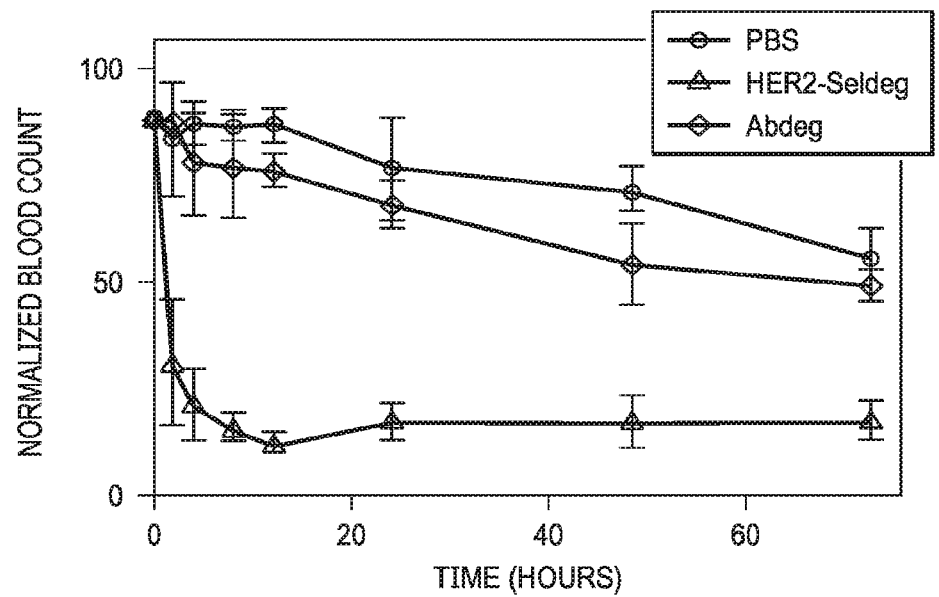

FIG. 3F provides graphs of normalized blood and body counts of radiolabeled TZB (the target antigen-specific antibody) versus time. Administration of HER2-Seldeg caused a rapid decrease in normalized body and blood counts of TZB, which demonstrates the ability of the HER2-Seldeg to rapidly deplete TZB from the body. Notably, the blood counts of TZB were reduced close to background levels within two hours of Seldeg administration (FIG. 3F), further supporting the ability of the HER2-Seldeg to deplete target antigen-specific antibodies rapidly from the blood. In contrast, at a dose of 60 µg/mouse, delivery of Abdeg resulted in similar behavior to that observed for the PBS control (FIG. 3F).

Example 5—Activity of Seldegs that Target Exposed Phosphatidylserine (PS) on the Cell Surface We also investigated the ability of a Seldeg in which the targeting protein is the C2 domain of synaptotagmin 1 (Syt1) to selectively deplete antibodies specific for MOG in huFcγR mice. Syt1 binds to exposed PS on cells, and the Seldeg is therefore designed MOG-Seldeg-PS and is shown schematically (FIG. 4A). MOG-Seldeg-PS(DN) that does not bind to PS due to the presence of the 'DN' mutations (D173N, D179N, D231N, D233N and D239N) was also generated. MOG Seldeg PS and MOG Seldeg PS(DN) were purified from culture supernatants of transfected HEK 293F cells using protein G-Sepharose and standard methods. Heterodimer formation was achieved by inserting knobs-into-holes and electrostatic steering mutations into the Fc regions, and size exclusion analyses indicate that the recombinant proteins are well behaved (FIG. 4A).

To generate the data shown in FIG. 4B, mice were intravenously injected with radiolabeled ($^{125}$I) chimeric 8-18C5 (human constant/mouse variable domains; MOG-specific; 15-20 µg) and 24 hours later phosphate-buffered saline (PBS), 40 µg MOG-Seldeg-PS or as controls, 34 µg Fc-Syt1 (no MOG attached) or 40 µg MOG-Seldeg-PS(DN) were delivered intravenously. Radioactivity levels were determined at the indicated times. Whole body CPM or blood CPM levels obtained immediately prior to MOG-Seldeg-PS or control delivery were taken as 100% and all subsequent CPM that were obtained were normalized against these CPM levels. Error bars indicate the standard error of the mean (SEM) and statistically significant differences between MOG-Seldeg-PS treated group and control groups (Fc-Syt1, MOG-Seldeg-PS(DN) and PBS) are indicated by * (p<0.05, two-way ANOVA with Tukey's multiple comparisons; n=5-6 mice/group).

Administration of MOG-Seldeg-PS caused a significant decrease in normalized body counts of 8-18C5, both in blood and whole body counts, which demonstrates the ability of MOG-Seldeg-PS to selectively deplete 8-18C5 from the body. In contrast, the control protein Fc-Syt1 demonstrated similar behavior to that observed for the PBS control, and although MOG-Seldeg-PS(DN) induced a decrease in 8-18C5 (due to residual binding to PS), the effect was much lower than that of MOG-Seldeg-PS (FIG. 4B).

Example 6—Ability of Seldegs that Target FcRn to Efficiently Internalize Target Antigen-Specific Antibodies into Endosomes and Cause Degradation Via Delivery to Lysosomes To determine the mechanism of activity of Seldegs at the cellular level, flow cytometry and fluorescence microscopy were performed to analyze the effects of Seldegs on the internalization and accumulation of target antigen-specific antibodies TZB and 8-18C5. First, human endothelial cells (HMEC-1) were transfected with a human FcRn-GFP expression construct, which was mutated so that its binding properties are analogous to mouse FcRn.

The Seldegs efficiently internalized bound target antigen-specific antibodies into endosomes within cells, and following 8 hours of incubation, the target antigen-specific antibodies were delivered to lysosomes.

FIG. 5A is a graph of mean fluorescence intensity ("MFI") and FIG. 5B and FIG. 5C are microscopic images of Seldeg activity in the presence of target antigen-specific antibodies, with microscopic images of representative endosomes cropped, expanded, and presented in the top right-corner insets. FIG. 5A shows a greater MFI in the presence of, respectively, Alexa 647-labeled TZB with HER2-Seldeg and Alexa 647-labeled 8-18C5 with MOG-Seldeg. This greater MFI indicates that co-incubation of HER2- and MOG-Seldeg, respectively, with TZB and 8-18C5 (400 nM Seldeg or WT control plus 100 nM antigen-specific antibody; 30 minute pulse, no chase or 60 minute chase, labeled 30' P or 30' P 60' C respectively, in FIGS. 5A, 5B, and 5C) results in high levels of TZB and 8-18C5 entering cells. Similar results were obtained when the HER2-specific antibody pertuzumab (PZB) was used instead of TZB in the presence of HER2-Seldeg (FIG. 5A). Further, the majority of each target antigen-specific antibody is retained by the cells during a 60 minute chase. In contrast, the accumulation of target antigen-specific antibodies within cells is substantially lower in the presence of negative controls HER2-WT (selective for TZB or PZB) and MOG-WT (selective for 8-18C5).

FIGS. 5B and C show that antigen-specific antibodies accumulate in cells and are associated with FcRn in endosomes in the presence of Seldegs. To generate the microscopic images of FIG. 5B, HMEC-1 cells were pulsed with 100 nM Alexa 647-labeled TZB (HER2-specific) in complex with 400 nM Alexa 555-labeled HER2-Seldeg or HER2-WT (as indicated) for 30 minutes, washed and either immediately fixed, or washed, chased in medium for 60 minutes, followed by fixation. Fixed cells were imaged using fluorescence microscopy. The data in FIG. 5C was generated using the same approach, except that 100 nM Alexa 647-labeled 8-18C5 (MOG-specific) in complex with 400 nM Alexa 555-labeled MOG-Seldeg or MOG-WT was used. Bars in each of the microscopic images are 5 μm, and bars in each of the microscopic image insets are 0.25 μm. The data shown in FIGS. 5B and 5C demonstrates that antigen-specific antibodies accumulate to substantially higher levels in FcRn-expressing cells in the presence of Seldegs that bind to FcRn compared with in the presence of control (WT) proteins.

FIG. 6A shows microscopic images of Seldeg activity in the presence of target antigen-specific antibodies, with microscopic images of representative lysosomes cropped, expanded, and presented in the top right-corner insets. For FIG. 6A, HMEC-1 cells were pre-pulsed with Alexa 555-labeled Dextran for 2 hours and washed, and then pulsed with 100 nM Alexa 647-labeled 8-18C5 (MOG-specific) in complex with 400 nM MOG-Seldeg or MOG-WT (as indicated) for 30 minutes, followed by an 8 hour chase and then washed, fixed and imaged. To generate the microscopic images of FIG. 6B, HMEC-1 cells were pre-pulsed with Alexa 555-labeled Dextran for 2 hours and washed, and then pulsed with either 100 nM Alexa 647-labeled TZB or 8-18C5 antibodies, and 400 nM MOG-Seldeg or HER2-Seldeg (as indicated) for 30 minutes followed by an 8 hour chase, and then washed, fixed and imaged. For each overlay image (shown in the right column), GFP, Alexa 555 and Alexa 647 are pseudo-colored green, red and blue, respectively. Bars in each of the microscopic images are 5 µm, and bars in each of the microscopic image insets are 0.25 µm. Notably, FIG. 6B shows that the cells do not accumulate TZB and 8-18C5 in lysosomes in the presence of MOG-Seldeg or HER2-Seldeg, respectively, which indicates the antigen specificity of their effects.

Example 7—Ability of Seldegs that Target Phosphatidylserine to Efficiently Internalize Target Antigen-Specific Antibodies into Endosomes and Cause Degradation Via Delivery to Lysosomes FIG. 7 shows that MOG-Seldeg-PS efficiently internalizes MOG-specific antibodies (chimeric 8-18C5) into endothelial cells and macrophages and uptake is dependent on PS-binding. Endothelial cells (2H11) or macrophages (RAW264.7) that expose PS were incubated with 10 nM Alexa 647-labeled chimeric 8-18C5 mixed with 20 nM MOG-Seldeg-PS, MOG-Seldeg-PS(DN) or Fc-Syt1 (no MOG) for 2 hours. Mean fluorescence intensities (MFI) of Alexa 647-labeled chimeric 8-18C5 (made by fusing the variable domains of the mouse antibody, 8-18C5, to the constant regions of human IgG1, Cκ, using methods well known to those skilled in the art) for triplicate samples were determined by flow cytometry.

This exemplary PS-binding Seldeg is calcium-dependent and therefore dissociates in endosomes where the calcium concentration is much lower. Not all PS-targeting Seldegs are expected to be calcium-dependent, but some, also such as those comprising annexin V will have this property, as would be understood by skilled persons. In addition, several antibodies can bind to beta-2 glycoprotein 1 that can in turn bind to PS.

Example 8—Ability of Seldegs that Target the Transferrin Receptor to Efficiently Internalize Target Antigen-Specific Antibodies into Cells Expressing the Human Transferrin Receptor A Seldeg comprising antigen (MOG) fused to an antibody that targets the transferrin receptor (MOG-Seldeg-TfR) has been generated and is shown schematically in FIG. 8. MOG-Seldeg-TfR and control antibody, Ab-TfR (no MOG present), were purified from culture supernatants of transfected HEK-293F cells using protein G-Sepharaose and standard methods. Seldeg-TfR efficiently internalizes MOG-specific antibodies (chimeric 8-18C5) into endothelial (HMEC-1) cells and uptake is dependent on the presence of MOG in the Seldeg (FIG. 9). HMEC-1 cells that express human TfR were incubated with 50 nM Alexa 647-labeled chimeric 8-18C5 (specific for MOG) mixed with 200 nM MOG-Seldeg-TfR, or TfR-specific antibody (Ab-TfR; no MOG) for 30 minutes followed by washing and no chase (30'P), or for 30 minutes followed by washing and a 60 minute chase period (30'P, 60'C). Mean fluorescence intensities (MFI) of Alexa 647-labeled 8-18C5 for triplicate samples were determined by flow cytometry (FIG. 9).

Example 9—Ability to Seldegs that Target FcRn to Clear Background During Positron Emission Tomographic Analyses of Tumors Using Radiolabeled Antibodies Female BALB/c SCID mice were implanted in the mammary fat pad ($0.5\times10^6$ cells/mouse; cells were suspended in RPM1-1640/Matrigel prior to injection) with the HER2-positive breast cancer cell line, HCC1954. 6-7 days later, mice were injected with 124-I labeled TZB (60 μg/mouse) and analyzed using positron emission tomography (PET) 22 hours later. Mice were injected with a molar equivalent of HER2-Seldeg (51 μg/mouse) or, as controls, MOG-Seldeg (31 μg/mouse) or PBS vehicle (n=3 mice/group). Mice were analyzed using PET 4 hours following injection of the Seldegs or PBS. Imaging of mice was carried out using a Siemens Inveon PET-computed tomography (CT) Multimodality System.

To generate the date shown in FIG. 10A, mice were imaged at 22 hours following injection of 124-I labeled TZB (22 h) and at 4.5-5 hours post-injection ('4.5 h clearing') of HER2-Seldeg, MOG-Seldeg or PBS. PET and CT images were co-registered in the AMIDE software package. FIG. 10B provides graphs of contrast measures for radiolabel intensity for 22 hours post-injection of 124-I labeled TZB and 4 hours post-injection of HER2-Seldeg, MOG-Seldeg or PBS. To determine contrast measures, two regions of interest were identified in the thoracic region (background) and tumor. The mean values (n=3 mice/group) for the ratios of mean intensity in the tumor to mean intensity in the thoracic regions are plotted. Error bars indicate standard errors. Statistically significant differences ($p<0.05$) between mice treated with HER2-Seldeg vs. MOG-Seldeg or PBS are shown. The data show that delivery of HER2-Seldeg reduces the background in the thoracic region of the mice.

Example 10—DNA and Proteins Sequences of Exemplary Seldegs and Controls and Variants Thereof Having Mutations Such as Knobs-into-Holes Mutations, Arginine Mutations and Electrostatic Steering Mutations Table 1 shows DNA sequences of polynucleotides encoding exemplary proteins described herein, and Table 2 shows amino acid sequences of exemplary proteins encoded by the polynucleotides shown in Table 1, wherein the DNA sequence of SEQ ID NO: 1 encodes the protein of SEQ ID NO:2, the DNA sequence of SEQ ID NO: 3 encodes the protein of SEQ ID NO:4, the DNA sequence of SEQ ID NO: 5 encodes the protein of SEQ ID NO: 6, the DNA sequence of SEQ ID NO: 7 encodes the protein of SEQ ID NO: 8, the DNA sequence of SEQ ID NO: 9 encodes the protein of SEQ ID NO: 10, the DNA sequence of SEQ ID NO: 11 encodes the protein of SEQ ID NO: 12, the DNA sequence of SEQ ID NO: 13 encodes the protein of SEQ ID NO: 14, the DNA sequence of SEQ ID NO: 15 encodes the protein of SEQ ID NO: 16, the DNA sequence of SEQ ID NO: 17 encodes the protein of SEQ ID NO: 18, the DNA sequence of SEQ ID NO: 19 encodes the protein of SEQ ID NO: 20, the DNA sequence of SEQ ID NO: 21 encodes the protein of SEQ ID NO: 22, the DNA sequence of SEQ ID NO: 23 encodes the protein of SEQ TD NO: 24, the DNA sequence of SEQ ID NO: 25 encodes the protein of SEQ ID NO: 26, the DNA sequence of SEQ ID NO: 27 encodes the protein of SEQ ID NO: 28, the DNA sequence of SEQ ID NO: 29 encodes the protein of SEQ ID NO: 30, the DNA sequence of SEQ ID NO: 31 encodes the protein of SEQ ID NO: 32, the DNA sequence of SEQ ID NO: 33 encodes the protein of SEQ TD NO: 34.

TABLE 1

DNA sequences of polynucleotides encoding exemplary proteins.

| Polynucleotide encoding protein | DNA sequence | SEQ ID NO: |
|---|---|---|
| MOG-Seldeg with MST-HN, knobs-into-holes and arginine mutations | GGACAATTCAGAGTGATAGGACCAGGGTATCCCATCCGG GCTTTAGTTGGGGATGAAGCAGAGCTGCCGTGCCGCATC TCTCCTGGGAAAAATGCCACGGGCATGGAGGTGGGTTGG TACCGTTCTCCCTTCTCAAGAGTGGTTCACCTCTACCGAA ATGGCAAGGACCAAGATGCAGAGCAAGCACCTGAATACC GGGGACGCACAGAGCTTCTGAAAGAGACTATCAGTGAGG GAAAGGTTACCCTTAGGATTCAGAACGTGAGATTCTCAG ATGAAGGAGGCTACACCTGCTTCTTCAGAGACCACTCTTA CCAAGAAGAGGCAGCAATGGAGTTGAAAGTGGAAGATG GAGGCGGTGGATCAGTTGAGCCCAAATCTTCTGACAAAA CTCACACATGCCCACCGTGCCCAGCACCTGAACTCCTGA GGGGACCGTCAGTCTTCCTCTTCCCCCCAAAACCCAAGGA CACCCTCTACATCACTCGGGAACCTGAGGTCACATGCGTG GTGGTGGACGTGAGCCACGAAGACCCTGAGGTCAAGTTC AACTGGTACGTGGACGGCGTGGAGGTGCATAATGCCAAG ACAAAGCCGCGGGAGGAGCAGTACAACAGCACGTACCGT GTGGTCAGCGTCCTCACCGTCCTGCACCAGGACTGGCTGA ATGGCAAGGAGTACAAGTGCAAGGTCTCCAACAAAGCCC GCCCAGCCCCCATCGAGAAAACCATCTCCAAAGCCAAAG GGCAGCCCCGAGAACCACAGGTGACCACCCTGCCCCCAT CCCGGGATGAGCTGACCAAGAACCAGGTCAGCCTGACCT GCCTGGTCAAAGGCTTCTATCCCAGCGACATCGCCGTGG AGTGGGAGAGCAATGGGCAGCCGGAGAACAACTACAAG ACCTTCCCTCCCGTGCTGGACTCCGACGGCTCCTTCTTCCT CTACAGCAAGCTCACCGTGGACAAGAGCAGGTGGCAGCA GGGGAACGTCTTCTCATGCTCTGTGATGCATGAGGCTCTG AAATTCCACTACACGCAGAAGAGCCTCTCCCTGTCTCCGG GTAAA | 1 |
| HER2-Seldeg with MST-HN, knobs-into-holes and arginine mutations | ACCCAAGTGTGCACCGGCACAGACATGAAGCTGCGG TABLE 1-continued DNA sequences of polynucleotides encoding exemplary proteins.

| Polynucleotide encoding protein | DNA sequence | SEQ ID NO: |
|---|---|---|
| | TGCCCCATCAACTGCACCCACTCCTGTGTGGACCTGGATG<br>ACAAGGGCTGCCCCGCCGAGCAGAGAGCCAGCCCTCTGA<br>CGATTGAAGGCCGCATGGATCCCAAATCTTCTGACAAAA<br>CTCACACATGCCCACCGTGCCCAGCACCTGAACTCCTGA<br>GGGGACCGTCAGTCTTCCTCTTCCCCCCAAAACCCAAGGA<br>CACCCTCTACATCACTCGGGAACCTGAGGTCACATGCGTG<br>GTGGTGGACGTGAGCCACGAAGACCCTGAGGTCAAGTTC<br>AACTGGTACGTGGACGGCGTGGAGGTGCATAATGCCAAG<br>ACAAAGCCGCGGGAGGAGCAGTACAACAGCACGTACCGT<br>GTGGTCAGCGTCCTCACCGTCCTGCACCAGGACTGGCTGA<br>ATGGCAAGGAGTACAAGTGCAAGGTCTCCAACAAAGCCC<br>GCCCAGCCCCCATCGAGAAAACCATCTCCAAAGCCAAAG<br>GGCAGCCCCGAGAACCACAGGTGACCACCCTGCCCCCAT<br>CCCGGGATGAGCTGACCAAGAACCAGGTCAGCCTGACCT<br>GCCTGGTCAAAGGCTTCTATCCCAGCGACATCGCCGTGG<br>AGTGGGAGAGCAATGGGCAGCCGGAGAACAACTACAAG<br>ACCTTCCCTCCCGTGCTGGACTCCGACGGCTCCTTCTTCCT<br>CTACAGCAAGCTCACCGTGGACAAGAGCAGGTGGCAGCA<br>GGGGAACGTCTTCTCATGCTCTGTGATGCATGAGGCTCTG<br>AAATTCCACTACACGCAGAAGAGCCTCTCCCTGTCTCCTG<br>GTAAA | |
| Fc with MST-HN, knobs-into-holes and arginine mutations | GTTGAGCCCAAATCTTCTGACAAAACTCACACATGCCCAC<br>CGTGCCCAGCACCTGAACTCCTGAGGGGACCGTCAGTCTT<br>CCTCTTCCCCCCAAAACCCAAGGACACCCTCTACATCACT<br>CGGGAACCTGAGGTCACATGCGTGGTGGTGGACGTGAGC<br>CACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCCT<br>CACCGTCCTGCACCAGGACTGGCTGAATGGCAAGGAGTA<br>CAAGTGCAAGGTCTCCAACAAAGCCCGCCCAGCCCCCAT<br>CGAGAAAACCATCTCCAAAGCCAAAGGGCAGCCCCGAGA<br>ACCACAGGTGTACACCCTGCCCCCATCCCGGGATGAGCT<br>GACCAAGAACCAGGTCCACCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCGCCCTCTACAGCAAGCTC<br>ACCGTGGACAAGAGCAGGTGGCAGCAGGGGAACGTCTTC<br>TCATGCTCCGTGATGCATGAGGCTCTGAAATTCCACTACA<br>CGCAGAAGAGCCTCTCCCTGTCTCCGGGTAAA | 5 |
| MOG-Seldeg-PS with knobs-into-holes and arginine mutations | GGACAATTCAGAGTGATAGGACCAGGGTATCCCATCCGG<br>GCTTTAGTTGGGGATGAAGCAGAGCTGCCGTGCCGCATC<br>TCTCCTGGGAAAAATGCCACGGGCATGGAGGTGGGTTGG<br>TACCGTTCTCCCTTCTCAAGAGTGGTTCACCTCTACCGAA<br>ATGGCAAGGACCAAGATGCAGAGCAAGCACCTGAATACC<br>GGGGACGCACAGAGCTTCTGAAAGAGACTATCAGTGAGG<br>GAAAGGTTACCCTTAGGATTCAGAACGTGAGATTCTCAG<br>ATGAAGGAGGCTACACCTGCTTCTTCAGAGACCACTCTTA<br>CCAAGAAGAGGCAGCAATGGAGTTGAAAGTGGAAGATG<br>GAGGCGGTGGATCAGTTGAGCCCAAATCTTCTGACAAAA<br>CTCACACATGCCCACCGTGCCCAGCACCTGAACTCCTGA<br>GGGGACCGTCAGTCTTCCTCTTCCCCCCAAAACCCAAGGA<br>CACCCTCATGATCTCCCGGACCCCTGAGGTCACATGCGTG<br>GTGGTGGACGTGAGCCACGAAGACCCTGAGGTCAAGTTC<br>AACTGGTACGTGGACGGCGTGGAGGTGCATAATGCCAAG<br>ACAAAGCCGCGGGAGGAGCAGTACAACAGCACGTACCGT<br>GTGGTCAGCGTCCTCACCGTCCTGCACCAGGACTGGCTGA<br>ATGGCAAGGAGTACAAGTGCAAGGTCTCCAACAAAGCCC<br>GCCCAGCCCCCATCGAGAAAACCATCTCCAAAGCCAAAG<br>GGCAGCCCCGAGAACCACAGGTGACCACCCTGCCCCCAT<br>CCCGGGATGAGCTGACCAAGAACCAGGTCAGCCTGACCT<br>GCCTGGTCAAAGGCTTCTATCCCAGCGACATCGCCGTGG<br>AGTGGGAGAGCAATGGGCAGCCGGAGAACAACTACAAG<br>ACCTTCCCTCCCGTGCTGGACTCCGACGGCTCCTTCTTCCT<br>CTACAGCAAGCTCACCGTGGACAAGAGCAGGTGGCAGCA<br>GGGGAACGTCTTCTCATGCTCTGTGATGCATGAGGCTCTG<br>CATAACCACTACACGCAGAAGAGCCTCTCCCTGTCTCCGG<br>GTAAAGGAGGCGGTGGATCAGAGAAACTGGGAAAACTTC<br>AGTATTCACTGGATTATGATTTCCAAAATAACGCTGCT<br>GGTAGGGATCATTCAGGCTGCCGAACTGCCCGCCTTGGA<br>CATGGGGGGCACATCTGATCCTTACGTGAAAGTGTTTCTG<br>CTACCTGATAAGAAGAAGAAATTTGAGACAAAAGTCCAC<br>CGAAAAACCCTTAATCCTGTCTTCAATGAGCAATTTACTT<br>TCAAGGTACCATACTCGGAATTGGGTGGCAAAACCCTAG | 7 |

TABLE 1-continued

DNA sequences of polynucleotides encoding exemplary proteins.

| Polynucleotide encoding protein | DNA sequence | SEQ ID NO: |
|---|---|---|
| | TGATGGCTGTATATGATTTTGATCGTTTCTCTAAGCATGA<br>CATCATTGGAGAATTTAAAGTCCCTATGAACACAGTGGA<br>TTTTGGCCATGTAACTGAGGAATGGCGTGACCTGCAAAG<br>TGCT | |
| Fc-Syt1 with knobs-into-holes and arginine mutations | GTTGAGCCCAAATCTTCTGACAAAACTCACACATGCCCAC<br>CGTGCCCAGCACCTGAACTCCTGAGGGGACCGTCAGTCTT<br>CCTCTTCCCCCCAAAACCCAAGGACACCCTCATGATCTCC<br>CGGACCCCTGAGGTCACATGCGTGGTGGTGGACGTGAGC<br>CACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCCT<br>CACCGTCCTGCACCAGGACTGGCTGAATGGCAAGGAGTA<br>CAAGTGCAAGGTCTCCAACAAAGCCCGCCCAGCCCCCAT<br>CGAGAAAACCATCTCCAAAGCCAAAGGGCAGCCCCGAGA<br>ACCACAGGTGTACACCCTGCCCCCATCCCGGGATGAGCT<br>GACCAAGAACCAGGTCCACCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCGCCCTCTACAGCAAGCTC<br>ACCGTGGACAAGAGCAGGTGGCAGCAGGGGAACGTCTTC<br>TCATGCTCCGTGATGCATGAGGCTCTGCACAACCACTACA<br>CGCAGAAGAGCCTCTCCCTGTCTCCGGGTAAAGGAGGCG<br>GTGGATCAGAGAAACTGGGAAAACTTCAGTATTCACTGG<br>ATTATGATTTCCAAAATAACCAGCTGCTGGTAGGGATCAT<br>TCAGGCTGCCGAACTGCCCGCCTTGGACATGGGGGGCAC<br>ATCTGATCCTTACGTGAAAGTGTTTCTGCTACCTGATAAG<br>AAGAAGAAATTTGAGACAAAAGTCCACCGAAAAACCCTT<br>AATCCTGTCTTCAATGAGCAATTTACTTTCAAGGTACCAT<br>ACTCGGAATTGGGTGGCAAAACCCTAGTGATGGCTGTAT<br>ATGATTTTGATCGTTTCTCTAAGCATGACATCATTGGAGA<br>ATTTAAAGTCCCTATGAACACAGTGGATTTTGGCCATGTA<br>ACTGAGGAATGGCGTGACCTGCAAAGTGCT | 9 |
| MOG-Seldeg-PS with knobs-into-holes, electrostatic steering and arginine mutations | GGACAATTCAGAGTGATAGGACCAGGGTATCCCATCCGG<br>GCTTTAGTTGGGGATGAAGCAGAGCTGCCGTGCCGCATC<br>TCTCCTGGGAAAAATGCCACGGGCATGGAGGTGGGTTGG<br>TACCGTTCTCCCTTCTCAAGAGTGGTTCACCTCTACCGAA<br>ATGGCAAGGACCAAGATGCAGAGCAAGCACCTGAATACC<br>GGGGACGCACAGAGCTTCTGAAAGAGACTATCAGTGAGG<br>GAAAGGTTACCCTTAGGATTCAGAACGTGAGATTCTCAG<br>ATGAAGGAGGCTACACCTGCTTCTTCAGAGACCACTCTTA<br>CCAAGAAGAGGCAGCAATGGAGTTGAAAGTGGAAGATG<br>GAGGCGGTGGATCAGTTGAGCCCAAATCTTCTGACAAAA<br>CTCACACATGCCCACCGTGCCCAGCACCTGAACTCCTGA<br>GGGGACCGTCAGTCTTCCTCTTCCCCCCAAAACCCAAGGA<br>CACCCTCATGATCTCCCGGACCCCTGAGGTCACATGCGTG<br>GTGGTGGACGTGAGCCACGAAGACCCTGAGGTCAAGTTC<br>AACTGGTACGTGGACGGCGTGGAGGTGCATAATGCCAAG<br>ACAAAGCCGCGGGAGGAGCAGTACAACAGCACGTACCGT<br>GTGGTCAGCGTCCTCACCGTCCTGCACCAGGACTGGCTGA<br>ATGGCAAGGAGTACAAGTGCAAGGTCTCCAACAAAGCCC<br>GCCCAGCCCCCATCGAGAAAACCATCTCCAAAGCCAAAG<br>GGCAGCCCCGAGAACCACAGGTGACCACCCTGCCCCCAT<br>CCCGGGATGAGCTGACCAAGAACCAGGTCAGCCTGACCT<br>GCCTGGTCAAAGGCTTCTATCCCAGCGACATCGCCGTGG<br>AGTGGGAGAGCAATGGGCAGCCGGAGAACAACTACGAC<br>ACCTTCCCTCCCGTGCTGGACTCCGACGGCTCCTTCTTCCT<br>CTACAGCGACCTCACCGTGGACAAGAGCAGGTGGCAGCA<br>GGGGAACGTCTTCTCATGCTCTGTGATGCATGAGGCTCTG<br>CATAACCACTACACGCAGAAGAGCCTCTCCCTGTCTCCGG<br>GTAAAGGAGGCGGTGGATCAGAGAAACTGGGAAAACTTC<br>AGTATTCACTGGATTATGATTTCCAAAATAACCAGCTGCT<br>GGTAGGGATCATTCAGGCTGCCGAACTGCCCGCCTTGGA<br>CATGGGGGGCACATCTGATCCTTACGTGAAAGTGTTTCTG<br>CTACCTGATAAGAAGAAGAAATTTGAGACAAAAGTCCAC<br>CGAAAAACCCTTAATCCTGTCTTCAATGAGCAATTTACTT<br>TCAAGGTACCATACTCGGAATTGGGTGGCAAAACCCTAG<br>TGATGGCTGTATATGATTTTGATCGTTTCTCTAAGCATGA<br>CATCATTGGAGAATTTAAAGTCCCTATGAACACAGTGGA<br>TTTTGGCCATGTAACTGAGGAATGGCGTGACCTGCAAAG<br>TGCT | 11 |

TABLE 1-continued

DNA sequences of polynucleotides encoding exemplary proteins.

| Polynucleotide encoding protein | DNA sequence | SEQ ID NO: |
|---|---|---|
| Fc-Syt1 with knobs-into-holes, electrostatic steering and arginine mutations | GTTGAGCCCAAATCTTCTGACAAAACTCACACATGCCCAC CGTGCCCAGCACCTGAACTCCTGAGGGGACCGTCAGTCTT CCTCTTCCCCCCAAAACCCAAGGACACCCTCATGATCTCC CGGACCCCTGAGGTCACATGCGTGGTGGTGGACGTGAGC CACGAAGACCCTGAGGTCAAGTTCAACTGGTACGTGGAC GGCGTGGAGGTGCATAATGCCAAGACAAAGCCGCGGGA GGAGCAGTACAACAGCACGTACCGTGTGGTCAGCGTCCT CACCGTCCTGCACCAGGACTGGCTGAATGGCAAGGAGTA CAAGTGCAAGGTCTCCAACAAAGCCCGCCCAGCCCCCAT CGAGAAAACCATCTCCAAAGCCAAAGGGCAGCCCCGAGA ACCACAGGTGTACACCCTGCCCCCATCCCGGGATAAGCT GACCAAGAACCAGGTCCACCTGACCTGCCTGGTCAAAGG CTTCTATCCCAGCGACATCGCCGTGGAGTGGGAGAGCAA TGGGCAGCCGGAGAACAACTACAAGACCACGCCTCCCGT GCTGAAGTCCGACGGCTCCTTCGCCCTCTACAGCAAGCTC ACCGTGGACAAGAGCAGGTGGCAGCAGGGGAACGTCTTC TCATGCTCCGTGATGCATGAGGCTCTGCACAACCACTACA CGCAGAAGAGCCTCTCCCTGTCTCCGGGTAAAGGAGGCG GTGGATCAGAGAAACTGGGAAAACTTCAGTATTCACTGG ATTATGATTTCCAAAATAACCAGCTGCTGGTAGGGATCAT TCAGGCTGCCGAACTGCCCGCCTTGGACATGGGGGGCAC ATCTGATCCTTACGTGAAAGTGTTTCTGCTACCTGATAAG AAGAAGAAATTTGAGACAAAAGTCCACCGAAAAACCCTT AATCCTGTCTTCAATGAGCAATTTACTTTCAAGGTACCAT ACTCGGAATTGGGTGGCAAAACCCTAGTGATGGCTGTAT ATGATTTTGATCGTTTCTCTAAGCATGACATCATTGGAGA ATTTAAAGTCCCTATGAACACAGTGGATTTTGGCCATGTA ACTGAGGAATGGCGTGACCTGCAAAGTGCT | 13 |
| MOG-Seldeg-TfR with knobs-into-holes mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGCTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGGGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTTACCGTCCTGCACCAGGACTGGCTGAATGGC AAGGAGTACAAGTGCAAGGTCTCCAACAAAGCCCTCCCA GCCCCCATCGAGAAAACCATCTCCAAAGCCAAAGGGCAG CCCCGAGAACCACAGGTGACCACCCTGCCCCCATCCCGG GATGAGCTGACCAAGAACCAGGTCAGCCTGACCTGCCTG GTCAAAGGCTTCTATCCCAGCGACATCGCCGTGGAGTGG GAGAGCAATGGGCAGCCGGAGAACAACTACAAGACCTTC CCTCCCGTGCTGGACTCCGACGGCTCCTTCTTCCTCTACA GCAAGCTCACCGTGGACAAGAGCAGGTGGCAGCAGGGG AACGTCTTCTCATGCTCCGTGATGCATGAGGCTCTGCACA ACCACTACACGCAGAAGAGCCTCTCCCTGTCTCCGGGTA AAGGAGGCGGTGGATCAGGACAATTCAGAGTGATAGGAC CAGGGTATCCCATCCGGGCTTTAGTTGGGGATGAAGCAG AGCTGCCGTGCCGCATCTCTCCTGGGAAAAATGCCACGG GCATGGAGGTGGGTTGGTACCGTTCTCCCTTCTCAAGAGT GGTTCACCTCTACCGAAATGGCAAGGACCAAGATGCAGA GCAAGCACCTGAATACCGGGACGCACAGAGCTTCTGAA AGAGACTATCAGTGAGGGAAAGGTTACCCTTAGGATTCA GAACGTGAGATTCTCAGATGAAGGAGGCTACACCTGCTT CTTCAGAGACCACTCTTACCAAGAAGAGGCAGCAATGGA GTTGAAAGTGGAAGAT | 15 |

TABLE 1-continued

DNA sequences of polynucleotides encoding exemplary proteins.

| Polynucleotide encoding protein | DNA sequence | SEQ ID NO: |
|---|---|---|
| TfR Ab with knobs-into-holes mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGGGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG GTACGTGGACGGCGTGGAGGTGCATAATGCCAAGACAAA GCCGCGGGAGGAGCAGTACAACAGCACGTACCGTGTGGT CAGCGTCCTCACCGTCCTGCACCAGGACTGGCTGAATGG CAAGGAGTACAAGTGCAAGGTCTCCAACAAAGCCCTCCC AGCCCCCATCGAGAAAACCATCTCCAAAGCCAAAGGGCA GCCCCGAGAACCACAGGTGTACACCCTGCCCCCATCCCG GGATGAGCTGACCAAGAACCAGGTCCACCTGACCTGCCT GGTCAAAGGCTTCTATCCCAGCGACATCGCCGTGGAGTG GGAGAGCAATGGGCAGCCGGAGAACAACTACAAGACCA CGCCTCCCGTGCTGGACTCCGACGGCTCCTTCGCCCTCTA CAGCAAGCTCACCGTGGACAAGAGCAGGTGGCAGCAGG GGAACGTCTTCTCATGCTCCGTGATGCATGAGGCTCTGCA CAACCACTACACGCAGAAGAGCCTCTCCCTGTCTCCGGGT AAA | 17 |
| TfR Ab LC | GACATCCAGATGACCCAGTCCCCCTCCTCCCTGTCCGCCT CCGTGGGCGACCGGGTGACCATCACCTGCCGGGCCTCCG ACAACCTGTACTCCAACCTGGCCTGGTACCAGCAGAAGC CCGGCAAGTCCCCCAAGCTGCTGGTGTACGACGCCACCA ACCTGGCCGACGGCGTGCCCTCCCGGTTCTCCGGCTCCGG CTCCGGCACCGACTACACCCTGACCATCTCCTCCCTGCAG CCCGAGGACTTCGCCACCTACTACTGCCAGCACTTCTGGG GCACCCCCCTGACCTTCGGCCAGGGCACCAAGGTGGAGA TCAAGACTGTGGCTGCACCATCTGTCTTCATCTTCCCGCC ATCTGATGAGCAGTTGAAATCTGGAACTGCCTCTGTTGTG TGCCTGCTGAATAACTTCTATCCCAGAGAGGCCAAAGTA CAGTGGAAGGTGGATAACGCCCTCCAATCGGGTAACTCC CAGGAGAGTGTCACAGAGCAGGACAGCAAGGACAGCAC CTACAGCCTCAGCAGCACCCTGACGCTGAGCAAAGCAGA CTACGAGAAACACAAAGTCTACGCCTGCGAAGTCACCCA TCAGGGCCTGAGTTCGCCCGTCACAAAGAGCTTCAACAG GGGAGAGTGT | 19 |
| MOG-Seldeg-TfR with knobs-into-holes and arginine mutations | GAGGTGCAGCTGGTGCAGTCCGGCGCCGAGGTGAAGAAG CCCGGCGCCTCCGTGAAGGTGTCCTGCAAGGCCTCCGGCT ACACCTTCACCTCCTACTGGATGCACTGGGTGCGGCAGGC CCCCGGCCAGCGGCTGGAGTGGATCGGCGAGATCAACCC CACCAACGGCCGGACCAACTACATCGAGAAGTTCAAGTC CCGGGCCACCCTGACCGTGGACAAGTCCGCCTCCACCGC CTACATGGAGCTGTCCTCCCTGCGGTCCGAGGACACCGCC GTGTACTACTGCGCCCGGGGCACCCGGGCCTACCACTACT GGGGCCAGGGCACCATGGTGACCGTGTCCTCCGCCTCCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGC TGTCCTACAGTCCTCAGGACTCTACTCCCTCAGCAGCGTG GTGACTGTGCCCTCCAGCAGCTTGGGCACCCAGACCTAC ATCTGCAACGTGAATCACAAGCCCAGCAACACCAAGGTG GACAAGAAAGTTGAGCCCAAATCTTGTGACAAAACTCAC ACATGCCCACCGTGCCCAGCACCTGAACTCCTGAGGGGA CCGTCAGTCTTCCTCTTCCCCCCAAAACCCAAGGACACCC TCATGATCTCCCGGACCCCTGAGGTCACATGCGTGGTGGT GGACGTGAGCCACGAAGACCCTGAGGTCAAGTTCAACTG | 21 |

TABLE 1-continued

DNA sequences of polynucleotides encoding exemplary proteins.

| Polynucleotide encoding protein | DNA sequence | SEQ ID NO: |
|---|---|---|
| | GTACGTGGACGGCGTGGAGGTGCATAATGCCAAGACAAA<br>GCCGCGGGAGGAGCAGTACAACAGCACGTACCGTGTGGT<br>CAGCGTCCTTACCGTCCTGCACCAGGACTGGCTGAATGGC<br>AAGGAGTACAAGTGCAAGGTCTCCAACAAAGCCCGCCCA<br>GCCCCCATCGAGAAAACCATCTCCAAAGCCAAAGGGCAG<br>CCCCGAGAACCACAGGTGACCACCCTGCCCCCATCCCGG<br>GATGAGCTGACCAAGAACCAGGTCAGCCTGACCTGCCTG<br>GTCAAAGGCTTCTATCCCAGCGACATCGCCGTGGAGTGG<br>GAGAGCAATGGGCAGCCGGAGAACAACTACAAGACCTTC<br>CCTCCCGTGCTGGACTCCGACGGCTCCTTCTTCCTCTACA<br>GCAAGCTCACCGTGGACAAGAGCAGGTGGCAGCAGGGG<br>AACGTCTTCTCATGCTCCGTGATGCATGAGGCTCTGCACA<br>ACCACTACACGCAGAAGAGCCTCTCCCTGTCTCCGGGTA<br>AAGGAGGCGGTGGATCAGGACAATTCAGAGTGATAGGAC<br>CAGGGTATCCCATCCGGGCTTTAGTTGGGGATGAAGCAG<br>AGCTGCCGTGCCGCATCTCTCCTGGGAAAAATGCCACGG<br>GCATGGAGGTGGGTTGGTACCGTTCTCCCTTCTCAAGAGT<br>GGTTCACCTCTACCGAAATGGCAAGGACCAAGATGCAGA<br>GCAAGCACCTGAATACCGGGGACGCACAGAGCTTCTGAA<br>AGAGACTATCAGTGAGGGAAAGGTTACCCTTAGGATTCA<br>GAACGTGAGATTCTCAGATGAAGGAGGCTACACCTGCTT<br>CTTCAGAGACCACTCTTACCAAGAAGAGGCAGCAATGGA<br>GTTGAAAGTGGAAGAT | |
| TfR Ab with knobs-into-holes and arginine mutations | GAGGTGCAGCTGGTGCAGTCCGGCGCCGAGGTGAAGAAG<br>CCCGGCGCCTCCGTGAAGGTGTCCTGCAAGGCCTCCGGCT<br>ACACCTTCACCTCCTACTGGATGCACTGGGTGCGGCAGGC<br>CCCCGGCCAGGGCGGCTGGAGTGGATCGGCGAGATCAACCC<br>CACCAACGGCCGGACCAACTACATCGAGAAGTTCAAGTC<br>CCGGGCCACCCTGACCGTGGACAAGTCCGCCTCCACCGC<br>CTACATGGAGCTGTCCTCCCTGCGGTCCGAGGACACCGCC<br>GTGTACTACTGCGCCCGGGGCACCCGGGCCTACCACTACT<br>GGGGCCAGGGCACCATGGTGACCGTGTCCTCCGCCTCCA<br>CCAAGGGCCCATCGGTCTTCCCCCTGGCACCCTCCTCCAA<br>GAGCACCTCTGGGGGCACAGCGGCCCTGGGCTGCCTGGT<br>CAAGGACTACTTCCCCGAACCGGTGACGGTGTCGTGGAA<br>CTCAGGCGCCCTGACCAGCGGCGTGCACACCTTCCCGGC<br>TGTCCTACAGTCCTCAGGACTCTACTCCCTCAGCAGCGTG<br>GTGACTGTGCCCTCCAGCAGCTTGGGCACCCAGACCTAC<br>ATCTGCAACGTGAATCACAAGCCCAGCAACACCAAGGTG<br>GACAAGAAAGTTGAGCCCAAATCTTGTGACAAAACTCAC<br>ACATGCCCACCGTGCCCAGCACCTGAACTCCTGAGGGGA<br>CCGTCAGTCTTCCTCTTCCCCCCAAAACCCAAGGACACCC<br>TCATGATCTCCCGGACCCCTGAGGTCACATGCGTGGTGGT<br>GGACGTGAGCCACGAAGACCCTGAGGTCAAGTTCAACTG<br>GTACGTGGACGGCGTGGAGGTGCATAATGCCAAGACAAA<br>GCCGCGGGAGGAGCAGTACAACAGCACGTACCGTGTGGT<br>CAGCGTCCTCACCGTCCTGCACCAGGACTGGCTGAATGG<br>CAAGGAGTACAAGTGCAAGGTCTCCAACAAAGCCCGCCC<br>AGCCCCCATCGAGAAACCATCTCCAAAGCCAAAGGGCA<br>GCCCCGAGAACCACAGGTGTACACCCTGCCCCCATCCCG<br>GGATGAGCTGACCAAGAACCAGGTCCACCTGACCTGCCT<br>GGTCAAAGGCTTCTATCCCAGCGACATCGCCGTGGAGTG<br>GGAGAGCAATGGGCAGCCGGAGAACAACTACAAGACCA<br>CGCCTCCCGTGCTGGACTCCGACGGCTCCTTCGCCCTCTA<br>CAGCAAGCTCACCGTGGACAAGAGCAGGTGGCAGCAGG<br>GGAACGTCTTCTCATGCTCCGTGATGCATGAGGCTCTGCA<br>CAACCACTACACGCAGAAGAGCCTCTCCCTGTCTCCGGGT<br>AAA | 23 |
| HER2-ECD-Fc with MST-HN and knobs-into-holes | ACCCAAGTGTGCACCGGCACAGACATGAAGCTGCGGCTC<br>CCTGCCAGTCCCGAGACCCACCTGGACATGCTCCGCCAC<br>CTCTACCAGGGCTGCCAGGTGGTGCAGGGAAACCTGGAA<br>CTCACCTACCTGCCCACCAATGCCAGCCTGTCCTTCCTGC<br>AGGATATCCAGGAGGTGCAGGGCTACGTGCTCATCGCTC<br>ACAACCAAGTGAGGCAGGTCCCACTGCAGAGGCTGCGGA<br>TTGTGCGAGGCACCCAGCTCTTTGAGGACAACTATGCCCT<br>GGCCGTGCTAGACAATGGAGACCCGCTGAACAATACCAC<br>CCCTGTCACAGGGGCCTCCCCAGGAGGCCTGCGGGAGCT<br>GCAGCTTCGAAGCCTCACAGAGATCTTGAAAGGAGGGGT<br>CTTGATCCAGCGGAACCCCCAGCTCTGCTACCAGGACAC<br>GATTTTGTGGAAGGACATCTTCCACAAGAACAACCAGCT<br>GGCTCTCACACTGATAGACACCAACCGCTCTCGGGCCTGC<br>CACCCCTGTTCTCCGATGTGTAAGGGCTCCCGCTGCTGGG<br>GAGAGAGTTCTGAGGATTGTCAGAGCCTGACGCGCACTG | 25 |

TABLE 1-continued

DNA sequences of polynucleotides encoding exemplary proteins.

| Polynucleotide encoding protein | DNA sequence | SEQ ID NO: |
|---|---|---|
| | TCTGTGCCGGTGGCTGTGCCCGCTGCAAGGGGCCACTGCC<br>CACTGACTGCTGCCATGAGCAGTGTGCTGCCGGCTGCAC<br>GGGCCCCAAGCACTCTGACTGCCTGGCCTGCCTCCACTTC<br>AACCACAGTGGCATCTGTGAGCTGCACTGCCCAGCCCTG<br>GTCACCTACAACACAGACACGTTTGAGTCCATGCCCAATC<br>CCGAGGGCCGGTATACATTCGGCGCCAGCTGTGTGACTG<br>CCTGTCCCTACAACTACCTTTCTACGGACGTGGGATCCTG<br>CACCCTCGTCTGCCCCCTGCACAACCAAGAGGTGACAGC<br>AGAGGATGGAACACAGCGGTGTGAGAAGTGCAGCAAGC<br>CCTGTGCCCGAGTGTGCTATGGTCTGGGCATGGAGCACTT<br>GCGAGAGGTGAGGGCAGTTACCAGTGCCAATATCCAGGA<br>GTTTGCTGGCTGCAAGAAGATCTTTGGGAGCCTGGCATTT<br>CTGCCGGAGAGCTTTGATGGGGACCCAGCCTCCAACACT<br>GCCCCGCTCCAGCCAGAGCAGCTCCAAGTGTTTGAGACT<br>CTGGAAGAGATCACAGGTTACCTATACATCTCAGCATGG<br>CCGGACAGCCTGCCTGACCTCAGCGTCTTCCAGAACCTGC<br>AAGTAATCCGGGGACGAATTCTGCACAATGGCGCCTACT<br>CGCTGACCCTGCAAGGGCTGGGCATCAGCTGGCTGGGGC<br>TGCGCTCACTGAGGGAACTGGGCAGTGGACTGGCCCTCA<br>TCCACCATAACACCCACCTCTGCTTCGTGCACACGGTGCC<br>CTGGGACCAGCTCTTTCGGAACCCGCACCAAGCTCTGCTC<br>CACACTGCCAACCGGCCAGAGGACGAGTGTGTGGGCGAG<br>GGCCTGGCCTGCCACCAGCTGTGCGCCCGAGGGCACTGC<br>TGGGGTCCAGGGCCCACCCAGTGTGTCAACTGCAGCCAG<br>TTCCTTCGGGGCCAGGAGTGCGTGGAGGAATGCCGAGTA<br>CTGCAGGGGCTCCCCAGGGAGTATGTGAATGCCAGGCAC<br>TGTTTGCCGTGCCACCCTGAGTGTCAGCCCCAGAATGGCT<br>CAGTGACCTGTTTTGGACCGGAGGCTGACCAGTGTGTGG<br>CCTGTGCCCACTATAAGGACCCTCCCTTCTGCGTGGCCG<br>CTGCCCCAGCGGTGTGAAACCTGACCTCTCCTACATGCCC<br>ATCTGGAAGTTTCCAGATGAGGAGGGCGCATGCCAGCCT<br>TGCCCCATCAACTGCACCCACTCCTGTGTGGACCTGGATG<br>ACAAGGGCTGCCCCGCCGAGCAGAGAGCCAGCCCTCTGA<br>CGATTGAAGGCCGCATGGATCCCAAATCTTCTGACAAAA<br>CTCACACATGCCCACCGTGCCCAGCACCTGAACTCCTGG<br>GGGGACCGTCAGTCTTCCTCTTCCCCCCAAAACCCAAGGA<br>CACCCTCTACATCACTCGGGAACCTGAGGTCACATGCGTG<br>GTGGTGGACGTGAGCCACGAAGACCCTGAGGTCAAGTTC<br>AACTGGTACGTGGACGGCGTGGAGGTGCATAATGCCAAG<br>ACAAAGCCGCGGGAGGAGCAGTACAACAGCACGTACCGT<br>GTGGTCAGCGTCCTCACCGTCCTGCACCAGGACTGGCTGA<br>ATGGCAAGGAGTACAAGTGCAAGGTCTCCAACAAAGCCC<br>TCCCAGCCCCCATCGAGAAAACCATCTCCAAAGCCAAAG<br>GGCAGCCCCGAGAACCACAGGTGACCACCCTGCCCCCAT<br>CCCGGGATGAGCTGACCAAGAACCAGGTCAGCCTGACCT<br>GCCTGGTCAAAGGCTTCTATCCCAGCGACATCGCCGTGG<br>AGTGGGAGAGCAATGGGCAGCCGGAGAACAACTACAAG<br>ACCTTCCCTCCCGTGCTGGACTCCGACGGCTCCTTCTTCCT<br>CTACAGCAAGCTCACCGTGGACAAGAGCAGGTGGCAGCA<br>GGGGAACGTCTTCTCATGCTCTGTGATGCATGAGGCTCTG<br>AAATTCCACTACACGCAGAAGAGCCTCTCCCTGTCTCCTG<br>GTAAA | |
| Fc with MST-HN and knobs-into-holes mutations | GTTGAGCCCAAATCTTCTGACAAAACTCACACATGCCCAC<br>CGTGCCCAGCACCTGAACTCCTGGGGGGACCGTCAGTCTT<br>CCTCTTCCCCCCAAAACCCAAGGACACCCTCTACATCACT<br>CGGGAACCTGAGGTCACATGCGTGGTGGTGGACGTGAGC<br>CACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCCT<br>CACCGTCCTGCACCAGGACTGGCTGAATGGCAAGGAGTA<br>CAAGTGCAAGGTCTCCAACAAAGCCCTCCCAGCCCCCAT<br>CGAGAAAACCATCTCCAAAGCCAAAGGGCAGCCCCGAGA<br>ACCACAGGTGTACACCCTGCCCCCATCCCGGGATGAGCT<br>GACCAAGAACCAGGTCCACCTGACCTGCCTGGTCAAAGG<br>CTTCTATCCCAGCGACATCGCCGTGGAGTGGGAGAGCAA<br>TGGGCAGCCGGAGAACAACTACAAGACCACGCCTCCCGT<br>GCTGGACTCCGACGGCTCCTTCGCCCTCTACAGCAAGCTC<br>ACCGTGGACAAGAGCAGGTGGCAGCAGGGGAACGTCTTC<br>TCATGCTCCGTGATGCATGAGGCTCTGAAATTCCACTACA<br>CGCAGAAGAGCCTCTCCCTGTCTCCGGGTAAA | 27 |

TABLE 1-continued

DNA sequences of polynucleotides encoding exemplary proteins.

| Polynucleotide encoding protein | DNA sequence | SEQ ID NO: |
|---|---|---|
| PSMA-Seldeg with MST-HN, knobs-into-holes and arginine mutations | GTTGAGCCCAAATCTTCTGACAAAACTCACACATGCCCAC<br>CGTGCCCAGCACCTGAACTCCTGAGGGGACCGTCAGTCTT<br>CCTCTTCCCCCCAAAACCCAAGGACACCCTCTACATCACT<br>CGGGAACCTGAGGTCACATGCGTGGTGGTGGACGTGAGC<br>CACGAAGACCCTGAGGTCAAGTTCAACTGGTACGTGGAC<br>GGCGTGGAGGTGCATAATGCCAAGACAAAGCCGCGGGA<br>GGAGCAGTACAACAGCACGTACCGTGTGGTCAGCGTCCT<br>CACCGTCCTGCACCAGGACTGGCTGAATGGCAAGGAGTA<br>CAAGTGCAAGGTCTCCAACAAAGCCCGCCCAGCCCCCAT<br>CGAGAAAACCATCTCCAAAGCCAAAGGGCAGCCCCGAGA<br>ACCACAGGTGACCACCCTGCCCCCATCCCGGGATGAGCT<br>GACCAAGAACCAGGTCAGCCTGACCTGCCTGGTCAAAGG<br>CTTCTATCCCAGCGACATCGCCGTGGAGTGGGAGAGCAA<br>TGGGCAGCCGGAGAACAACTACAAGACCTTCCCTCCCGT<br>GCTGGACTCCGACGGCTCCTTCTTCCTCTACAGCAAGCTC<br>ACCGTGGACAAGAGCAGGTGGCAGCAGGGGAACGTCTTC<br>TCATGCTCTGTGATGCATGAGGCTCTGAATTCCACTACA<br>CGCAGAAGAGCCTCTCCCTGTCTCCGGGTAAAGGAGGCG<br>GTGGATCAAAATCCTCCAATGAAGCTACTAACATTACTCC<br>AAAGCATAATATGAAAGCATTTTTGGATGAATTGAAAGC<br>TGAGAACATCAAGAAGTTCTTATATAATTTTACACAGATA<br>CCACATTTAGCAGGAACAGAACAAAACTTTCAGCTTGCA<br>AAGCAAATTCAATCCCAGTGGAAAGAATTTGGCCTGGAT<br>TCTGTTGAGCTAGCACATTATGATGTCCTGTTGTCCTACC<br>CAAATAAGACTCATCCCAACTACATCTCAATAATTAATGA<br>AGATGGAAATGAGATTTTCAACACATCATTATTTGAACCA<br>CCTCCTCCAGGATATGAAAATGTTTCGGATATTGTACCAC<br>CTTTCAGTGCTTTCTCTCCTCAAGGAATGCCAGAGGGCGA<br>TCTAGTGTATGTTAACTATGCACGAACTGAAGACTTCTTT<br>AAATTGGAACGGGACATGAAAATCAATTGCTCTGGGAAA<br>ATTGTAATTGCCAGATATGGGAAAGTTTTCAGAGGAAAT<br>AAGGTTAAAAATGCCCAGCTGGCAGGGGCCAAAGGAGTC<br>ATTCTCTACTCCGACCCTGCTGACTACTTTGCTCCTGGGG<br>TGAAGTCCTATCCAGATGGTTGGAATCTTCCTGGAGGTGG<br>TGTCCAGCGTGGAAATATCCTAAATCTGAATGGTGCAGG<br>AGACCCTCTCACACCAGGTTACCCAGCAAATGAATATGC<br>TTATAGGCGTGGAATTGCAGAGGCTGTTGGTCTTCCAAGT<br>ATTCCTGTTCATCCAATTGGATACTATGATGCACAGAAGC<br>TCCTAGAAAAAATGGGTGGCTCAGCACCACCAGATAGCA<br>GCTGGAGAGGAAGTCTCAAAGTGCCCTACAATGTTGGAC<br>CTGGCTTTACTGGAAACTTTTCTACACAAAAAGTCAAGAT<br>GCACATCCACTCTACCAATGAAGTGACAAGAATTTACAA<br>TGTGATAGGTACTCTCAGAGGAGCAGTGGAACCAGACAG<br>ATATGTCATTCTGGGAGGTCACCGGGACTCATGGGTGTTT<br>GGTGGTATTGACCCTCAGAGTGGAGCAGCTGTTGTTCATG<br>AAATTGTGAGGAGCTTTGGAACACTGAAAAAGGAAGGGT<br>GGAGACCTAGAAGAACAATTTTGTTTGCAAGCTGGGATG<br>CAGAAGAATTTGGTCTTCTTGGTTCTACTGAGTGGGCAGA<br>GGAGAATTCAAGACTCCTTCAAGAGCGTGGCGTGGCTTA<br>TATTAATGCTGACTCATCTATAGAAGGAAACTACACTCTG<br>AGAGTTGATTGTACACCGCTGATGTACAGCTTGGTACACA<br>ACCTAACAAAAGAGCTGAAAAGCCCTGATGAAGGCTTTG<br>AAGGCAAATCTCTTTATGAAAGTTGGACTAAAAAAAGTC<br>CTTCCCCAGAGTTCAGTGGCATGCCCAGGATAAGCAAAT<br>TGGGATCTGGAAATGATTTTGAGGTGTTCTTCCAACGACT<br>TGGAATTGCTTCAGGCAGAGCACGGTATACTAAAAATTG<br>GGAAACAAACAAATTCAGCGGCTATCCACTGTATCACAG<br>TGTCTATGAAACATATGAGTTGGTGGAAAAGTTTTATGAT<br>CCAATGTTTAAATATCACCTCACTGTGGCCCAGGTTCGAG<br>GAGGGATGGTGTTTGAGCTAGCCAATTCCATAGTGCTCCC<br>TTTTGATTGTCGAGATTATGCTGTAGTTTTAAGAAAGTAT<br>GCTGACAAAATCTACAGTATTTCTATGAAACATCCACAG<br>GAAATGAAGACATACAGTGTATCATTTGATTCACTTTTTT<br>CTGCAGTAAAGAATTTTACAGAAATTGCTTCCAAGTTCAG<br>TGAGAGACTCCAGGACTTTGACAAAAGCAACCCAATAGT<br>ATTAAGAATGATGAATGATCAACTCATGTTTCTGGAAAG<br>AGCATTTATTGATCCATTAGGGTTACCAGACAGGCCTTTT<br>TATAGGCATGTCATCTATGCTCCAAGCAGCCACAACAAG<br>TATGCAGGGGAGTCATTCCCAGGAATTTATGATGCTCTGT<br>TTGATATTGAAAGCAAAGTGGACCCTTCCAAGGCCTGGG<br>GAGAAGTGAAGAGACAGATTTATGTTGCAGCCTTCACAG<br>TGCAGGCAGCTGCAGAGACTTTGAGTGAAGTAGCC | 29 |

TABLE 1-continued

DNA sequences of polynucleotides encoding exemplary proteins.

| Polynucleotide encoding protein | DNA sequence | SEQ ID NO: |
|---|---|---|
| GAD65-Seldeg with MST-HN, knobs-into-holes and arginine mutations | ATGGCATCTCCGGGCTCTGGCTTTTGGTCTTTCGGGTCGG<br>AAGATGGCTCTGGGGATTCCGAGAATCCCGGCACAGCGC<br>GAGCCTGGTGCCAAGTGGCTCAGAAGTTCACGGGCGGCA<br>TCGGAAACAAACTGTGCGCCCTGCTCTACGGAGACGCCG<br>AGAAGCCGGCGGAGAGCGGCGGGAGCCAACCCCCGCGG<br>GCCGCCGCCCGGAAGGCCGCCTGCGCCTGCGACCAGAAG<br>CCCTGCAGCTGCTCCAAAGTGGATGTCAACTACGCGTTTC<br>TCCATGCAACAGACCTGCTGCCGGCGTGTGATGGAGAAA<br>GGCCCACTTTGGCGTTTCTGCAAGATGTTATGAACATTTT<br>ACTTCAGTATGTGGTGAAAAGTTTCGATAGATCAACCAA<br>AGTGATTGATTTCCATTATCCTAATGAGCTTCTCCAAGAA<br>TATAATTGGGAATTGGCAGACCAACCACAAAATTTGGAG<br>GAAATTTTGATGCATTGCCAAACAACTCTAAAATATGCA<br>ATTAAAACAGGGCATCCTAGATACTTCAATCAACTTTCTA<br>CTGGTTTGGATATGGTTGGATTAGCAGCAGACTGGCTGAC<br>ATCAACAGCAAATACTAACATGTTCACCTATGAAATTGCT<br>CCAGTATTTGTGCTTTTGGAATATGTCACACTAAAGAAAA<br>TGAGAGAAATCATTGGCTGGCCAGGGGGCTCTGGCGATG<br>GGATATTTTCTCCCGGTGGCGCCATATCTAACATGTATGC<br>CATGATGATCGCACGCTTTAAGATGTTCCCAGAAGTCAA<br>GGAGAAAGGAATGGCTGCTCTTCCCAGGCTCATTGCCTTC<br>ACGTCTGAACATAGTCATTTTTCTCTCAAGAAGGGAGCTG<br>CAGCCTTAGGGATTGGAACAGACAGCGTGATTCTGATTA<br>AATGTGATGAGAGAGGGAAAATGATTCCATCTGATCTTG<br>AAAGAAGGATTCTTGAAGCCAAACAGAAAGGGTTTGTTC<br>CTTTCCTCGTGAGTGCCACAGCTGGAACCACCGTGTACGG<br>AGCATTTGACCCCCTCTTAGCTGTCGCTGACATTTGCAAA<br>AAGTATAAGATCTGGATGCATGTGGATGCAGCTTGGGGT<br>GGGGGATTACTGATGTCCCGAAAACACAAGTGGAAACTG<br>AGTGGCGTGGAGAGGGCCAACTCTGTGACGTGGAATCCA<br>CACAAGATGATGGGAGTCCCTTTGCAGTGCTCTGCTCTCC<br>TGGTTAGAGAAGAGGGATTGATGCAGAATTGCAACCAAA<br>TGCATGCCTCCTACCTCTTTCAGCAAGATAAACATTATGA<br>CCTGTCCTATGACACTGGAGACAAGGCCTTACAGTGCGG<br>ACGCCACGTTGATGTTTTTAAACTATGGCTGATGTGGAGG<br>GCAAAGGGGACTACCGGGTTTGAAGCGCATGTTGATAAA<br>TGTTTGGAGTTGGCAGAGTATTTATACAACATCATAAAAA<br>ACCGAGAAGGATATGAGATGGTGTTTGATGGGAAGCCTC<br>AGCACACAAATGTCTGCTTCTGGTACATTCCTCCAAGCTT<br>GCGTACTCTGGAAGACAATGAAGAGAGAATGAGTCGCCT<br>CTCGAAGGTGGCTCCAGTGATTAAAGCCAGAATGATGGA<br>GTATGGAACCACAATGGTCAGCTACCAACCCTTGGGAGA<br>CAAGGTCAATTTCTTCCGCATGGTCATCTCAAACCCAGCG<br>GCAACTCACCAAGACATTGACTTCCTGATTGAAGAAATA<br>GAACGCCTTGGACAAGATTTAGGAGGCGGTGGATCAGTT<br>GAGCCCAAATCTTCTGACAAAACTCACACATGCCCACCG<br>TGCCCAGCACCTGAACTCCTGAGGGGACCGTCAGTCTTCC<br>TCTTCCCCCCAAAACCCAAGGACACCCTCTACATCACTCG<br>GGAACCTGAGGTCACATGCGTGGTGGTGGACGTGAGCCA<br>CGAAGACCCTGAGGTCAAGTTCAACTGGTACGTGGACGG<br>CGTGGAGGTGCATAATGCCAAGACAAAGCCGCGGGAGG<br>AGCAGTACAACAGCACGTACCGTGTGGTCAGCGTCCTCA<br>CCGTCCTGCACCAGGACTGGCTGAATGGCAAGGAGTACA<br>AGTGCAAGGTCTCCAACAAAGCCCGCCCAGCCCCCATCG<br>AGAAAACCATCTCCAAAGCCAAAGGGCAGCCCCGAGAAC<br>CACAGGTGACCACCCTGCCCCCATCCCGGGATGAGCTGA<br>CCAAGAACCAGGTCAGCCTGACCTGCCTGGTCAAAGGCT<br>TCTATCCCAGCGACATCGCCGTGGAGTGGGAGAGCAATG<br>GGCAGCCGGAGAACAACTACAAGACCTTCCCTCCCGTGC<br>TGGACTCCGACGGCTCCTTCTTCCTCTACAGCAAGCTCAC<br>CGTGGACAAGAGCAGGTGGCAGCAGGGGAACGTCTTCTC<br>ATGCTCTGTGATGCATGAGGCTCTGAAATTCCACTACACG<br>CAGAAGAGCCTCTCCCTGTCTCCGGGTAAA | 31 |
| AQP4-Seldeg with MST-HN, knobs-into-holes and arginine mutations | ATGAGTGACAGACCCACAGCAAGGCGGTGGGGTAAGTGT<br>GGACCTTTGTGTACCAGAGAGAACATCATGGTGGCTTTCA<br>AAGGGGTCTGGACTCAAGCTTTCTGGAAAGCAGTCACAG<br>CGGAATTTCTGGCCATGCTTATTTTTGTTCTCCTCAGCCTG<br>GGATCCACCATCAACTGGGGTGGAACAGAAAAGCCTTTA<br>CCGGTCGACATGGTTCTCATCTCCCTTTGCTTTGGACTCA<br>GCATTGCAACCATGGTGCAGTGCTTTGGCCATATCAGCGG<br>TGGCCACATCAACCCTGCAGTGACTGTGGCCATGGTGTGC<br>ACCAGGAAGATCAGCATCGCCAAGTCTGTCTTCTACATCG<br>CAGCCCAGTGCCTGGGGGCCATCATTGGAGCAGGAATCC | 33 |

TABLE 1-continued

DNA sequences of polynucleotides encoding exemplary proteins.

| Polynucleotide encoding protein | DNA sequence | SEQ ID NO: |
|---|---|---|
| | TCTATCTGGTCACACCTCCCAGTGTGGTGGGAGGCCTGGG<br>AGTCACCATGGTTCATGGAAATCTTACCGCTGGTCATGGT<br>CTCCTGGTTGAGTTGATAATCACATTTCAATTGGTGTTTA<br>CTATCTTTGCCAGCTGTGATTCCAAACGGACTGATGTCAC<br>TGGCTCAATAGCTTTAGCAATTGGATTTTCTGTTGCAATT<br>GGACATTTATTTGCAATCAATTATACTGGTGCCAGCATGA<br>ATCCCGCCCGATCCTTTGGACCTGCAGTTATCATGGGAAA<br>TTGGGAAAACCATTGGATATATTGGGTTGGGCCCATCATA<br>GGAGCTGTCCTCGCTGGTGGCCTTTATGAGTATGTCTTCT<br>GTCCAGATGTTGAATTCAAACGTCGTTTTAAAGAAGCCTT<br>CAGCAAAGCTGCCCAGCAAACAAAAGGAAGCTACATGG<br>AGGTGGAGGACAACAGGAGTCAGGTAGAGACGGATGAC<br>CTGATTCTAAAACCTGGAGTGGTGCATGTGATTGACGTTG<br>ACCGGGGAGAGGAGAAGAAGGGGAAAGACCAATCTGGA<br>GAGGTATTGTCTTCAGTAGGAGGCGGTGGATCAGTTGAG<br>CCCAAATCTTCTGACAAAACTCACACATGCCCACCGTGCC<br>CAGCACCTGAACTCCTGAGGGGACCGTCAGTCTTCCTCTT<br>CCCCCCAAAACCCAAGGACACCCTCTACATCACTCGGGA<br>ACCTGAGGTCACATGCGTGGTGGTGGACGTGAGCCACGA<br>AGACCCTGAGGTCAAGTTCAACTGGTACGTGGACGGCGT<br>GGAGGTGCATAATGCCAAGACAAAGCCGCGGGAGGAGC<br>AGTACAACAGCACGTACCGTGTGGTCAGCGTCCTCACCG<br>TCCTGCACCAGGACTGGCTGAATGGCAAGGAGTACAAGT<br>GCAAGGTCTCCAACAAAGCCCGCCCAGCCCCCATCGAGA<br>AAACCATCTCCAAAGCCAAAGGGCAGCCCCGAGAACCAC<br>AGGTGACCACCCTGCCCCCATCCCGGGATGAGCTGACCA<br>AGAACCAGGTCAGCCTGACCTGCCTGGTCAAAGGCTTCT<br>ATCCCAGCGACATCGCCGTGGAGTGGGAGAGCAATGGGC<br>AGCCGGAGAACAACTACAAGACCTTCCCTCCCGTGCTGG<br>ACTCCGACGGCTCCTTCTTCCTCTACAGCAAGCTCACCGT<br>GGACAAGAGCAGGTGGCAGCAGGGGAACGTCTTCTCATG<br>CTCTGTGATGCATGAGGCTCTGAAATTCCACTACACGCAG<br>AAGAGCCTCTCCCTGTCTCCGGGTAAA | |

TABLE 2

Amino acid sequences of exemplary proteins.

| Protein | Amino acid sequence | SEQ ID NO: |
|---|---|---|
| MOG-Seldeg with MST-HN, knobs-into-holes and arginine mutations | GQFRVIGPGYPIRALVGDEAELPCRISPGKNATGMEVGWYRS<br>PFSRVVHLYRNGKDQDAEQAPEYRGRTELLKETISEGKVTLRI<br>QNVRFSDEGGYTCFFRDHSYQEEAAMELKVEDGGGGSVEPK<br>SSDKTHTCPPCPAPELLRGPSVFLFPPKPKDTLYITREPEVTCV<br>VVDVSHEDPEVKFNWYVDGVEVHNAKTKPREEQYNSTYRV<br>VSVLTVLHQDWLNGKEYKCKVSNKARPAPIEKTISKAKGQPR<br>EPQVTTLPPSRDELTKNQVSLTCLVKGFYPSDIAVEWESNGQP<br>ENNYKTFPPVLDSDGSFFLYSKLTVDKSRWQQGNVFSCSVMH<br>EALKFHYTQKSLSLSPGK | 2 |
| HER2-Seldeg with MST-HN, knobs-into-holes and arginine mutations | TQVCTGTDMKLRLPASPETHLDMLRHLYQGCQVVQGNLELT<br>YLPTNASLSFLQDIQEVQGYVLIAHNQVRQVPLQRLRIVRGTQ<br>LFEDNYALAVLDNGDPLNNTTPVTGASPGGLRELQLRSLTEIL<br>KGGVLIQRNPQLCYQDTILWKDIFHKNNQLALTLIDTNRSRAC<br>HPCSPMCKGSRCWGESSEDCQSLTRTVCAGGCARCKGPLPTD<br>CCHEQCAAGCTGPKHSDCLACLHFNHSGICELHCPALVTYNT<br>DTFESMPNPEGRYTFGASCVTACPYNYLSTDVGSCTLVCPLH<br>NQEVTAEDGTQRCEKCSKPCARVCYGLGMEHLREVRAVTSA<br>NIQEFAGCKKIFGSLAFLPESFDGDPASNTAPLQPEQLQVFETL<br>EEITGYLYISAWPDSLPDLSVFQNLQVIRGRILHNGAYSLTLQG<br>LGISWLGLRSLRELGSGLALIHHNTHLCFVHTVPWDQLFRNP<br>HQALLHTANRPEDECVGEGLACHQLCARGHCWGPGPTQCVN<br>CSQFLRGQECVEECRVLQGLPREYVNARHCLPCHPECQPQNG<br>SVTCFGPEADQCVACAHYKDPPFCVARCPSGVKPDLSYMPIW<br>KFPDEEGACQPCPINCTHSCVDLDDKGCPAEQRASPLTIEGRM<br>DPKSSDKTHTCPPCPAPELLRGPSVFLFPPKPKDTLYITREPEV<br>TCVVVDVSHEDPEVKFNWYVDGVEVHNAKTKPREEQYNST<br>YRVVSVLTVLHQDWLNGKEYKCKVSNKARPAPIEKTISKAK<br>GQPREPQVTTLPPSRDELTKNQVSLTCLVKGFYPSDIAVEWES<br>NGQPENNYKTFPPVLDSDGSFFLYSKLTVDKSRWQQGNVFSC<br>SVMHEALKFHYTQKSLSLSPGK | 4 |

TABLE 2-continued

Amino acid sequences of exemplary proteins.

| Protein | Amino acid sequence | SEQ ID NO: |
|---|---|---|
| Fc with MST-HN, knobs-into-holes and arginine mutations | VEPKSSDKTHTCPPCPAPELLRGPSVFLFPPKPKDTLYITREPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALKFHYTQKSLSLSPGK | 6 |
| MOG-Seldeg-PS with knobs-into-holes and arginine mutations | GQFRVIGPGYPIRALVGDEAELPCRISPGKNATGMEVGWYRS PFSRVVHLYRNGKDQDAEQAPEYRGRTELLKETISEGKVTLRI QNVRFSDEGGYTCFFRDHSYQEEAAMELKVEDGGGGSVEPK SSDKTHTCPPCPAPELLRGPSVFLFPPKPKDTLMISRTPEVTCV VVDVSHEDPEVKFNWYVDGVEVHNAKTKPREEQYNSTYRV VSVLTVLHQDWLNGKEYKCKVSNKARPAPIEKTISKAKGQPR EPQVTTLPPSRDELTKNQVSLTCLVKGFYPSDIAVEWESNGQP ENNYKTFPPVLDSDGSFFLYSKLTVDKSRWQQGNVFSCSVMH EALHNHYTQKSLSLSPGKGGGGSEKLGKLQYSLDYDFQNNQ LLVGIIQAAELPALDMGGTSDPYVKVFLLPDKKKKFETKVHR KTLNPVFNEQFTFKVPYSELGGKTLVMAVYDFDRFSKHDIIGE FKVPMNTVDFGHVTEEWRDLQSA | 8 |
| Fc-Sytl with knobs-into-holes and arginine mutations | VEPKSSDKTHTCPPCPAPELLRGPSVFLFPPKPKDTLMISRTPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALHNHYTQKSLSLSPGKGGGGSEKLGKLQYSLDYD FQNNQLLVGIIQAAELPALDMGGTSDPYVKVFLLPDKKKKFE TKVHRKTLNPVFNEQFTFKVPYSELGGKTLVMAVYDFDRFSK HDIIGEFKVPMNTVDFGHVTEEWRDLQSA | 10 |
| MOG-Seldeg-PS with knobs-into-holes, electrostatic steering and arginine mutations | GQFRVIGPGYPIRALVGDEAELPCRISPGKNATGMEVGWYRS PFSRVVHLYRNGKDQDAEQAPEYRGRTELLKETISEGKVTLRI QNVRFSDEGGYTCFFRDHSYQEEAAMELKVEDGGGGSVEPK SSDKTHTCPPCPAPELLRGPSVFLFPPKPKDTLMISRTPEVTCV VVDVSHEDPEVKFNWYVDGVEVHNAKTKPREEQYNSTYRV VSVLTVLHQDWLNGKEYKCKVSNKARPAPIEKTISKAKGQPR EPQVTTLPPSRDELTKNQVSLTCLVKGFYPSDIAVEWESNGQP ENNYDTFPPVLDSDGSFFLYSDLTVDKSRWQQGNVFSCSVMH EALHNHYTQKSLSLSPGKGGGGSEKLGKLQYSLDYDFQNNQ LLVGIIQAAELPALDMGGTSDPYVKVFLLPDKKKKFETKVHR KTLNPVFNEQFTFKVPYSELGGKTLVMAVYDFDRFSKHDIIGE FKVPMNTVDFGHVTEEWRDLQSA | 12 |
| Fc-Sytl with knobs-into-holes, electrostatic steering and arginine mutations | VEPKSSDKTHTCPPCPAPELLRGPSVFLFPPKPKDTLMISRTPE VTCVVVDVSHEDPEVKFNWYVDGVEVHNAKTKPREEQYNS TYRVVSVLTVLHQDWLNGKEYKCKVSNKARPAPIEKTISKAK GQPREPQVYTLPPSRDKLTKNQVHLTCLVKGFYPSDIAVEWE SNGQPENNYKTTPPVLKSDGSFALYSKLTVDKSRWQQGNVFS CSVMHEALHNHYTQKSLSLSPGKGGGGSEKLGKLQYSLDYD FQNNQLLVGIIQAAELPALDMGGTSDPYVKVFLLPDKKKKFE TKVHRKTLNPVFNEQFTFKVPYSELGGKTLVMAVYDFDRFSK HDIIGEFKVPMNTVDFGHVTEEWRDLQSA | 14 |
| MOG-Seldeg-TfR with knobs-into-holes mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI SKAKGQPREPQVTTLPPSRDELTKNQVSLTCLVKGFYPSDIAV EWESNGQPENNYKTFPPVLDSDGSFFLYSKLTVDKSRWQQG NVFSCSVMHEALHNHYTQKSLSLSPGKGGGGSGQFRVIGPGY PIRALVGDEAELPCRISPGKNATGMEVGWYRSPFSRVVHLYR NGKDQDAEQAPEYRGRTELLKETISEGKVTLRIQNVRFSDEG GYTCFFRDHSYQEEAAMELKVED | 16 |
| TfR Ab with knobs-into-holes mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVDVSHEDPEVKFNWYVDGVEVHNAKTKPREE QYNSTYRVVSVLTVLHQDWLNGKEYKCKVSNKALPAPIEKTI | 18 |

TABLE 2-continued

| Amino acid sequences of exemplary proteins. | | |
|---|---|---|
| Protein | Amino acid sequence | SEQ ID NO: |
| | SKAKGQPREPQVYTLPPSRDELTKNQVHLTCLVKGFYPSDIA VEWESNGQPENNYKTTPPVLDSDGSFALYSKLTVDKSRWQQ GNVFSCSVMHEALHNHYTQKSLSLSPGK | |
| TfR Ab LC | DIQMTQSPSSLSASVGDRVTITCRASDNLYSNLAWYQQKPGK SPKLLVYDATNLADGVPSRFSGSGSGTDYTLTISSLQPEDFAT YYCQHFWGTPLTFGQGTKVEIKTVAAPSVFIFPPSDEQLKSGT ASVVCLLNNFYPREAKVQWKVDNALQSGNSQESVTEQDSKD STYSLSSTLTLSKADYEKHKVYACEVTHQGLSSPVTKSFNRGEC | 20 |
| MOG-Seldeg-TfR with knobs-into-holes and arginine mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLRGPSVFLFPPKPKDTLMI SRTPEVTCVVVDVSHEDPEVKFNWYVDGVEVHNAKTKPREE QYNSTYRVVSVLTVLHQDWLNGKEYKCKVSNKARPAPIEKTI SKAKGQPREPQVTTLPPSRDELTKNQVSLTCLVKGFYPSDIAV EWESNGQPENNYKTFPPVLDSDGSFFLYSKLTVDKSRWQQG NVFSCSVMHEALHNHYTQKSLSLSPGKGGGGSGQFRVIGPGY PIRALVGDEAELPCRISPGKNATGMEVGWYRSPFSRVVHLYR NGKDQDAEQAPEYRGRTELLKETISEGKVTLRIQNVRFSDEG GYTCFFRDHSYQEEAAMELKVED | 22 |
| TfR Ab with knobs-into-holes and arginine mutations | EVQLVQSGAEVKKPGASVKVSCKASGYTFTSYWMHWVRQA PGQRLEWIGEINPTNGRTNYIEKFKSRATLTVDKSASTAYMEL SSLRSEDTAVYYCARGTRAYHYWGQGTMVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLRGPSVFLFPPKPKDTLMI SRTPEVTCVVVDVSHEDPEVKFNWYVDGVEVHNAKTKPREE QYNSTYRVVSVLTVLHQDWLNGKEYKCKVSNKARPAPIEKTI SKAKGQPREPQVYTLPPSRDELTKNQVHLTCLVKGFYPSDIA VEWESNGQPENNYKTTPPVLDSDGSFALYSKLTVDKSRWQQ GNVFSCSVMHEALHNHYTQKSLSLSPGK | 24 |
| HER2-ECD-Fc with MST-HN and knobs-into-holes | TQVCTGTDMKLRLPASPETHLDMLRHLYQGCQVVQGNLELT YLPTNASLSFLQDIQEVQGYVLIAHNQVRQVPLQRLRIVRGTQ LFEDNYALAVLDNGDPLNNTTPVTGASPGGLRELQLRSLTEIL KGGVLIQRNPQLCYQDTILWKDIFHKNNQLALTLIDTNRSRAC HPCSPMCKGSRCWGESSEDCQSLTRTVCAGGCARCKGPLPTD CCHEQCAAGCTGPKHSDCLACLHFNHSGICELHCPALVTYNT DTFESMPNPEGRYTFGASCVTACPYNYLSTDVGSCTLVCPLH NQEVTAEDGTQRCEKCSKPCARVCYGLGMEHLREVRAVTSA NIQEFAGCKKIFGSLAFLPESFDGDPASNTAPLQPEQLQVFETL EEITGYLYISAWPDSLPDLSVFQNLQVIRGRILHNGAYSLTLQG LGISWLGLRSLRELGSGLALIHHNTHLCFVHTVPWDQLFRNP HQALLHTANRPEDECVGEGLACHQLCARGHCWGPGPTQCVN CSQFLRGQECVEECRVLQGLPREYVNARHCLPCHPECQPQNG SVTCFGPEADQCVACAHYKDPPFCVARCPSGVKPDLSYMPIW KFPDEEGACQPCPINCTHSCVDLDDKGCPAEQRASPLTIEGRM DPKSSDKTHTCPPCPAPELLGGPSVFLFPPKPKDTLYITREPEV TCVVVDVSHEDPEVKFNWYVDGVEVHNAKTKPREEQYNST YRVVSVLTVLHQDWLNGKEYKCKVSNKALPAPIEKTISKAKG QPREPQVTTLPPSRDELTKNQVSLTCLVKGFYPSDIAVEWESN GQPENNYKTFPPVLDSDGSFFLYSKLTVDKSRWQQGNVFSCS VMHEALKFHYTQKSLSLSPGK | 26 |
| Fc with MST-HN and knobs-into-holes mutations | VEPKSSDKTHTCPPCPAPELLGGPSVFLFPPKPKDTLYITREPE VTCVVVDVSHEDPEVKFNWYVDGVEVHNAKTKPREEQYNS TYRVVSVLTVLHQDWLNGKEYKCKVSNKALPAPIEKTISKAK GQPREPQVYTLPPSRDELTKNQVHLTCLVKGFYPSDIAVEWE SNGQPENNYKTTPPVLDSDGSFALYSKLTVDKSRWQQGNVFS CSVMHEALKFHYTQKSLSLSPGK | 28 |
| PSMA-Seldeg with MST-HN, knobs-into-holes and arginine mutations | VEPKSSDKTHTCPPCPAPELLRGPSVFLFPPKPKDTLYITREPE VTCVVVDVSHEDPEVKFNWYVDGVEVHNAKTKPREEQYNS TYRVVSVLTVLHQDWLNGKEYKCKVSNKARPAPIEKTISKAK GQPREPQVTTLPPSRDELTKNQVSLTCLVKGFYPSDIAVEWES NGQPENNYKTFPPVLDSDGSFFLYSKLTVDKSRWQQGNVFSC SVMHEALKFHYTQKSLSLSPGKGGGGSKSSNEATNITPKHNM KAFLDELKAENIKKFLYNFTQIPHLAGTEQNFQLAKQIQSQW KEFGLDSVELAHYDVLLSYPNKTHPNYISIINEDGNEIFNTSLF EPPPPGYENVSDIVPPFSAFSPQGMPEGDLVYVNYARTEDFFK LERDMKINCSGKIVIARYGKVFRGNKVKNAQLAGAKGVILYS | 30 |

TABLE 2-continued

Amino acid sequences of exemplary proteins.

| Protein | Amino acid sequence | SEQ ID NO: |
|---|---|---|
| | DPADYFAPGVKSYPDGWNLPGGGVQRGNILNLNGAGDPLTP<br>GYPANEYAYRRGIAEAVGLPSIPVHPIGYYDAQKLLEKMGGS<br>APPDSSWRGSLKVPYNVGPGFTGNFSTQKVKMHIHSTNEVTR<br>IYNVIGTLRGAVEPDRYVILGGHRDSWVFGGIDPQSGAAVVH<br>EIVRSFGTLKKEGWRPRRTILFASWDAEEFGLLGSTEWAEENS<br>RLLQERGVAYINADSSIEGNYTLRVDCTPLMYSLVHNLTKEL<br>KSPDEGFEGKSLYESWTKKSPSPEFSGMPRISKLGSGNDFEVF<br>FQRLGIASGRARYTKNWETNKFSGYPLYHSVYETYELVEKFY<br>DPMFKYHLTVAQVRGGMVFELANSIVLPFDCRDYAVVLRKY<br>ADKIYSISMKHPQEMKTYSVSFDSLFSAVKNFTEIASKFSERLQ<br>DFDKSNPIVLRMMNDQLMFLERAFIDPLGLPDRPFYRHVIYAP<br>SSHNKYAGESFPGIYDALFDIESKVDPSKAWGEVKRQIYVAAF<br>TVQAAAETLSEVA | |
| GAD65-Seldeg with MST-HN, knobs-into-holes and arginine mutations | MASPGSGFWSFGSEDGSGDSENPGTARAWCQVAQKFTGGIG<br>NKLCALLYGDAEKPAESGGSQPPRAAARKAACACDQKPCSC<br>SKVDVNYAFLHATDLLPACDGERPTLAFLQDVMNILLQYVV<br>KSFDRSTKVIDFHYPNELLQEYNWELADQPQNLEEILMHCQT<br>TLKYAIKTGHPRYFNQLSTGLDMVGLAADWLTSTANTNMFT<br>YEIAPVFVLLEYVTLKKMREIIGWPGGSGDGIFSPGGAISNMY<br>AMMIARFKMFPEVKEKGMAALPRLIAFTSEHSHFSLKKGAAA<br>LGIGTDSVILIKCDERGKMIPSDLERRILEAKQKGFVPFLVSAT<br>AGTTVYGAFDPLLAVADICKKYKIWMHVDAAWGGGLLMSR<br>KHKWKLSGVERANSVTWNPHKMMGVPLQCSALLVREEGLM<br>QNCNQMHASYLFQQDKHYDLSYDTGDKALQCGRHVDVFKL<br>WLMWRAKGTTGFEAHVDKCLELAEYLYNIIKNREGYEMVFD<br>GKPQHTNVCFWYIPPSLRTLEDNEERMSRLSKVAPVIKARMM<br>EYGTTMVSYQPLGDKVNFFRMVISNPAATHQDIDFLIEEIERL<br>GQDLGGGGSVEPKSSDKTHTCPPCPAPELLRGPSVFLFPPKPK<br>DTLYITREPEVTCVVVDVSHEDPEVKFNWYVDGVEVHNAKT<br>KPREEQYNSTYRVVSVLTVLHQDWLNGKEYKCKVSNKARPA<br>PIEKTISKAKGQPREPQVTTLPPSRDELTKNQVSLTCLVKGFYP<br>SDIAVEWESNGQPENNYKTFPPVLDSDGSFFLYSKLTVDKSR<br>WQQGNVFSCSVMHEALKFHYTQKSLSLSPGK | 32 |
| AQP4-Seldeg with MST-HN, knobs-into-holes and arginine mutations | MSDRPTARRWGKCGPLCTRENIMVAFKGVWTQAFWKAVTA<br>EFLAMLIFVLLSLGSTINWGGTEKPLPVDMVLISLCFGLSIATM<br>VQCFGHISGGHINPAVTVAMVCTRKISIAKSVFYIAAQCLGAII<br>GAGILYLVTPPSVVGGLGVTMVHGNLTAGHGLLVELIITFQLV<br>FTIFASCDSKRTDVTGSIALAIGFSVAIGHLFAINYTGASMNPA<br>RSFGPAVIMGNWENHWIYWVGPIIGAVLAGGLYEYVFCPDVE<br>FKRRFKEAFSKAAQQTKGSYMEVEDNRSQVETDDLILKPGVV<br>HVIDVDRGEEKKGKDQSGEVLSSVGGGGSVEPKSSDKTHTCP<br>PCPAPELLRGPSVFLFPPKPKDTLYITREPEVTCVVVDVSHEDP<br>EVKFNWYVDGVEVHNAKTKPREEQYNSTYRVVSVLTVLHQ<br>DWLNGKEYKCKVSNKARPAPIEKTISKAKGQPREPQVTTLPPS<br>RDELTKNQVSLTCLVKGFYPSDIAVEWESNGQPENNYKTFPP<br>VLDSDGSFFLYSKLTVDKSRWQQGNVFSCSVMHEALKFHYT<br>QKSLSLSPGK | 34 |

The DNA sequence of SEQ ID NO:1 is of a polynucleotide encoding an exemplary MOG-Seldeg fusion protein (SEQ ID NO:2) having mutations to increase FcRn binding, knobs-into-holes mutations and arginine mutations. The exemplary DNA and amino acid sequences of the MOG respectively of SEQ ID NO: 1 and 2 are of mouse origin.

In particular, the amino acid sequence of the exemplary MOG-Seldeg of SEQ TD NO: 2 forms a fusion protein having, in order from N- to C-terminus, residues 1-117 of mouse (in) MOG, a first linker at residues 118-122, an immunoglobulin hinge (human IgG1-derived) at residues 123-138, an immunoglobulin CH2 domain (human IgG1-derived) at residues 139-248, an immunoglobulin CH3 domain (human IgG1-derived) at residues 249-355. The exemplary MOG-Seldeg of SEQ ID NO:2 has mutations that increase FcRn binding at residues 160, 162, 164, 341 and 342, arginine mutations at residues 144 and 236, and ‘knobs-into-holes’ mutations at residues 257 and 302. The cysteine residue (128) that usually pairs with an immunoglobulin light chain is mutated to serine. The amino acid residue numbers referred to in SEQ ID NO:2 are those of the protein sequence, and do not refer to the EU numbering convention.

The DNA sequence of SEQ ID NO:3 is of a polynucleotide encoding an exemplary HER2-Seldeg fusion protein (SEQ ID NO:4) having mutations to increase FcRn binding, knobs-into-holes mutations and arginine mutations.

In particular, the amino acid sequence of the exemplary HER2-Seldeg of SEQ ID NO: 4 forms a fusion protein having, in order from N- to C-terminus, residues 1-630 of HER2, a first linker at residues 631-636, an immunoglobulin hinge (human IgG1-derived) at residues 637-650, an immunoglobulin CH2 domain (human IgG1-derived) at residues 651-760, an immunoglobulin CH3 domain (human IgG1-derived) at residues 761-867. The exemplary HER2-Seldeg of SEQ ID NO:4 has mutations that increase FcRn binding at residues 672, 674, 676, 853 and 854, arginine mutations at residues 656 and 748, and ‘knobs-into-holes’ mutations at residues 769 and 814. The cysteine residue (640) that usually pairs with an immunoglobulin light chain is mutated to serine. The amino acid residue numbers referred to in SEQ ID NO:4 are those of the protein sequence, and do not refer to the EU numbering convention.

The DNA sequence of SEQ ID NO:5 is of a polynucleotide encoding an exemplary Fc fragment (SEQ ID NO:6), having mutations to increase FcRn binding, knobs-into-holes mutations and arginine mutations. The fusion protein of SEQ ID NO:6 is configured, for example, for heterodimer formation with the MOG-Seldeg (SEQ ID NO:2) or HER2-Seldeg (SEQ ID NO:4) fusion.

In particular, the amino acid sequence of the exemplary Fc fragment of SEQ ID NO: 6 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The exemplary Fc fragment of SEQ ID NO:6 has mutations that increase FcRn binding at residues 38, 40, 42, 219 and 220, arginine mutations at residues 22 and 114, and 'knobs-into-holes' mutations at residues 150 and 191. The cysteine residue (6) that usually pairs with an immunoglobulin light chain is mutated to serine. The amino acid residue numbers referred to in SEQ ID NO:6 are those of the protein sequence, and do not refer to the EU numbering convention.

The DNA sequence of SEQ ID NO:7 is of a polynucleotide encoding an exemplary MOG-Seldeg-PS fusion having knobs-into-holes mutations and arginine mutations, and the corresponding amino acid sequence of the encoded fusion protein is SEQ ID NO:8.

In particular, the amino acid sequence of the exemplary MOG-Seldeg-PS fusion of SEQ ID NO: 8 has, in order from N- to C-terminus, residues 1-117 of mMOG, a first linker at residues 118-122, an immunoglobulin hinge (human IgG1-derived) at residues 123-138, an immunoglobulin CH2 domain (human IgG1-derived) at residues 139-248, an immunoglobulin CH3 domain (human IgG1-derived) at residues 249-355. The exemplary MOG-Seldeg-PS of SEQ ID NO: 8 has arginine mutations at residues 144 and 236, and 'knobs-into-holes' mutations at residues 257 and 302. The cysteine residue (128) that pairs with an immunoglobulin light chain is mutated to serine. Residues 141-266 of the C2A PS-binding domain of synaptotagmin (Syt1) (shown as residues 361-486) are fused to the C-terminus of the CH3 domain via a GGGGS linker peptide (residues 356-360). The amino acid residue numbers referred to in SEQ ID NO:8 are those of the protein sequence, and do not refer to the EU numbering convention.

The DNA sequence of SEQ ID NO:9 is of a polynucleotide encoding an exemplary Fc-Syt1 fusion (SEQ ID NO:10) having knobs-into-holes mutations and arginine mutations, configured for heterodimer formation, for example, with the MOG-Seldeg-PS (SEQ ID NO: 8).

In particular, the amino acid sequence of the exemplary Fc-Syt1 fusion of SEQ ID NO: 10 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 126-233. The exemplary Fc-Syt1 fusion protein of SEQ ID NO:10 has arginine mutations at residues 22 and 114 and 'knobs-into-holes' mutations at residues 150 and 191. The cysteine residue (6) that usually pairs with an immunoglobulin light chain is mutated to serine. Residues 141-266 of the C2A PS-binding domain of synaptotagmin (Syt1) (shown as residues 239-364) are fused to the C-terminus of the CH3 domain via a GGGGS linker peptide (residues 234-238). The amino acid residue numbers referred to in SEQ ID NO:10 are those of the protein sequence, and do not refer to the EU numbering convention.

The DNA sequence of SEQ ID NO:11 is of a polynucleotide encoding an exemplary MOG-Seldeg-PS fusion (SEQ ID NO:12) having knobs-into-holes mutations, electrostatic steering mutations and arginine mutations.

In particular, the amino acid sequence of the exemplary MOG-Seldeg-PS fusion of SEQ ID NO: 12 has, in order from N- to C-terminus, residues 1-117 of mMOG, a first linker at residues 118-122, an immunoglobulin hinge (human IgG1-derived) at residues 123-138, an immunoglobulin CH2 domain (human IgG1-derived) at residues 139-248, an immunoglobulin CH3 domain (human IgG1-derived) at residues 249-355. The exemplary MOG-Seldeg-PS of SEQ ID NO: 12 has arginine mutations at residues 144 and 236, electrostatic steering mutations at residues 300 and 317 and 'knobs-into-holes' mutations at residues 257 and 302. The cysteine residue (128) that pairs with an immunoglobulin light chain is mutated to serine. Residues 141-266 of the C2A PS-binding domain of synaptotagmin (Syt1) (shown as residues 361-486) are fused to the C-terminus of the CH3 domain via a GGGS linker peptide (residues 356-360). The amino acid residue numbers referred to in SEQ ID NO:12 are those of the protein sequence, and do not refer to the EU numbering convention.

The DNA sequence of SEQ ID NO:13 is of a polynucleotide encoding an exemplary Fc-Syt1 fusion (SEQ ID NO:14) having knobs-into-holes mutations, electrostatic steering mutations and arginine mutations, configured, for example, for heterodimer formation with the MOG-Seldeg-PS (SEQ ID NO:12).

In particular, the amino acid sequence of the exemplary Fc-Syt1 fusion protein of SEQ ID NO: 14 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The exemplary MOG-Seldeg-PS of SQ ID NO:14 has arginine mutations at residues 22 and 114, electrostatic steering mutations at residues 143 and 185 and 'knobs-into-holes' mutations at residues 150 and 191. The cysteine residue (6) that pairs with an immunoglobulin light chain is mutated to serine. Residues 141-266 of the C2A PS-binding domain of synaptotagmin (Syt1) (shown in residues 239-364) are fused to the C-terminus of the CH3 domain via a GGGGS linker peptide (residues 234-238). The amino acid residue numbers referred to in SEQ ID NO:14 are those of the protein sequence, and do not refer to the EU numbering convention.

The DNA sequence of SEQ ID NO:15 is of a polynucleotide encoding an exemplary MOG-Seldeg-TfR fusion protein (SEQ ID NO:16) comprising a TfR-specific antibody heavy chain with knobs into holes mutations.

In particular, the amino acid sequence of the exemplary TfR-specific antibody heavy chain-MOG fusion (MOG-Seldeg-TfR) of SEQ ID NO: 16 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229, an immunoglobulin CH2 domain (human IgG1-derived) at residues 230-337, an immunoglobulin CH3 domain (human IgG1-derived) at residues 237-446. The exemplary TfR-specific antibody heavy chain of SEQ ID NO:16 has 'knobs-into-holes' mutations at residues 348 and 393. Residues 1-117 of mMOG (shown as residues 452-568) are fused to the C-terminus of the CH3 domain via a GGGGS linker peptide (residues 447-451). The amino acid residue numbers referred to in SEQ ID NO:16 are those of the protein sequence, and do not refer to the EU numbering convention.

The DNA sequence of SEQ ID NO:17 is of a polynucleotide encoding an exemplary TfR-specific antibody heavy chain. The encoded fusion protein (SEQ ID NO:18) having knobs into holes mutations is configured, for example, for heterodimer formation with the MOG-Seldeg-TfR fusion (SEQ ID NO:16).

In particular, the amino acid sequence of the exemplary TfR-specific antibody heavy chain of SEQ ID NO: 18 for heterodimer formation with the TfR-specific heavy chain-MOG fusion (SEQ ID NO: 16) has, in order from N- to C-terminus, of a TfR-specific VH domain at residues 1-116, an immunoglobulin CH1 domain (human IgG1-derived) at residues 117-213, an immunoglobulin hinge (human IgG1-derived) at residues 214-229 an immunoglobulin CH2 domain (human IgG1-derived) at residues 230-339, an immunoglobulin CH3 domain (human IgG1-derived) at residues 340-446. The exemplary TfR-specific antibody heavy chain of SEQ ID NO: 18 has 'knobs-into-holes' mutations at residues 363 and 404. The amino acid residue numbers referred to in SEQ ID NO:18 are those of the protein sequence, and do not refer to the EU numbering convention.

The DNA sequence of SEQ ID NO:19 is of a polynucleotide encoding an exemplary light chain of a TfR-specific antibody (SEQ ID NO:20) and is configured, for example, for heterodimer formation with the MOG-Seldeg-TfR fusion (SEQ ID NO:16) and TfR-specific antibody heavy chain (SEQ ID NO:18).

In particular, the amino acid sequence of the exemplary TfR-specific antibody light chain of SEQ ID NO: 20 has, in order from N- to C-terminus a TfR-specific VL domain at residues 1-107, and an immunoglobulin CL domain (human Cκ) at residues 108-213. The amino acid residue numbers referred to in SEQ ID NO:20 are those of the protein sequence, and do not refer to the EU numbering convention.

The DNA sequence of SEQ ID NO: 21 is of a polynucleotide encoding an exemplary MOG-Seldeg-TfR fusion protein (SEQ ID NO: 22) having a TfR-specific antibody heavy chain with arginine mutations, and knobs-into-holes mutations.

In particular, the amino acid sequence of the exemplary TfR-specific antibody heavy chain-MOG fusion (MOG-Seldeg-TfR) of SEQ ID NO: 22 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229, an immunoglobulin CH2 domain (human IgG1-derived) at residues 230-339, an immunoglobulin CH3 domain (human IgG1-derived) at residues 340-446. The exemplary TfR-specific antibody heavy chain of SEQ ID NO: 22 has arginine mutations at residues 235 and 327, and 'knobs-into-holes' mutations at residues 348 and 393. Residues 1-117 of mMOG (shown as residues 452-568) are fused to the C-terminus of the CH3 domain via a GGGGS linker peptide (residues 447-451). The amino acid residue numbers referred to in SEQ ID NO:22 are those of the protein sequence, and do not refer to the EU numbering convention.

The DNA sequence of SEQ ID NO: 23 is of a polynucleotide encoding an exemplary TfR-specific antibody heavy chain (SEQ ID NO: 24) having arginine mutations, and knobs-into-holes mutations, and is configured, for example, for heterodimer formation with the MOG-Seldeg-TfR fusion (SEQ ID NO: 22).

In particular, the amino acid sequence of the exemplary TfR-specific antibody heavy chain of SEQ ID NO: 24 has, in order from N- to C-terminus, a TfR-specific VH domain at residues 1-116, an immunoglobulin CH1 domain (human IgG1-derived) at residues 117-213, an immunoglobulin hinge (human IgG1-derived) at residues 214-229 an immunoglobulin CH2 domain (human IgG1-derived) at residues 230-339, an immunoglobulin CH3 domain (human IgG1-derived) at residues 340-446. The TfR-specific antibody heavy chain of SEQ ID NO:24 has arginine mutations at residues 235 and 327, and 'knobs-into-holes' mutations at residues 363 and 404.). The amino acid residue numbers referred to in SEQ ID NO:24 are those of the protein sequence, and do not refer to the EU numbering convention.

The DNA sequence of SEQ ID NO: 25 is of a polynucleotide encoding an exemplary HER2-Seldeg fusion protein (SEQ ID NO: 26) having mutations to increase FcRn binding, and knobs-into-holes mutations.

In particular, the amino acid sequence of the exemplary variant HER2-Seldeg of SEQ ID NO: 26 forms a fusion protein having, in order from N- to C-terminus, residues 1-630 of HER2, a first linker at residues 631-636, an immunoglobulin hinge (human IgG1-derived) at residues 637-650, an immunoglobulin CH2 domain (human IgG1-derived) at residues 651-760, an immunoglobulin CH3 domain (human IgG1-derived) at residues 761-867. The HER2-Seldeg of SEQ ID NO: 26 has mutations that increase FcRn binding at residues 672, 674, 676, 853 and 854, and 'knobs-into-holes' mutations at residues 769 and 814. The cysteine residue (640) that usually pairs with an immunoglobulin light chain is mutated to serine. The amino acid residue numbers referred to in SEQ ID NO:26 are those of the protein sequence, and do not refer to the EU numbering convention.

The DNA sequence of SEQ ID NO: 27 is of a polynucleotide encoding an exemplary Fc fragment (SEQ ID NO:28) having mutations to increase FcRn binding, and knobs-into-holes mutations, and is configured, for example, for heterodimer formation with the HER2-Seldeg (SEQ ID NO: 26).

In particular, the amino acid sequence of the exemplary variant Fc fragment of SEQ ID NO: 28 has, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233. The variant Fc fragment of SEQ ID NO: 28 has mutations that increase FcRn binding at residues 38, 40, 42, 219 and 220, and 'knobs-into-holes' mutations at residues 150 and 191. The cysteine residue (6) that usually pairs with an immunoglobulin light chain is mutated to serine. The amino acid residue numbers referred to in SEQ ID NO:28 are those of the protein sequence, and do not refer to the EU numbering convention.

The DNA sequence of SEQ ID NO: 29 is of a polynucleotide encoding an exemplary prostate-specific membrane antigen (PSMA)-Seldeg fusion protein (SEQ ID NO: 30) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant PSMA-Seldeg of SEQ ID NO: 30 forms a fusion protein having, in order from N- to C-terminus, an immunoglobulin hinge (human IgG1-derived) at residues 1-16, an immunoglobulin CH2 domain (human IgG1-derived) at residues 17-126, an immunoglobulin CH3 domain (human IgG1-derived) at residues 127-233 fused at the C-terminus via a linker at residues 234-238 to the extracellular domain (residues 239-945) of PSMA. The variant PSMA-Seldeg of SEQ ID NO: 30 has mutations that increase FcRn binding at residues 38, 40, 42, 219 and 220, arginine mutations at residues 22 and 114, and 'knobs-into-holes' mutations at residues 135 and 180. The cysteine residue (6) that usually pairs with an immunoglobulin light chain is mutated to serine. The amino acid residue numbers referred to in SEQ ID NO:30 are those of the protein sequence, and do not refer to the EU numbering convention.

The DNA sequence of SEQ ID NO: 31 is of a polynucleotide encoding an exemplary GAD65-Seldeg fusion protein (SEQ ID NO: 32) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant GAD65-Seldeg of SEQ ID NO: 32 forms a fusion protein having, in order from N- to C-terminus, residues 1-585 of human glutamic acid carboxylase 65 (GAD65), a first linker at residues 586-590, an immunoglobulin hinge (human IgG1-derived) at residues 591-606, an immunoglobulin CH2 domain (human IgG1-derived) at residues 607-716, an immunoglobulin CH3 domain (human IgG1-derived) at residues 717-823. The variant GAD65-Seldeg of SEQ ID NO:32 has mutations that increase FcRn binding at residues 628, 630, 632, 809 and 810, arginine mutations at residues 612 and 704, and 'knobs-into-holes' mutations at residues 725 and 770. The cysteine residue (596) that usually pairs with an immunoglobulin light chain is mutated to serine. The amino acid residue numbers referred to in SEQ ID NO:32 are those of the protein sequence, and do not refer to the EU numbering convention.

The DNA sequence of SEQ ID NO: 33 is of a polynucleotide encoding an exemplary aquaporin 4-Seldeg fusion protein (SEQ ID NO: 34) having mutations to increase FcRn binding, knobs-into-holes mutations and arginine mutations. This fusion protein will form heterodimers, for example, with an exemplary Fc fragment (SEQ ID NO: 6).

In particular, the amino acid sequence of the exemplary variant aquaporin 4 (AQP4)-Seldeg of SEQ ID NO: 34 forms a fusion protein having, in order from N- to C-terminus, residues 1-323 of human aquaporin 4, a first linker at residues 324-328, an immunoglobulin hinge (human IgG1-derived) at residues 329-344, an immunoglobulin CH2 domain (human IgG1-derived) at residues 345-454, an immunoglobulin CH3 domain (human IgG1-derived) at residues 455-561. The variant AQP4-Seldeg of SEQ ID NO:34 has mutations that increase FcRn binding at residues 366, 368, 370, 547,548, arginine mutations at residues 350 and 442, and 'knobs-into-holes' mutations at residues 463 and 508. The cysteine residue (334) that usually pairs with an immunoglobulin light chain is mutated to serine. The amino acid residue numbers referred to in SEQ ID NO:34 are those of the protein sequence, and do not refer to the EU numbering convention.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

As used in this specification and the appended claims, the singular forma "a", "an", and "the" include plural references unless the content clearly dictates otherwise. The term "plurality" includes two or more referents unless the content clearly dictates otherwise.

Unless defined otherwise, all technical and scientific terms used herein have the same meaning as commonly understood by one of ordinary skill in the art to which the disclosure pertains.

SEQUENCE LISTING

```
Sequence total quantity: 38
SEQ ID NO: 1            moltype = DNA  length = 1065
FEATURE                 Location/Qualifiers
source                  1..1065
                        mol_type = genomic DNA
                        organism = Homo sapiens
SEQUENCE: 1
ggacaattca gagtgatagg accagggtat cccatccggg ctttagttgg ggatgaagca   60
gagctgccgt gccgcatctc tcctgggaaa aatgccacgg gcatggaggt gggttggtac  120
cgttctccct tctcaagagt ggttcacctc taccgaaatg gcaaggacca agatgcagag  180
caagcacctg aataccgggg acgcacagag cttctgaaga agactatcag tgagggaaag  240
gttaccctta ggattcagaa cgtgagattc tcagatgaag gaggctacac ctgcttcttc  300
agagaccact cttaccaaga agaggcagca atggagttga aagtggaaga tggaggcggt  360
ggatcagttg agcccaaatc ttctgacaaa actcacacat gcccaccgtg cccagcacct  420
gaactcctga ggggaccgtc agtcttcctc ttccccccaa acccaaggga cacctctac   480
atcactcggg aacctgaggt cacatgcgtg gtggtggacg tgagccacga agaccctgag  540
gtcaagttca actggtacgt ggacggcgtg gaggtgcata atgccaagac aaagccgcgg  600
gaggagcagt acaacagcac gtaccgtgtg gtcagcgtcc tcaccgtcct gcaccaggac  660
tggctgaatg gcaaggagta caagtgcaag gtctccaaca aagcccgccc agccccatc   720
gagaaaacca tctccaaagc caaagggcag ccccgagaac cacaggtgac cacctgccc   780
ccatcccggg atgagctgac caagaaccag gtcagcctga cctgcctggt caaaggcttc  840
tatcccagcg acatcgccgt ggagtgggag agcaatgggc agccggagaa caactacaag  900
accttcctc ccgtgctgga ctccgacggc tccttcttcc tctacagcaa gctcaccgtg  960
gacaagagca ggtggcagca ggggaacgtc ttctcatgct ctgtgatgca tgaggctctg 1020
aaattccact acacgcagaa gagcctctcc ctgtctccgg gtaaa             1065

SEQ ID NO: 2            moltype = AA  length = 355
FEATURE                 Location/Qualifiers
source                  1..355
                        mol_type = protein
```

```
                    organism = Homo sapiens
SEQUENCE: 2
GQFRVIGPGY PIRALVGDEA ELPCRISPGK NATGMEVGWY RSPFSRVVHL YRNGKDQDAE     60
QAPEYRGRTE LLKETISEGK VTLRIQNVRF SDEGGYTCFF RDHSYQEEAA MELKVEDGGG    120
GSVEPKSSDK THTCPPCPAP ELLRGPSVFL FPPKPKDTLY ITREPEVTCV VVDVSHEDPE    180
VKFNWYVDGV EVHNAKTKPR EEQYNSTYRV VSVLTVLHQD WLNGKEYKCK VSNKARPAPI    240
EKTISKAKGQ PREPQVTTLP PSRDELTKNQ VSLTCLVKGF YPSDIAVEWE SNGQPENNYK    300
TFPPVLDSDG SFFLYSKLTV DKSRWQQGNV FSCSVMHEAL KFHYTQKSLS LSPGK         355

SEQ ID NO: 3            moltype = DNA   length = 2601
FEATURE                 Location/Qualifiers
source                  1..2601
                        mol_type = genomic DNA
                        organism = Homo sapiens
SEQUENCE: 3
acccaagtgt gcaccggcac agacatgaag ctgcggctcc ctgccagtcc cgagacccac     60
ctggacatgc tccgccacct ctaccagggc tgccaggtgg tgcagggaaa cctggaactc    120
acctacctgc ccaccaatgc cagcctgtcc ttcctgcagg atatccagga ggtgcagggc    180
tacgtgctca tcgctcacaa ccaagtgagg caggtcccac tgcagaggct gcggattgtg    240
cgaggcaccc agctctttga ggacaactat gccctggccg tgctagacaa tggagacccg    300
ctgaacaata ccacccctgt cacaggggcc tccccaggag gctgcgggga gctgcagctt    360
cgaagcctca cagagatctt gaaaggaggg gtcttgatcc agcggaaccc ccagctctgc    420
taccaggaca cgattttgtg gaaggacatc ttccacaaga caaccagct ggctctcaca     480
ctgatagaca ccaaccgctc tcgggcctc caccccctgtt ctccgatgtg taagggctcc    540
cgctgctggg gagagagttc tgaggattgt cagagcctga cgcgcactgt ctgtgccggt    600
ggctgtgccc gctgcaaggg gccactgccc actgactgct gccatgagca gtgtgctgcc    660
ggctgcacgg gccccaagca ctctgactgc ctggcctgcc tccacttcaa ccacagtggc    720
atctgtgagc tgcactgccc agccctggtc acctacaaca cagacacgtt tgagtccatg    780
cccaatcccg agggccggta cattcggc gccagctgtg tgactgcctg tcctacaac      840
taccttttcta cggacgtggg atcctgcacc ctcgtctgcc ccctgcacaa ccaagaggtg    900
acagcagagg atggaacaca gcggtgtgag aagtgcagca gccctgtgc ccgagtgtgc     960
tatggtctgg gcatggagca cttgcgagag gtgagggcag ttaccagtgc caatatccag   1020
gagtttgctg gctgcaagaa gatctttggg agcctggcat ttctgccgga gctttgat    1080
ggggacccag cctccaacac tgccccgctc cagccagagc agctcaagt gtttgagact   1140
ctggaagaga tcacaggtta cctatacatc tcagcatggc cggacagcct gcctgacctc   1200
agcgtcttcc agaacctgca agtaatccgg ggacgaattc tgcacaatgg cgcctactcg   1260
ctgacccgc aagggctggg catcagctgg ctggggctgc gctcactgag ggaactgggc    1320
agtggactgg ccctcatcca ccataacacc cacctctgct tcgtgcacac ggtgccctgg   1380
gaccgctct ttcggaaccc gcaccaagct ctgctccaca tggccaaccg gcagaggac    1440
gagtgtgtgg gcgagggcct ggcctgccac cagctgtgcg cccgaggcca ctgctgggt   1500
ccagggccca cccagtgtgt caactgcagc cagttccttc ggggcagga gtgcgtggag   1560
gaatgccgag tactgcaggg gctccccagg gagtatgtga atgccaggca ctgtttgccg   1620
tgccacctg agtgtcagcc ccagaatggc tcagtgacct gttttggacc tgaggctgac   1680
cagtctgtgg cctgtgccca ctataaggac cctcccttct gcgtggcccg ctgcccagc   1740
ggtgtgaaac ctgaccctc ctacatgccc atctggaagt ttccagatga ggagggcgca    1800
tgccagcctt gccccatcaa ctgcacccac tcctgtgtgg acctggatga caagggctgc   1860
cccgccgagc agagaggcca ccctctgacg attgaaggcc gcatggacc caaatcttct   1920
gacaaaactc acacatgccc accgtgccca gcacctgaac tcctgagggg accgtcagtc   1980
ttcctcttcc ccccaaaacc caaggacacc ctctacatca ctcgggaacc tgaggtcaca   2040
tgcgtggtgg tggacgtgag ccacgaagac cctgaggtca agttcaactg gtacgtggac   2100
ggcgtggagg tgcataatgc caagacaaaa ccgcggggag gagcagtacaa cagcacgtac   2160
cgtgtggtca gcgtcctcac cgtcctgcac caggactggc tgaatggcaa ggagtacaag   2220
tgcaaggtct ccaacaaagc cgcccagcc ccatcgaga aaaccatctc caaagccaaa     2280
gggcagcccc gagaaccaca ggtgaccacc ctgcccccat cccgggatga gctgaccaag   2340
aaccaggtca gcctgacctg cctggtcaaa ggcttctatc ccagcgacat cgccgtggag   2400
tgggagagca atgggcagcc ggagaacaac tacaagacct cccctcccgt gctggactcc   2460
gacggctcct tcttcctcta cagcaagctc accgtggaca agagcaggtg gcagcagggg   2520
aacgtcttct catgctctgt gatgcatgag gctctgaaat ccactacac gcagaagagc   2580
ctctccctgt ctcctggtaa a                                             2601

SEQ ID NO: 4            moltype = AA   length = 867
FEATURE                 Location/Qualifiers
source                  1..867
                        mol_type = protein
                        organism = Homo sapiens
SEQUENCE: 4
TQVCTGTDMK LRLPASPETH LDMLRHLYQG CQVVQGNLEL TYLPTNASLS FLQDIQEVQG     60
YVLIAHNQVR QVPLQRLRIV RGTQLFEDNY ALAVLDNGDP LNNTTPVTGA SPGGLRELQL    120
RSLTEILKGG VLIQRNPQLC YQDTILWKDI FHKNNQLALT LIDTNRSRAC HPCSPMCKGS    180
RCWGESSEDC QSLTRTVCAG GCARCKGPLP TDCCHEQCAA GCTGPKHSDC LACLHFNHSG    240
ICELHCPALV TYNTDTFESM PNPEGRYTFG ASCVTACPYN YLSTDVGSCT LVCPLHNQEV    300
TAEDGTQRCE KCSKPCARVC YGLGMEHLRE VRAVTSANIQ EFAGCKKIFG SLAFLPESFD    360
GDPASNTAPL QPEQLQVFET LEEITGYLYI SAWPDSLPDL SVFQNLQVIR GRILHNGAYS    420
LTLQGLGISW LGLRSLRELG SGLALIHHNT HLCFVHTVPW DQLFRNPHQA LLHTANRPED    480
ECVGEGLACH QLCARGHCWG PGPTQCVNCS QFLRGQECVE ECRVLQGLPR EYVNARHCLP    540
CHPECQPQNG SVTCFGPEAD QCVACAHYKD PPFCVARCPS GVKPDLSYMP IWKFPDEEGA    600
CQPCPINCTH SCVDLDDKGC PAEQRASPLT IEGRMDPKSS DKTHTCPPCP APELLRGPSV    660
FLFPPKPKDT LYITREPEVT CVVVDVSHED PEVKFNWYVD GVEVHNAKTK PREEQYNSTY    720
RVVSVLTVLH QDWLNGKEYK CKVSNKARPA PIEKTISKAK GQPREPQVTT LPPSRDELTK    780
```

```
NQVSLTCLVK GFYPSDIAVE WESNGQPENN YKTFPPVLDS DGSFFLYSKL TVDKSRWQQG    840
NVFSCSVMHE ALKFHYTQKS LSLSPGK                                        867

SEQ ID NO: 5              moltype = DNA  length = 699
FEATURE                   Location/Qualifiers
source                    1..699
                          mol_type = genomic DNA
                          organism = Homo sapiens
SEQUENCE: 5
gttgagccca aatcttctga caaaactcac acatgcccac cgtgcccagc acctgaactc    60
ctgagggga cgtcagtctt cctcttcccc ccaaaaccca aggacaccct ctacatcact    120
cgggaacctg aggtcacatg cgtggtggtg gacgtgagcc acgaagaccc tgaggtcaag    180
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg caaggtctcc aacaaagccc tcccagcccc catcgagaaa    360
accatctcca agccaaagg gcagccccga gaaccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc gccctctaca gcaagctcac cgtggacaag    600
agcaggtggc agcaggggaa cgtcttctca tgctccgtga tgcatgaggc tctgaaattc    660
cactacacgc agaagagcct ctccctgtct ccgggtaaa                           699

SEQ ID NO: 6              moltype = AA  length = 233
FEATURE                   Location/Qualifiers
source                    1..233
                          mol_type = protein
                          organism = Homo sapiens
SEQUENCE: 6
VEPKSSDKTH TCPPCPAPEL LRGPSVFLFP PKPKDTLYIT REPEVTCVVV DVSHEDPEVK    60
FNWYVDGVEV HNAKTKPREE QYNSTYRVVS VLTVLHQDWL NGKEYKCKVS NKARPAPIEK    120
TISKAKGQPR EPQVYTLPPS RDELTKNQVH LTCLVKGFYP SDIAVEWESN GQPENNYKTT    180
PPVLDSDGSF ALYSKLTVDK SRWQQGNVFS CSVMHEALKF HYTQKSLSLS PGK           233

SEQ ID NO: 7              moltype = DNA  length = 1458
FEATURE                   Location/Qualifiers
source                    1..1458
                          mol_type = genomic DNA
                          organism = Homo sapiens
SEQUENCE: 7
ggacaattca gagtgatagg accagggtat cccatccggg ctttagttgg ggatgaagca    60
gagctgccgt gccgcatctc tcctgggaaa aatgccacgg gcatggaggt gggttggtac    120
cgttctccct tctcaagagt ggttcacctc taccgaaatg gcaaggacca agatgcagag    180
caagcacctg aataccgggg acgcacagag ctttctgaaa agactatcag tgagggaaag    240
gttacccta ggattcagaa cgtgagattc tcagatgaag gaggctacac ctgcttcttc    300
agagaccact cttaccaaga agaggcagca atggagttga agtgaagga tggaggcggt    360
ggatcagttg agcccaaatc ttctgacaaa actcacacat gcccaccgtg cccagccct    420
gaactcctga ggggaccgtc agtcttcctc ttccccccaa aacccaagga cccctcatg    480
atctcccgga cccctgaggt cacatgcgtg gtggtggacg tgagccacga agaccctgag    540
gtcaagttca actggtacgt ggacggcgtg gaggtgcata atgccaagac aaagccgcgg    600
gaggagcagt acaacagcac gtaccgtgtg gtcagcgtcc tcaccgtcct gcaccaggac    660
tggctgaatg gcaaggagta caagtgcaag gtctccaaca agccccgtgc agccccatc    720
gagaaaacca tctccaaagc caaagggcag ccccgagaac acaggtgac acccctgccc    780
ccatcccggg atgagctgac caagaaccag gtcagcctga cctgcctggt caaaggcttc    840
tatcccagcg acatcgccgt ggagtgggag agcaatgggc agccggagaa caactacaag    900
accttccctc ccgtgctgga ctccgacggc tccttcttcc tctacagcaa gctcaccgtg    960
gacaagagca ggtggcagca ggggaacgtc ttctcatgct ctgtgatgca tgaggctctg    1020
cataaccact acacgcagaa gagcctctcc ctgtctccgg gtaaaggagg cggtggatca    1080
gagaaactgg gaaaacttca gtattcactg gattatgatt tccaaaataa ccagctgctg    1140
gtagggatca ttcaggctgc cgaactgccc gccttgatgg gaggtacaag cgatcctgtg    1200
tacgtgaaag tgttctgct acctgataag aagaagaaat tgagacaaa agtccaccga    1260
aaaacccta atcctgtctt caatgagcaa tttactttca aggtaccata ctcggaattg    1320
ggtggcaaaa ccctagtgat ggctgtatat gatttgatc gtttctctaa gcatgacatc    1380
attggagaat ttaaagtccc tatgaacaca gtggattttg gccatgtaac tgaggaatgg    1440
cgtgacctgc aaagtgct                                                  1458

SEQ ID NO: 8              moltype = AA  length = 486
FEATURE                   Location/Qualifiers
source                    1..486
                          mol_type = protein
                          organism = Homo sapiens
SEQUENCE: 8
GQFRVIGPGY PIRALVGDEA ELPCRISPGK NATGMEVGWY RSPFSRVVHL YRNGKDQAE     60
QAPEYRGRTE LLKETISEGK VTLRIQNVRF SDEGGYTCFF RDHSYQEEAA MELKVEDGGG    120
GSVEPKSSDK THTCPPCPAP ELLRGPSVFL FPPKPKDTLM ISRTPEVTCV VVDVSHEDPE    180
VKFNWYVDGV EVHNAKTKPR EEQYNSTYRV VSVLTVLHQD WLNGKEYKCK VSNKARPAPI    240
EKTISKAKGQ PREPQVYTLP PSRDELTKNQ VSLTCLVKGF YPSDIAVEWE SNGQPENNYK    300
TFPPVLDSDG SFFLYSKLTV DKSRWQQGNV FSCSVMHEAL HNHYTQKSLS LSPGKGGGGS    360
EKLGKLQYSL DYDFQNNQLL VGIIQAAELP ALDMGGTSDP YVKVFLLPDK KKFETKVHR    420
KTLNPVFNEQ FTFKVPYSEL GGKTLVMAVY DFDRFSKHDI IGEFKVPMNT VDFGHVTEEW    480
```

RDLQSA                                                                      486

SEQ ID NO: 9              moltype = DNA    length = 1092
FEATURE                   Location/Qualifiers
source                    1..1092
                          mol_type = genomic DNA
                          organism = Homo sapiens
SEQUENCE: 9
gttgagccca aatcttctga caaaactcac acatgcccac cgtgcccagc acctgaactc    60
ctgagggggac cgtcagtctt cctcttcccc ccaaaaccca aggacaccct catgatctcc   120
cggacccctg aggtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagccccga gaaccacagg tgtacaccct gcccccatcc   420
cgggatgagc tgaccaagaa ccaggtcacc ctgacctgcc tggtcaaagg cttctatccc   480
agcgacatcg ccgtggagtg ggagagcaat gggcagccgg agaacaacta caagaccacg   540
cctcccgtgc tggactccga cggctccttc gccctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaag gaggcggtgg atcagagaaa   720
ctgggaaaac ttcagtattc actggattat gatttccaaa ataaccagct gctggtaggg   780
atcattcagg ctgccgaact gcccgccttg gacatggggg gcacatctga tccttacgtg   840
aaagtgtttc tgcctacctga taagaagaag aaatttgaga caaaagtcca ccgaaaaacc   900
cttaatcctg tcttcaatga gcaatttact ttcaaggtac catactcgga attgggtggc   960
aaaacccctag tgatggctgt atatgatttt gatcgtttct ctaagcatga catcattgga  1020
gaatttaaag tccctatgaa cacagtggat tttggccatg taactgagga atggcgtgac  1080
ctgcaaagtg ct                                                        1092

SEQ ID NO: 10             moltype = AA    length = 364
FEATURE                   Location/Qualifiers
source                    1..364
                          mol_type = protein
                          organism = Homo sapiens
SEQUENCE: 10
VEPKSSDKTH TCPPCPAPEL LRGPSVFLFP PKPKDTLMIS RTPEVTCVVV DVSHEDPEVK     60
FNWYVDGVEV HNAKTKPREE QYNSTYRVVS VLTVLHQDWL NGKEYKCKVS NKARPAPIEK    120
TISKAKGQPR EPQVYTLPPS RDELTKNQVH LTCLVKGFYP SDIAVEWESN GQPENNYKTT    180
PPVLDSDGSF ALYSKLTVDK SRWQQGNVFS CSVMHEALHN HYTQKSLSLS PGKGGGGSEK    240
LGKLQYSLDY DFQNNQLLVG IIQAAELPAL DMGGTSDPYV KVFLLPDKKK KFETKVHRKT    300
LNPVFNEQFT FKVPYSELGG KTLVMAVYDF DRFSKHDIIG EFKVPMNTVD FGHVTEEWRD    360
LQSA                                                                 364

SEQ ID NO: 11             moltype = DNA    length = 1458
FEATURE                   Location/Qualifiers
source                    1..1458
                          mol_type = genomic DNA
                          organism = Homo sapiens
SEQUENCE: 11
ggacaattca gagtgatagg accagggtat cccatccggg ctttagttgg ggatgaagca     60
gagctgccgt gccgcatctc tcctgggaaa atgccacgg gcatggaggt gggttggtac    120
cgttctcccct tctcaagagt ggttcacctc taccgaaatg gcaaggacca agatgcagag   180
caagcacctg aataccgggg acgcacagag cttctgaaag agactatcag tgagggaaag   240
gttacccctta ggattcagaa cgtgagattc tcagatgaag gaggctacac ctgcttcttc   300
agagaccact cttaccaaga gaggcagca atggagttga agtgtgaaga tggaggcggt   360
ggatcagttg agcccaaatc ttctgacaaa actcacacat gcccaccgtg ccagcacct   420
gaactcctga ggggaccgtc agtcttcctc ttccccccaa aacccaagga caccctcatg   480
atctcccgga cccctgaggt cacatgcgtg gtggtggacg tgagccacga agaccctgag   540
gtcaagtttca actggtacgt ggacggcgtg gaggtgcata atgccaagac aaagccgcgg   600
gaggagcagt acaacagcac gtaccgtgtg gtcagcgtcc tcaccgtcct gcaccaggac   660
tggctgaatg gcaaggagta caagtgcaag gtctccaaca aagcccgccc agccccatc   720
gagaaaacca tctccaaagc caagggcag ccccgagaac acaggtgac cccctgccc   780
ccatcccggg atgagctgac caagaaccag gtcagcctga cctgcctggt caaaggcttc   840
tatcccagcg acatcgccgt ggagtgggag agcaatggc agccggagaa caactacgac   900
accttcctc ccgtgctgga ctccgacggc tccttcttcc tctacagcaa gctcaccgtg   960
gacaagagcc ggtggcagca ggggaacgtc ttctcatgct ctgtgatgca tgaggctctg  1020
cataaccact acacgcagaa gagcctctcc ctgtctccgg gtaaaggagg cggtggatca  1080
gagaaactgg gaaaacttca gtattcactg gattatgatt tccaaaataa ccagctgctg  1140
gtagggatca ttcaggctgc cgaactgccc gccttggaca tggggggcac atctgatcct  1200
tacgtgaaag tgtttctgct acctgataag aagaagaaa ttgagacaaa agtccaccga  1260
aaaaccctta atcctgtctt caatgagcaa tttactttca aggtaccata ctcggaattg  1320
ggtggcaaaa ccctagtgat ggctgtatat gattttgatc gtttctctaa gcatgacatc  1380
attggagaat ttaaagtccc tatgaacaca gtggattttg ccatgtaac tgaggaatgg  1440
cgtgacctgc aaagtgct                                                1458

SEQ ID NO: 12             moltype = AA    length = 486
FEATURE                   Location/Qualifiers
source                    1..486
                          mol_type = protein
                          organism = Homo sapiens

```
SEQUENCE: 12
GQFRVIGPGY PIRALVGDEA ELPCRISPGK NATGMEVGWY RSPFSRVVHL YRNGKDQDAE    60
QAPEYRGRTE LLKETISEGK VTLRIQNVRF SDEGGYTCFF RDHSYQEEAA MELKVEDGGG   120
GSVEPKSSDK THTCPPCPAP ELLRGPSVFL FPPKPKDTLM ISRTPEVTCV VVDVSHEDPE   180
VKFNWYVDGV EVHNAKTKPR EEQYNSTYRV VSVLTVLHQD WLNGKEYKCK VSNKARPAPI   240
EKTISKAKGQ PREPQVTTLP PSRDELTKNQ VSLTCLVKGF YPSDIAVEWE SNGQPENNYD   300
TPPPVLDSDG SFFLYSDLTV DKSRWQQGNV FSCSVMHEAL HNHYTQKSLS LSPGKGGGGS   360
EKLGKLQYSL DYDFQNNQLL VGIIQAAELP ALDMGGTSDP YVKVFLLPDK KKKFETKVHR   420
KTLNPVFNEQ FTFKVPYSEL GGKTLVMAVY DFDRFSKHDI IGEFKVPMNT VDFGHVTEEW   480
RDLQSA                                                              486

SEQ ID NO: 13          moltype = DNA  length = 1092
FEATURE                Location/Qualifiers
source                 1..1092
                       mol_type = genomic DNA
                       organism = Homo sapiens
SEQUENCE: 13
gttgagccca aatcttctga caaaaactcac acatgcccac cgtgcccagc acctgaactc    60
ctgaggggac cgtcagtctt cctcttcccc ccaaaaccca aggacaccct catgatctcc   120
cggacccctg aggtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc gcccagcccc catcgagaaa   360
accatctcca aagccaaagg gcagccccga gaaccacagg tgtacaccct gcccccatcc   420
cgggataagc tgaccaagaa ccaggtccac ctgacctgcc tggtcaaagg cttctatccc   480
agcgacatcg ccgtggagtg ggagagcaat gggcagccgg agaacaacta caagaccacg   540
cctcccgtgc tgaagtccga cggctccttc gccctctaca gcaagctcac cgtggacaag   600
agcaggtggc agcaggggaa cgtcttctca tgctccgtga tgcatgaggc tctgcacaac   660
cactacacgc agaagagcct ctccctgtct ccgggtaaag gaggcggtgg atcagagaaa   720
ctgggaaaac ttcagtattc actgattat gatttccaaa ataaccagct gctggtaggg   780
atcattcagg ctgccgaact gcccgccttg gacatggggg gcacatctga tccttacgtg   840
aaagtgtttc tgctacctga taagaagaag aaatttgaga caaaagtcca ccgaaaaacc   900
cttaatcctg tcttcaatga gcaatttact ttcaaggtac atactcgga attgggtggc   960
aaaaaccctag tgatggctgt atatgatttt gatcgttct ctaagcatga catcattgga  1020
gaatttaaag tcccctatgaa cacagtggat tttggccatg taactgagga atggcgtgac  1080
ctgcaaagtg ct                                                       1092

SEQ ID NO: 14          moltype = AA  length = 364
FEATURE                Location/Qualifiers
source                 1..364
                       mol_type = protein
                       organism = Homo sapiens
SEQUENCE: 14
VEPKSSDKTH TCPPCPAPEL LRGPSVFLFP PKPKDTLMIS RTPEVTCVVV DVSHEDPEVK    60
FNWYVDGVEV HNAKTKPREE QYNSTYRVVS VLTVLHQDWL NGKEYKCKVS NKARPAPIEK   120
TISKAKGQPR EPQVYTLPPS RDKLTKNQVH LTCLVKGFYP SDIAVEWESN GQPENNYKTT   180
PPVLDSDGSF ALYSKLTVDK SRWQQGNVFS CSVMHEALHN HYTQKSLSLS PGKGGGGSEK   240
LGKLQYSLDY DFQNNQLLVG IIQAAELPAL DMGGTSDPYV KVFLLPDKKK KFETKVHRKT   300
LNPVFNEQFT FKVPYSELGG KTLVMAVYDF DRFSKHDIIG EFKVPMNTVD FGHVTEEWRD   360
LQSA                                                                364

SEQ ID NO: 15          moltype = DNA  length = 1704
FEATURE                Location/Qualifiers
source                 1..1704
                       mol_type = genomic DNA
                       organism = Homo sapiens
SEQUENCE: 15
gaggtgcagc tggtgcagtc cggcgccgag gtgaagaagc ccggcgcctc cgtgaaggtg    60
tcctgcaagg cctccggcta caccttcacc tcctactgga tgcactgggt gcggcaggcc   120
cccgccaagg ggctggagtg gatcggcgag atcaacccca ccaacggccg gaccaactac   180
atcgagaagt tcaagtcccg ggccaccctg accgtggaca gtccgcctc caccgcctac   240
atggagctgt cctccctgcg gtccgaggac accgccgtgt actactgcgc cggggcacc   300
cgggcctacc actactgggg ccagggcacc atggtgaccg tgtcctccgc ctccaccaag   360
ggcccatcgg tcttcccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca cacctttccg gctgtcctac agtcctcagg actctactcc   540
ctcagcagcg tggtgactgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggag agtacaacag cacgtaccgt   900
gtggtcagcg tccttaccgt cctgcaccag gactggctga atggcaagga gtacaagtgc   960
aaggtctcca acaaagccct cccagccccc atcgagaaaa ccatctctcca aagccaaagg  1020
cagccccgag aaccacaggt gtaccaccctg cccccatccc gggatgagct gaccaagaac  1080
caggtcagcc tgacctgcct ggtcaaaggc ttctatccca gcgacatcgc cgtggagtgg  1140
gagagcaatg gcagccgga gaacaactac aagaccttcc ctcccgtgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
```

```
tccctgtctc cgggtaaagg aggcggtgga tcaggacaat tcagagtgat aggaccaggg   1380
tatcccatcc gggctttagt tggggatgaa gcagagctgc cgtgccgcat ctctcctggg   1440
aaaaatgcca cgggcatgga ggtgggttgg taccgttctc ccttctcaag agtggttcac   1500
ctctaccgaa atggcaagga ccaagatgca gagcaagcac ctgaataccg ggacgcaca   1560
gagcttctga aagagactat cagtgaggga aaggttaccc ttaggattca gaacgtgaga   1620
ttctcagatg aaggaggcta cacctgcttc ttcagagacc actcttacca agaagaggca   1680
gcaatggagt tgaaagtgga agat                                         1704

SEQ ID NO: 16           moltype = AA   length = 568
FEATURE                 Location/Qualifiers
source                  1..568
                        mol_type = protein
                        organism = Homo sapiens
SEQUENCE: 16
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTFPPVLDSD GSFFLYSKLT VDKSRWQQGN   420
VFSCSVMHEA LHNHYTQKSL SLSPGKGGGG SGQFRVIGPG YPIRALVGDE AELPCRISPG   480
KNATGMEVGW YRSPFSRVVH LYRNGKDQDA EQAPEYRGRT ELLKETISEG KVTLRIQNVR   540
FSDEGGYTCF FRDHSYQEEA AMELKVED                                     568

SEQ ID NO: 17           moltype = DNA   length = 1338
FEATURE                 Location/Qualifiers
source                  1..1338
                        mol_type = genomic DNA
                        organism = Homo sapiens
SEQUENCE: 17
gaggtgcagc tggtgcagtc cggcgccgag gtgaagaagc ccggcgcctc cgtgaaggtg     60
tcctgcaagg cctccggcta caccttcacc tcctactgga tgcactgggt gcggcaggcc   120
cccggccagc ggctggagtg gatcggcgag atcaaccca ccaacggccg gaccaactac   180
atcgagaagt tcaagtcccg ggccaccctg accgtggaca gtccgccctc caccgcctac   240
atggagctgt cctccctgcg gtccgaggac accgccgtgt actactgcgc ccggggcacc   300
cgggcctacc actactgggg ccagggcacc atggtgaccg tgtcctccgc ctccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg gaactcaggc   480
gccctgacca gcggcgtgca caccttcccg gctgtcctac agtcctcagg actctactcc   540
ctcagcagcg tggtgactgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tggggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagccct cccagccccc atcgagaaaa ccatctccaa agccaaaggg  1020
cagccccgag aaccacaggt gtacaccctg cccccatccc gggatgagct gaccaagaac  1080
caggtcacc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttcg ccctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                1338

SEQ ID NO: 18           moltype = AA   length = 446
FEATURE                 Location/Qualifiers
source                  1..446
                        mol_type = protein
                        organism = Homo sapiens
SEQUENCE: 18
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVHLTCLVKG FYPSDIAVEW ESNGQPENNY KTTPPVLDSD GSFALYSKLT VDKSRWQQGN   420
VFSCSVMHEA LHNHYTQKSL SLSPGK                                       446

SEQ ID NO: 19           moltype = DNA   length = 639
FEATURE                 Location/Qualifiers
source                  1..639
                        mol_type = genomic DNA
                        organism = Homo sapiens
SEQUENCE: 19
gacatccaga tgacccagtc cccctcctcc ctgtccgcct ccgtgggcga ccgggtgacc     60
atcacctgcc gggcctccga caacctgtac tccaacctgg cctggtacca gcagaagccc   120
ggcaagtccc ccaagctgct ggtgtacgac gccaccaacc tggccgacgg cgtgccctcc   180
```

```
cggttctccg gctccggctc cggcaccgac tacaccctga ccatctcctc cctgcagccc    240
gaggacttcg ccacctacta ctgccagcac ttctggggca ccccctgac cttcggccag     300
ggcaccaagg tggagatcaa gactgtggct gcaccatctg tcttcatctt cccgccatct    360
gatgagcagt tgaaatctgg aactgcctct gttgtgtgcc tgctgaataa cttctatccc    420
agagaggcca aagtacagtg gaaggtggat aacgccctcc aatgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agttcgcccg tcacaaagag cttcaacagg ggagagtgt                           639

SEQ ID NO: 20              moltype = AA   length = 213
FEATURE                    Location/Qualifiers
source                     1..213
                           mol_type = protein
                           organism = Homo sapiens
SEQUENCE: 20
DIQMTQSPSS LSASVGDRVT ITCRASDNLY SNLAWYQQKP GKSPKLLVYD ATNLADGVPS     60
RFSGSGSGTD YTLTISSLQP EDFATYYCQH FWGTPLTFGQ GTKVEIKTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                 213

SEQ ID NO: 21              moltype = DNA   length = 1704
FEATURE                    Location/Qualifiers
source                     1..1704
                           mol_type = genomic DNA
                           organism = Homo sapiens
SEQUENCE: 21
gaggtgcagc tggtgcagtc cggcgccgag gtgaagaagc ccggcgcctc cgtgaaggtg     60
tcctgcaagg cctccggcta caccttcacc tcctactgga tgcactgggt gcggcaggcc    120
cccgccagc ggctggagtg gatcggcgag atcaaccccca ccaacggccg gaccaactac    180
atcgagaagt tcaagtcccg ggccaccctg accgtgaca agtccgcctc caccgcctac    240
atggagctgt cctccctgcg gtccgaggac accgccgtgt actactgcgc ccggggcacc    300
cgggcctacc actactgggg ccagggcacc atggtgaccg tgtcctccgc ctccaccaag    360
ggcccatcgg tcttcccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgactgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tccttaccgt cctgcaccag gactggctga atggcaagga gtacaagtgc    960
aaggtctcca acaaagcccg cccagccccc atcgagaaaa ccatctccaa agccaaaggg   1020
cagccccgag aaccacaggt gtaccaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccttcc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaagg aggcggtgga tcaggacaat tcagtgat aggaccaggg     1380
tatcccatcc gggctttagt tggggatgaa gcagagctgc cgtgccgcat ctctcctggg   1440
aaaaatgcca cgggcatgga ggtgggttgg taccgttctc ccttctcaag agtggttcac   1500
ctctaccgaa atggcaagga ccaagatgca gagcaagcac tgaataccg ggacgcaca     1560
gagcttctga aagagactat cagtgaggga aaggttaccc ttaggattca gaacgtgaga   1620
ttctcagatg aaggaggcta cacctgcttc ttcagagacc actcttacca agaagaggca   1680
gcaatggagt tgaaagtgga agat                                          1704

SEQ ID NO: 22              moltype = AA   length = 568
FEATURE                    Location/Qualifiers
source                     1..568
                           mol_type = protein
                           organism = Homo sapiens
SEQUENCE: 22
EVQLVQSGAE VKKPGASVKV SCKASGYTFT SYWMHWVRQA PGQRLEWIGE INPTNGRTNY     60
IEKFKSRATL TVDKSASTAY MELSSLRSED TAVYYCARGT RAYHYWGQGT MVTVSSASTK    120
GPSVFPLAPS SKSTSGGTAA LGCLVKDYFP EPVTVSWNSG ALTSGVHTFP AVLQSSGLYS    180
LSSVVTVPSS SLGTQTYICN VNHKPSNTKV DKKVEPKSCD KTHTCPPCPA PELLRGPSVF    240
LFPPKPKDTL MISRTPEVTC VVVDVSHEDP EVKFNWYVDG VEVHNAKTKP REEQYNSTYR    300
VVSVLTVLHQ DWLNGKEYKC KVSNKARPAP IEKTISKAKG QPREPQVYTL PPSRDELTKN    360
QVSLTCLVKG FYPSDIAVEW ESNGQPENNY KTFPPVLDSD GSFFLYSKLT VDKSRWQQGN    420
VFSCSVMHEA LHNHYTQKSL SLSPGKGGGG SGQFRVIGPG YPIRALVGDE AELPCRISPG    480
KNATGMEVGW YRSPFSRVVH LYRNGKDQDA EQAPEYRGRT ELLKETISEG KVTLRIQNVR    540
FSDEGGYTCF FRDHSYQEEA AMELKVED                                      568

SEQ ID NO: 23              moltype = DNA   length = 1338
FEATURE                    Location/Qualifiers
source                     1..1338
                           mol_type = genomic DNA
                           organism = Homo sapiens
SEQUENCE: 23
```

```
gaggtgcagc tggtgcagtc cggcgccgag gtgaagaagc ccggcgcctc cgtgaaggtg    60
tcctgcaagg cctccggcta caccttcacc tcctactgga tgcactgggt gcggcaggcc   120
cccggccagc ggctggagtg gatcggcgag atcaaccccca ccaacggccg gaccaactac   180
atcgagaagt tcaagtcccg ggccacccctg accgtggaca gtccgcctc caccgcctac   240
atggagctgt cctccctgcg gtccgaggac accgccgtgt actactgcgc ccggggcacc   300
cgggcctacc actactgggg ccagggcacc atggtgaccg tgtcctccgc ctccaccaag   360
ggcccatcgg tcttccccct ggcaccctcc tccaagagca cctctggggg cacagcggcc   420
ctgggctgcc tggtcaagga ctacttcccc gaaccggtga cggtgtcgtg aactcaggc   480
gccctgacca gcggcgtgca caccttcccg gctgtcctac agtcctcagg actctactcc   540
ctcagcagcg tggtgactgt gccctccagc agcttgggca cccagaccta catctgcaac   600
gtgaatcaca agcccagcaa caccaaggtg gacaagaaag ttgagcccaa atcttgtgac   660
aaaactcaca catgcccacc gtgcccagca cctgaactcc tgggggacc gtcagtcttc   720
ctcttccccc caaaacccaa ggacaccctc atgatctccc ggacccctga ggtcacatgc   780
gtggtggtgg acgtgagcca cgaagaccct gaggtcaagt tcaactggta cgtggacggc   840
gtggaggtgc ataatgccaa gacaaagccg cgggaggagc agtacaacag cacgtaccgt   900
gtggtcagcg tcctcaccgt cctgcaccag gactggctga atggcaagga gtacaagtgc   960
aaggtctcca acaaagcccg cccagccccc atcgagaaaa ccatctccaa agccaaaggg  1020
cagccccgag aaccacaggt gtacaccctg cccccatccc gggatgagct gaccaagaac  1080
caggtcacc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttcg ccctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaa                                                 1338

SEQ ID NO: 24          moltype = AA  length = 446
FEATURE                Location/Qualifiers
source                 1..446
                       mol_type = protein
                       organism = Homo sapiens
SEQUENCE: 24
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLRGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKARPAP IEKTISKAKG QPREPQVYTL PPSRDELTKN   360
QVHLTCLVKG FYPSDIAVEW ESNGQPENNY KTTPPVLDSD GSFALYSKLT VDKSRWQQGN   420
VFSCSVMHEA LHNHYTQKSL SLSPGK                                        446

SEQ ID NO: 25          moltype = DNA  length = 2601
FEATURE                Location/Qualifiers
source                 1..2601
                       mol_type = genomic DNA
                       organism = Homo sapiens
SEQUENCE: 25
acccaagtgt gcaccggcac agacatgaag ctgcggctcc ctgccagtcc cgagacccac    60
ctggacatgc tccgccacct ctaccagggg tgccaggtgg tgcagggaaa cctggaactc   120
acctacctgc ccaccaatgc cagcctgtcc ttcctgcagg atatccagga ggtgcagggc   180
tacgtgctca tcgctcacaa ccaagtgagg caggtccacc tgcagaggct gcggattgtg   240
cgaggcaccc agctctttga ggacaactat gccctggccg tgctagacaa tggagacccg   300
ctgaacaata ccacccctgt cacagggggcc tccccaggag gcctgcgggga gctgcagctt   360
cgaagcctca cagagatctt gaaaggaggg gtcttgatcc agcggaaccc ccagctctgt   420
taccaggaca cgattttgtg gaaggacatc ttccacaaga caaccagct ggctctcaca   480
ctgatagaca ccaaccgctc tcgggcctgc caccctgtt ctccgatgtg taagggctcc   540
cgctgctggg gagagagttc tgaggattgt cagagcctga cgcgcactgt ctgtgccggt   600
ggctgtgccc gctgcaaggg gccactgccc actgactgct gccatgagca gtgtgctcgg   660
ggctgcacgg gccccaagca ctctgactgc ctggcctgcc tccacttcaa ccacagtggc   720
atctgtgagc tgcactgccc agccctggtc acctacaaca cagacacgtt tgagtccatg   780
cccaatcccg agggccggta tacattcggc gccagtcgtg tgactgcctg tccctacaac   840
taccttttcta cggacgtggg atcctgcacc ctcgtctgcc ccctgcacaa ccaagaggtg   900
acagcagagg atgaacacac gcggtgtgag aagtgcagca gccctgtgc ccagtgtgc   960
tatggtctgg gcatggagca cttgcgagag gtgagggcag ttaccagtgc caatatccag  1020
gagtttgctg gctgcaagaa gatctttggg agcctgcat ttctgccgga gagcttttgat  1080
ggggacccag cctccaacac tgccccgctc agccagagc agtccaagt gtttgagact  1140
ctggaagaga tcacaggtta cctatacatc tcagcatgcc cggacagcct cctgactc   1200
agcgtcttcc agaacctgca agtaatccgg ggacgaattc tgcacaatgg cgcctactcg  1260
ctgacccctg aagggctggg catcagctgg ctggggctgc gctcactgag ggaactgggc  1320
agtggactgg ccctcatcca ccataacacc cacctgtgct tcgtgcacac ggtgccctgg  1380
gaccagctct ttcggaaccc gccccaagct ctgctccaca ctgccaaccg gccagaggac  1440
gagtgtgtgg cgcagggcct ggcctgccac cagctgcgcg cccgagggca ctgctggggt  1500
ccagggcccca cccagtgtgt caactgcagc cagttcctcc ggggccagga gtgcgtggag  1560
gaatgccgag tactgcaggg gctccccagg gagtatgtga atgccaggca ctgtttgccg  1620
tgccaccctg agtgtcagcc ccagaatggc tcagtgacct gttttggacc ggaggctgac  1680
cagtgctgtg cctgtcccca tataaggacc ctccccatcg gctggcgcag  1740
ggtgtgaaac ctgaccctct ctacatgccc atcggaagt tccagatga ggagggcgca  1800
tgccagcctt gccccatcaa ctgcacccac tcctgtgtgg aactggatga caagggctgc  1860
cccgccgagc agagagccag cctctgacg attgaaggcc gcatggatcc caatcttct  1920
gacaaaactc acacatgccc accgtgccca gcacctgaac tcctgggggg accgtcagtc  1980
ttcctcttcc ccccaaaacc caaggacacc ctctacatca ctcgggaacc tgaggtcaca  2040
```

```
tgcgtggtgg tggacgtgag ccacgaagac cctgaggtca agttcaactg gtacgtggac  2100
ggcgtggagg tgcataatgc caagacaaag ccgcggggag gcagtacaac agcacgtac   2160
cgtgtggtca gcgtcctcac cgtcctgcac caggactggc tgaatggcaa ggagtacaag  2220
tgcaaggtct ccaacaaagc cctcccagcc cccatcgaga aaccatctc caaagccaaa   2280
gggcagcccc gagaaccaca ggtgaccacc ctgcccccat cccgggatga gctgaccaag  2340
aaccaggtca gcctgacctg cctggtcaaa ggcttctatc ccagcgacat cgccgtggaa  2400
tgggagagca atgggcagcc ggagaacaac tacaagacct cccctcccgt gctggactcc  2460
gacggctcct tcttcctcta cagcaagctc accgtggaca gagcaggtg gcagcagggg   2520
aacgtcttct catgctctgt gatgcatgag gctctgaaat ccactacac gcagaagagc   2580
ctctccctgt ctcctggtaa a                                            2601

SEQ ID NO: 26          moltype = AA    length = 867
FEATURE                Location/Qualifiers
source                 1..867
                       mol_type = protein
                       organism = Homo sapiens
SEQUENCE: 26
TQVCTGTDMK LRLPASPETH LDMLRHLYQG CQVVQGNLEL TYLPTNASLS FLQDIQEVQG    60
YVLIAHNQVR QVPLQRLRIV RGTQLFEDNY ALAVLDNGDP LNNTTPVTGA SPGGLRELQL   120
RSLTEILKGG VLIQRNPQLC YQDTILWKDI FHKNNQLALT LIDTNRSRAC HPCSPMCKGS   180
RCWGESSEDC QSLTRTVCAG GCARCKGPLP TDCCHEQCAA GCTGPKHSDC LACLHFNHSG   240
ICELHCPALV TYNTDTFESM PNPEGRYTFG ASCVTACPYN YLSTDVGSCT LVCPLHNQEV   300
TAEDGTQRCE KCSKPCARVC YGLGMEHLRE VRAVTSANIQ EFAGCKKIFG SLAFLPESFD   360
GDPASNTAPL QPEQLQVFET LEEITGYLYI SAWPDSLPDL SVFQNLQVIR GRILHNGAYS   420
LTLQGLGISW LGLRSLRELG SGLALIHHNT HLCFVHTVPW DQLFRNPHQA LLHTANRPED   480
ECVGEGLACH QLCARGHCWG PGPTQCVNCS QFLRGQCVE ECRVLQGLPR EYVNARHCLP    540
CHPECQPQNG SVTCFGPEAD QCVACAHYKD PPFCVARCPS GVKPDLSYMP IWKFPDEEGA   600
CQPCPINCTH SCVDLDDKGC PAEQRASPLT IEGRMDPKSS DKTHTCPPCP APELLGGPSV   660
FLFPPKPKDT LYITREPEVT CVVVDVSHED PEVKFNWYVD GVEVHNAKTK PREEQYNSTY   720
RVVSVLTVLH QDWLNGKEYK CKVSNKALPA PIEKTISKAK GQPREPQVTT LPPSRDELTK   780
NQVSLTCLVK GFYPSDIAVE WESNGQPENN YKTFPPVLDS DGSFFLYSKL TVDKSRWQQG   840
NVFSCSVMHE ALKFHYTQKS LSLSPGK                                      867

SEQ ID NO: 27          moltype = DNA   length = 699
FEATURE                Location/Qualifiers
source                 1..699
                       mol_type = genomic DNA
                       organism = Homo sapiens
SEQUENCE: 27
gttgagccca atcttctga caaaactcac acatgcccac cgtgcccagc acctgaactc     60
ctgggggac cgtcagtctt cctcttcccc ccaaaaccca aggacaccct ctacatcact    120
cgggaacctg aggtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagcccga gaaccacagg tgtacaccct gcccccatcc   420
cgggatgagc tgaccaagaa ccaggtcagc ctgacctgcc tggtcaaagg cttctatccc   480
agcgacatcg ccgtggagtg ggagagcaat gggcagccgg agaacaacta caagaccacg   540
cctcccgtgc tggactccga cggctccttc gccctcaca gcaagctcac cgtggacaag   600
agcaggtggc agcaggggaa cgtcttctca tgctccgtga tgcatgaggc tctgaaattc   660
cactacacgc agaagagcct ccctgtct ccgggtaaa                            699

SEQ ID NO: 28          moltype = AA    length = 233
FEATURE                Location/Qualifiers
source                 1..233
                       mol_type = protein
                       organism = Homo sapiens
SEQUENCE: 28
VEPKSSDKTH TCPPCPAPEL LGGPSVFLFP PKPKDTLYIT REPEVTCVVV DVSHEDPEVK    60
FNWYVDGVEV HNAKTKPREE QYNSTYRVVS VLTVLHQDWL NGKEYKCKVS NKALPAPIEK   120
TISKAKGQPR EPQVYTLPPS RDELTKNQVH LTCLVKGFYP SDIAVEWESN GQPENNYKTT   180
PPVLDSDGSF ALYSKLTVDK SRWQQGNVFS CSVMHEALKF HYTQKSLSLS PGK          233

SEQ ID NO: 29          moltype = DNA   length = 2835
FEATURE                Location/Qualifiers
source                 1..2835
                       mol_type = genomic DNA
                       organism = Homo sapiens
SEQUENCE: 29
gttgagccca atcttctga caaaactcac acatgcccac cgtgcccagc acctgaactc     60
ctgggggac cgtcagtctt cctcttcccc ccaaaaccca aggacaccct ctacatcact    120
cgggaacctg aggtcacatg cgtggtggtg gacgtgagcc acgaagaccc tgaggtcaag   180
ttcaactggt acgtggacgg cgtggaggtg cataatgcca agacaaagcc gcgggaggag   240
cagtacaaca gcacgtaccg tgtggtcagc gtcctcaccg tcctgcacca ggactggctg   300
aatggcaagg agtacaagtg caaggtctcc aacaaagccc tcccagcccc catcgagaaa   360
accatctcca aagccaaagg gcagcccga gaaccacagg tgaccaccct gcccccatcc   420
cgggatgagc tgaccaagaa ccaggtcagc ctgacctgcc tggtcaaagg cttctatccc   480
agcgacatcg ccgtggagtg ggagagcaat gggcagccgg agaacaacta caagaccttg   540
cctcccgtgc tggactccga cggctccttc ttcctctaca gcaagctcac cgtggacaag   600
```

-continued

```
agcaggtggc agcagggaa cgtcttctca tgctctgtga tgcatgaggc tctgaaattc  660
cactacacgc agaagagcct ctccctgtct ccgggtaaag gaggcggtgg atcaaaatcc  720
tccaatgaag ctactaacat tactccaaag cataatatga aagcattttt ggatgaattg  780
aaagctgaga acatcaagaa gttcttatat aattttacac agataccaca tttagcagga  840
acagaacaaa actttcagct tgcaaagcaa attcaatccc agtggaaaga atttggcctg  900
gattctgttg agctagcaca ttatgatgtc ctgttgtcct acccaaataa gactcatccc  960
aactacatct caataattaa tgaagatgga aatgagattt caacacatc attatttgaa 1020
ccacctcctc caggatatga aaatgtttcg gatattgtac cactttcag tgcttttctct 1080
cctcaaggaa tgcagagggg cgatcagtg tatgttaact atgcacgaac tgaagacttc 1140
tttaaattgg aacgggacat gaaaatcaat tgctctggga aaattgtaat tgccagatat 1200
gggaaagttt tcagaggaaa taaggttaaa aatgcccagc tggcaggggc caaaggagtc 1260
attctctact ccgaccctgc tgactacttt gctcctgggg tgaagtccta tccagatggt 1320
tggaatcttc ctggaggtgg tgtccagcgt ggaaatatcc taaatctgaa tggtgcagga 1380
gaccctctca ccaccggtta cccagcaaat gaatatgctt ataggcgtgg aattgcagag 1440
gctgttggtc ttccaagtat tcctgttcat ccaattggat actatgatgc acagaagctc 1500
ctagaaaaaa tgggtggctc agcaccacca gatagcagct ggaggaagaag tctcaaagtg 1560
ccctacaatg ttggacctgg ctttactgga aacttttcta cacaaaaagt caagatgcac 1620
atccactcta ccaatgaagt gacaagaatt tacaatgtga taggtactct cagaggagca 1680
gtggaaccag acagatatgt cattctggga ggtcaccggg actcatgggt gtttggtggt 1740
attgaccctc agagtggagc agctgttgtt catgaaattg tgaggagctt tggaacactg 1800
aaaaaggaag ggtggagacc tagaagaaca attttgtttg caagctggga tgcagaagaa 1860
tttggtcttc ttggttctac tgagtgggca gaggagaatt caagactcct tcaagagcgt 1920
ggcgtggctt atattaatgc tgactcatct atagaaggaa actacactgt gagagttgat 1980
tgtacaccgc tgatgtacag cttggtacac aacctaacaa aagagctgaa aagccctgat 2040
gaaggctttg aaggcaaatc tctttatgaa agttggacta aaaaagtcc ttccccagag 2100
ttcagtggca tgcccaggat aagcaaattg gatctggaaa tgattttga ggtgttcttc 2160
caacgacttg gaattgcttc aggcagagca cggtatacta aaaattggga aacaaacaaa 2220
ttcagcggct atccactgta tcacagtgtc tatgaaacat atgagttggt ggaaaagttt 2280
tatgatccaa tgtttaaata tcacctcact gtggcccagg ttcgaggagg gatggtgttt 2340
gagctagcca attccatagt gctcccttt gattgtcgag attatgctgt agttttaaga 2400
aagtatgctg acaaaatcta cagtatttct atgaaacat cacaggaaat gaagactac 2460
agtgtatcat ttgattcact tttttctgca gtaaagaatt ttacagaaat tgcttccaag 2520
ttcagtgaga gactccagga ctttgacaaa agcaacccaa tagtattaag aatgatgaat 2580
gatcaactca tgtttctgga aagagcattt attgatccat tagggttacc agacaggcct 2640
ttttataggc atgtcatcta tgctccaagc agccacaaca agtatgcagg ggagtcattc 2700
ccaggaattt atgatgctct gtttgatatt gaaagcaaag tggacccttc caaggcctgg 2760
ggagaagtga agagacagat ttatgttgca gccttcacag tgcaggcagc tgcagagact 2820
ttgagtgaag tagcc                                                 2835
```

SEQ ID NO: 30        moltype = AA  length = 945
FEATURE               Location/Qualifiers
source                1..945
                        mol_type = protein
                        organism = Homo sapiens
SEQUENCE: 30

```
VEPKSSDKTH TCPPCPAPEL LRGPSVFLFP PKPKDTLYIT REPEVTCVVV DVSHEDPEVK  60
FNWYVDGVEV HNAKTKPREE QYNSTYRVVS VLTVLHQDWL NGKEYKCKVS NKARPAPIEK 120
TISKAKGQPR EPQVTTLPPS RDELTKNQVS LTCLVKGFYP SDIAVEWESN GQPENNYKTF 180
PPVLDSDGSF FLYSKLTVDK SRWQQGNVFS CSVMHEALHN HYTQKSLSLS PGKGGGGSKS 240
SNEATNITPK HNMKAFLDEL KAENIKKFLY NFTQIPHLAG TEQNFQLAKQ IQSQWKEFGL 300
DSVELAHYDV LLSYPNKTHP NYISIINEDG NEIFNTSLFE PPPPGYENVS DIVPPFSAFS 360
PQGMPEGDLV YVNYARTEDF FKLERDMKIN CSGKIVIARY GKVFRGNVK NAQLAGAKGV 420
ILYSDPADYF APGVKSYPDG WNLPGGGVQR GNILNLNGAG DPLTPGYPAN EYAYRRGIAE 480
AVGLPSIPVH PIGYYDAQKL LEKMGGSAPP DSSWRGSLKV PYNVGPGFTG NFSTQKVKMH 540
IHSTNEVTRI YNVIGTLRGA VEPDRYVILG GHRDSWVFGG IDPQSGAAVV HEIVRSFGTL 600
KKEGWRPRRT ILFASWDAEE FGLLGSTEWA EENSRLLQER GVAYINADSS IEGNYTLRVD 660
CTPLMYSLVH NLTKELKSPD EGFEGKSLYE SWTKKSPSPE FSGMPRISKL GSGNDFEVFF 720
QRLGIASGRA RYTKNWETNK FSGYPLYHSV YETYELVEKF YDPMFKYHLT VAQVRGGMVF 780
ELANSIVLPF DCRDYAVVLR KYADKIYSIS MKHPQEMKTY SVSFDSLFSA VKNFTEIASK 840
FSERLQDFDK SNPIVLRMMN DQLMFLERAF IDPLGLPDRP FYRHVIYAPS SHNKYAGESF 900
PGIYDALFDI ESKVDPSKAW GEVKRQIYVA AFTVQAAAET LSEVA                945
```

SEQ ID NO: 31        moltype = DNA  length = 2469
FEATURE               Location/Qualifiers
source                1..2469
                        mol_type = genomic DNA
                        organism = Homo sapiens
SEQUENCE: 31

```
atggcatctc cgggtctgg cttttggtct tcgggtcgg aagatggctc tggggattcc   60
gagaatcccg gcacagcgcg agcctggtgc caagtggctc agaagttcac gggcggcatc  120
ggaaacaaac tgtgcgccct gctctacgga gacgccgaga gccggcgga gagcggcggg  180
agccaacccg cgcgggccgc cgcccggaag gccgcctgcg cctgcgacca gaagccctgc  240
agctgctcca agtggatgt caactacgcg tttctccatg caacagacct gctgccggc   300
tgtgatggag aaaggcccac tttggcgttt ctgcaagatg ttatgaacat tttacttcag  360
tatgtggtga aaagtttcga tagatcaacc aaagtgattg atttcccatta tcctaatgag  420
cttctccaag aatataatttg ggaattgca gaccaaccac aaaaatttga ggaaattttg  480
atgcattgcc aaacaactct aaaatatgca attaaacag gcatcctag atacttcaat  540
caactttcta ctgggtttga tatggttgga ttagcagcag actggctgac atcaacagca  600
aatactaaca tgttcaccta tgaaatgtgt ccagtatttg tgcttttgga atatgtcaca  660
```

```
ctaaagaaaa tgagagaaat cattggctgg ccagggggct ctggcgatgg gatattttct    720
cccggtggcg ccatatctaa catgtatgcc atgatgatcg cacgctttaa gatgttccca    780
gaagtcaagg agaaaggaat ggctgctctt cccaggctca ttgcccttca cgtctgaacat   840
agtcattttt ctctcaagaa gggagctgca gccttaggga ttggaacaga cagcgtgatt    900
ctgattaaat gtgatgagag agggaaaatg attccatctg atcttgaaag aaggattctt    960
gaagccaaac agaaagggtt tgttcctttc ctcgtgagtg ccacagctgg aaccaccgtg   1020
tacgagcat tgaccccct cttagctgtc gctgacattt gcaaaaagta taagatctgg     1080
atgcatgtgg atgcagcttg gggtggggga ttactgatgt cccgaaaaca caagtggaaa   1140
ctgagtggcg tggagagggc caactctgtg acgtggaatc cacacaagat gatgggagtc   1200
cctttgcagt gctctgctct cctggttaga gaagagggat tgatgcagaa ttgcaaccaa   1260
atgcatgcct cctacctctt tcagcaagat aaacattatg acctgtccta tgacactgga   1320
gacaaggcct acagtgcgg acgccacgtt gatgttttta aactatggct gatgtggagg    1380
gcaaagggga ctaccgggtt tgaagcgcat gttgataaat gtttggagtt ggcagagtat   1440
ttatacaaca tcataaaaaa ccgagaagga tatgagatgg tgtttgatgg gaagcctcag   1500
cacacaaatg tctgcttctg gtacattcct ccaagcttgc gtactctgga agacaatgaa   1560
gagagaatga gtcgcctctc gaaggtggct ccagtgatta agccagaat gatggagtat   1620
ggaaccacaa tggtcagcta ccaacccttg ggagacaagg tcaatttctt ccgcatggtc   1680
atctcaaacc cagccgccaac tcaccaagac attgacttcc tgattgaaga aatagaaccgc   1740
cttggacaag atttaggagg cggtggatca gttgagccca atcttctga caaaactcac    1800
acatgcccac cgtgcccagc acctgaactc ctgaggggac cgtcagtctt cctcttcccc   1860
ccaaaaccca aggacaccct ctacatcact cgggaacctg aggtcacatg cgtggtggtg   1920
gacgtgagcc acgaagaccc tgaggtcaag ttcaactggt acgtggacgg cgtggaggtg   1980
cataatgcca agacaaagcc gcgggaggag cagtacaaca gcacgtaccg tgtggtcagc   2040
gtcctcaccg tcctgcacca ggactggctg aatggcaagg agtacaagtg caaggtctcc   2100
aacaaagccc gcccagcccc catcgagaaa accatctcca agccaaagg gcagcccga    2160
gaaccacagg tgtaccccct gcccccatcc cgggatgagc tgaccaagaa ccaggtcagc   2220
ctgacctgcc tggtcaaagg cttctatccc agcgacatcg ccgtggagtg ggagagcaat   2280
gggcagccgg agaacaacta caagaccttc ctcccgtgc tggactccga cggctccttc    2340
ttcctctaca gcaagctcac cgtggacaag agcaggtggc agcaggggaa cgtcttctca   2400
tgctctgtga tgcatgaggc tctgaaattc cactacacgc agaagagcct ctccctgtct   2460
ccgggtaaa                                                           2469

SEQ ID NO: 32        moltype = AA  length = 823
FEATURE              Location/Qualifiers
source               1..823
                     mol_type = protein
                     organism = Homo sapiens
SEQUENCE: 32
MASPGSGFWS FGSEDGSGDS ENPGTARAWC QVAQKFTGGI GNKLCALLYG DAEKPAESGG     60
SQPPRAAARK AACACDQKPC SCSKVDVNYA FLHATDLLPA CDGERPTLAF LQDVMNILLQ    120
YVVKSFDRST KVIDFHYPNE LLQEYNWELA DQPQNLEEIL MHCQTTLKYA IKTGHPRYFN    180
QLSTGLDMVG LAADWLTSTA NTNMFTYEIA PVFVLLEYVT LKKMREIIGW PGGSGDGIFS    240
PGGAISNMYA MMIARFKMFP EVKEKGMAAL PRLIAFTSEH SHFSLKKGAA ALGIGTDSVI    300
LIKCDERGKM IPSDLERRIL EAKQKGFVPF LVSATAGTTV YGAFDPLLAV ADICKKYKIW    360
MHVDAAWGGG LLMSRKHKWK LSGVERANSV TWNPHKMMGV PLQCSALLVR EEGLMQNCNQ    420
MHASYLFQQD KHYDLSYDTG DKALQCGRHV DVFKLWLMWR AKGTTGFEAH VDKCLELAEY    480
LYNIIKNREG YEMVFDGKPQ HTNVCFWYIP PSLRTLEDNE ERMSRLSKVA PVIKARMMEY    540
GTTMVSYQPL GDKVNFFRMV ISNPAATHQD IDFLIEEIER LGQDLGGGGS VEPKSSDKTH    600
TCPPCPAPEL LRGPSVFLFP PKPKDTLYIT REPEVTCVVV DVSHEDPEVK FNWYVDGVEV    660
HNAKTKPREE QYNSTYRVVS VLTVLHQDWL NGKEYKCKVS NKARPAPIEK TISKAKGQPR    720
EPQVYTLPPS RDELTKNQVS LTCLVKGFYP SDIAVEWESN GQPENNYKTF PPVLDSDGSF    780
FLYSKLTVDK SRWQQGNVFS CSVMHEALHF HYTQKSLSLS PGK                      823

SEQ ID NO: 33        moltype = DNA  length = 1683
FEATURE              Location/Qualifiers
source               1..1683
                     mol_type = genomic DNA
                     organism = Homo sapiens
SEQUENCE: 33
atgagtgaca gacccacagc aaggcggtgg ggtaagtgtg acctttgtgt accagagag      60
aacatcatgt tggctttcaa aggggtctgg actcaagctt tctggaaagc agtcacagcg    120
gaatttctgg ccatgcttat ttttgttctc ctcagcctgg gatccaccat caactggggt    180
ggaacagaaa agccttttacc ggtcgacatg gttctcatct ccctttgctt tggactcagc   240
attgcaacca tggtcagtg cttttggccat atcagcggtg gccacatcaa ccctgcagtg   300
actgtggcca tggtgtgcac caggaagatc agcatcgcca gtctgtctt ctacatcgca    360
gcccagtgcc tgggggccat cattggagca ggaatcctct atctggtcac acctcccagt   420
gtggtgggag gctgggagtc accatggtt catgaaaatc ttaccgctgg tcatggtctc    480
ctggttgagt tgataatcac attttcaattg gtgtttacta tctttgccag ctgtcgattcc   540
aaacggactg atgtcactgg ctcaattaget ttagcaattg gattttctgt tgcaattgaa   600
catttattttg caatcaatta tactggtgcc agcatgaatc ccgccgatc ctttggacct    660
gcagtttatca tgggaaattg ggaaaaccat tggatatatt gggtcgggcc catcatagga   720
gctgtcctcg ctggtggcct ttatgagtat gtcttctgtc cagatgttga attcaaacgt    780
cgttttaaag aagccttcag caaagctgcc cagcaaacaa aaggaagcta catggaggtg   840
gaggacacaa ggagtcaggt agaaacggat gacctgattc taaaaacctgg agtgagtgca   900
gtgattgacg ttgaccgggg agaggagaag aagggaaag accaatcggg agaggtattg    960
tcttcagtag gagcggtgg atcagttgag cccaaatctt ctgacaaaac tcacacatgc   1020
ccaccgtgcc cagcacctga actcctgagg ggaccgtcag tcttcctctt ccccccaaaa   1080
cccaaggaca cccctctacat cactcgggaa cctgaggtca catgcgtggt ggtggacgtg   1140
agccacgaag accctgaggt caagttcaac tggtacgtgg acggcgtgga ggtgcataat   1200
```

```
gccaagacaa agccgcggga ggagcagtac aacagcacgt accgtgtggt cagcgtcctc    1260
accgtcctgc accaggactg gctgaatggc aaggagtaca agtgcaaggt ctccaacaaa    1320
gcccgcccag cccccatcga gaaaaccatc tccaaagcca agggcagcc ccgagaacca     1380
caggtgacca ccctgccccc atcccgggat gagctgacca gaaaccaggt cagcctgacc    1440
tgcctggtca aaggcttcta tcccagcgac atcgccgtgg agtgggagag caatgggcag    1500
ccggagaaca actacaagac cttccctccc gtgctggact ccgacggctc cttcttcctc    1560
tacagcaagc tcaccgtgga caagagcagg tggcagcagg ggaacgtctt ctcatgctct    1620
gtgatgcatg aggctctgaa attccactac acgcagaaga gcctctccct gtctccgggt    1680
aaa                                                                  1683

SEQ ID NO: 34          moltype = AA   length = 561
FEATURE                Location/Qualifiers
source                 1..561
                       mol_type = protein
                       organism = Homo sapiens
SEQUENCE: 34
MSDRPTARRW GKCGPLCTRE NIMVAFKGVW TQAFWKAVTA EFLAMLIFVL LSLGSTINWG     60
GTEKPLPVDM VLISLCFGLS IATMVQCFGH ISGGHINPAV TVAMVCTRKI SIAKSVFYIA    120
AQCLGAIIGA GILYLVTPPS VVGGLGVTMV HGNLTAGHGL LVELIITFQL VFTIFASCDS    180
KRTDVTGSIA LAIGFSVAIG HLFAINYTGA SMNPARSFGP AVIMGNWENH WIYWVGPIIG    240
AVLAGGLYEY VFCPDVEFKR RFKEAFSKAA QQTKGSYMEV EDNRSQVETD DLILKPGVVH    300
VIDVDRGEEK KGKDQSGEVL SSVGGGGSVE PKSSDKTHTC PPCPAPELLR GPSVFLFPPK    360
PKDTLYITRE PEVTCVVVDV SHEDPEVKFN WYVDGVEVHN AKTKPREEQY NSTYRVVSVL    420
TVLHQDWLNG KEYKCKVSNK ARPAPIEKTI SKAKGQPREP QVTTLPPSRD ELTKNQVSLT    480
CLVKGFYPSD IAVEWESNGQ PENNYKTFPP VLDSDGSFFL YSKLTVDKSR WQQGNVFSCS    540
VMHEALKFHY TQKSLSLSPG K                                              561

SEQ ID NO: 35          moltype = AA   length = 11
FEATURE                Location/Qualifiers
REGION                 1..11
                       note = protein sequence - artificial
source                 1..11
                       mol_type = protein
                       organism = synthetic construct
SEQUENCE: 35
GSSGGSGGGG S                                                         11

SEQ ID NO: 36          moltype = AA   length = 15
FEATURE                Location/Qualifiers
REGION                 1..15
                       note = protein sequence - artificial
source                 1..15
                       mol_type = protein
                       organism = synthetic construct
SEQUENCE: 36
GGGGSGGGGS GGGGS                                                     15

SEQ ID NO: 37          moltype = AA   length = 6
FEATURE                Location/Qualifiers
REGION                 1..6
                       note = protein sequence - artificial
source                 1..6
                       mol_type = protein
                       organism = synthetic construct
SEQUENCE: 37
IEGRMD                                                               6

SEQ ID NO: 38          moltype = AA   length = 5
FEATURE                Location/Qualifiers
REGION                 1..5
                       note = protein sequence - artificial
source                 1..5
                       mol_type = protein
                       organism = synthetic construct
SEQUENCE: 38
GGGGS                                                                5
```

The invention claimed is:

1. A method of depleting target antigen-specific antibody from a patient, the method comprising:
   administering to the patient a Seldeg in an amount sufficient to remove at least 50% of the target antigen-specific antibody from a circulation or a target tissue in the patient,
   wherein the Seldeg comprises
   a targeting component having a protein or a protein fragment configured to specifically bind to an internalizing cell surface receptor or internalizing surface molecule; and
   an antigen component, having one molecule of an antigen, an antigen fragment or an antigen mimetic configured to specifically bind a target antigen-specific antibody or a variant thereof;
   wherein the targeting protein component is fused directly or indirectly to the antigen component.

2. The method of claim 1, comprising administering the Seldeg in an amount sufficient to remove at least 50% of the target antigen-specific antibody from the circulation or the target tissue in the patient within five hours of administration.

3. The method of claim 1, wherein the protein or the protein fragment is configured to bind to the internalizing cell surface receptor or other internalizing cell surface molecule with a dissociation constant of less than 10 µM at near neutral pH.

4. The method of claim 1, wherein the amount sufficient of Seldeg is an amount at least equimolar to the amount of target antigen-specific antibody to be depleted.

5. The method of claim 1, comprising administering the Seldeg in an amount sufficient to remove at least 90% of the target antigen-specific antibody from the circulation or the target tissue in the patient within two hours of administration.

6. The method of claim 1, comprising administering the Seldeg in an amount sufficient to remove at least 50% of the target antigen-specific antibody from the circulation or the target tissue in the patient within one hour of administration.

7. The method of claim 1, further comprising re-administering the Seldeg whenever 50% of patients are expected to have regenerated a threshold amount of target antigen-specific antibody in the circulation of target tissue.

8. The method of claim 1, wherein the Seldeg removes less than 10% of non-target antibodies in the circulation or in the tissue targeted by the target antigen-specific antibody.

9. The method of claim 1, wherein the Seldeg removes an amount of non-targeted antibodies in the circulation or in the target tissue of the patient that does not cause a clinically adverse effect in the patient.

10. The method of claim 1, wherein the Seldeg removes less than 1% of non-target antibodies in the circulation or in a tissue targeted by the target antigen-specific antibody.

11. The method of claim 1, wherein the target antigen-specific antibody is delivered to lysosomes within the cell following Seldeg-mediated internalization of the target antibody by an internalizing cell surface receptor.

12. The method of claim 1, wherein the Seldeg is administered to a patient with an autoimmune disease and the target antigen-specific antibody specifically binds to an autoantigen.

13. The method of claim 1, wherein the Seldeg is administered to a patient receiving a transplanted organ and the target antigen-specific antibody specifically binds to an antigen on the transplanted organ.

14. The method of claim 1, wherein the Seldeg is administered to increase contrast during tumor imaging and the target antigen-specific antibody specifically binds to a tumor antigen.

15. The method of claim 1, wherein the Seldeg is administered to a patient who has received a biologic and the target antigen-specific antibody is the biologic.

16. The method of claim 1, wherein the Seldeg is administered prior to the delivery of a therapeutic agent, if the patient has antibodies specific for the therapeutic agent, and the Seldeg is configured to target the antibodies specific for the therapeutic agent.

17. The method of claim 1, wherein the Seldeg is administered to provide a PET image contrast agent.

18. The method of claim 1, wherein said targeting component is selected from the group consisting of:
   (1) an antibody or antibody fragment, having
      (i) a dissociation constant for FcRn at a pH greater than 6.8 and less than 7.5 of less than 10 µM; and/or
      (ii) an altered binding affinity for FcγRs and/or complement (C1q), compared with a wild-type Fc fragment or is an Fc fragment derived from IgG2 or IgG4;
   (2) an antibody or antibody fragment specific for an internalizing cell surface receptor, wherein the Fc fragment of said antibody or antibody fragment is:
      (i) engineered to have an altered binding affinity for FcγRs and/or complement (C1q), compared with a wild-type Fc fragment; or
      (ii) an Fc fragment derived from IgG2 or IgG4;
   (3) a ligand for an internalizing cell surface receptor, wherein said ligand is fused to an antibody Fc fragment which is
      (i) engineered to have an altered binding affinity for FcγRs and/or complement (C1q), compared with a wild-type Fc fragment; or
      (ii) derived from IgG2 or IgG4;
   (4) an antibody or antibody fragment specific for transferrin receptor, phosphatidylserine, asialoglycoprotein receptor, inhibitory FcγR or mannose-6-phosphate receptor; and
   (5) a ligand for FcRn, transferrin receptor, phosphatidylserine, asialoglycoprotein receptor, inhibitory FcγR or mannose-6-phosphate receptor.

* * * * *